(12) United States Patent
Kim et al.

(10) Patent No.: US 10,533,231 B2
(45) Date of Patent: Jan. 14, 2020

(54) ARTIFICIAL BIOLUMINESCENT ENZYME

(71) Applicant: NATIONAL INSTITUTE OF ADVANCED INDUSTRIAL SCIENCE AND TECHNOLOGY, Tokyo (JP)

(72) Inventors: Sung Bae Kim, Tsukuba (JP); Masaki Torimura, Tsukuba (JP); Hiroaki Tao, Tsukuba (JP); Tetsuya Nakazato, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 754 days.

(21) Appl. No.: 14/438,534

(22) PCT Filed: Sep. 18, 2013

(86) PCT No.: PCT/JP2013/075202
§ 371 (c)(1),
(2) Date: Apr. 24, 2015

(87) PCT Pub. No.: WO2014/065047
PCT Pub. Date: May 1, 2014

(65) Prior Publication Data
US 2015/0284813 A1    Oct. 8, 2015

(30) Foreign Application Priority Data

Oct. 26, 2012 (JP) ................................. 2012-236872
Oct. 26, 2012 (JP) ................................. 2012-237043

(51) Int. Cl.
| | | |
|---|---|---|
| *C12N 9/02* | (2006.01) | |
| *C12Q 1/6897* | (2018.01) | |
| *C12Q 1/66* | (2006.01) | |
| *C07K 14/72* | (2006.01) | |
| *G01N 33/535* | (2006.01) | |

(52) U.S. Cl.
CPC ............ *C12Q 1/6897* (2013.01); *C07K 14/72* (2013.01); *C12N 9/0069* (2013.01); *C12Q 1/66* (2013.01); *G01N 33/535* (2013.01); *C07K 2319/61* (2013.01); *C07K 2319/70* (2013.01); *C12Y 113/12007* (2013.01)

(58) Field of Classification Search
CPC ... C12N 9/02; C12N 1/19; C12N 1/21; C12N 5/10; C12N 15/53; C12N 15/63
See application file for complete search history.

(56) References Cited

U.S. PATENT DOCUMENTS

| | | | |
|---|---|---|---|
| 8,043,827 B2 | 10/2011 | Kim et al. | |
| 8,124,424 B2 | 2/2012 | Umezawa et al. | |
| 2004/0219527 A1 | 11/2004 | Golz et al. | |
| 2009/0123954 A1 | 5/2009 | Kim et al. | |
| 2009/0233320 A1 | 9/2009 | Takenaka | |
| 2009/0269781 A1 | 10/2009 | Kim et al. | |
| 2012/0034672 A1 | 2/2012 | Kim et al. | |

FOREIGN PATENT DOCUMENTS

| | | |
|---|---|---|
| JP | 2004-516828 A | 6/2004 |
| JP | 2011-067190 A | 4/2011 |
| JP | 2012-249619 A | 12/2012 |
| WO | WO 2002/042470 A1 | 5/2002 |
| WO | WO 2006/061906 A1 | 6/2006 |
| WO | WO 2008/084869 A1 | 7/2008 |
| WO | WO 2010/119721 A1 | 10/2010 |
| WO | WO 2011/005978 A2 | 1/2011 |
| WO | WO 2011/102178 A1 | 8/2011 |
| WO | WO 2012/071631 A1 | 6/2012 |

OTHER PUBLICATIONS

Hall et al., *ACS Chemical Biology*, 7: 1848-1857 (2012).
Herring et al., *Marine Ecology-Progress Series*, 94: 297-309 (1993).
Kim et al., *ACS Chemical Biology*, 2(7): 484-492 (2007).
Kim et al., *ACS Chemical Biology*, 3(6): 359-372 (2008).
Kim et al., *Analytical Chemistry*, 77(20): 6588-6593 (2005).
Kim et al., *Analytical Chemistry*, 79(5): 1874-1880 (2007).
Kim et al., *Analytical Chemistry*, 79(13): 4820-4826 (2007).
Kim et al., *Analytical Chemistry*, 81(1): 67-74 (2009).
Kim et al., *Analytical Chemistry*, 83: 8732-8740 (2011).
Kim et al., *Analytical Sciences*, 25: 1415-1420 (2009).
Kim et al., *Bioconjugate Chemistry*, 19(12): 2480-2486 (2008).
Kim et al., *Bioconjugate Chemistry*, 22(9): 1835-1841 (2011).
Kim et al., *Bioconjugate Chemistry*, 20(12): 2324-2330 (2009).
Kim et al., "Methods of Analysis for Imaging and Detecting Ions and Molecules" (chapter 13) in *Cellular and Biomolecular Recognition* (Raz Jelinek, editor), pp. 299-338 (2009).
Kim et al., *Proc. Natl. Acad. Sci. U.S.A.*, 101(32): 11542-11547 (2004).
Kim et al., *Protein Engineering, Design and Selection*, 25(6): 261-269 (2012).
Lehman et al., *Protein Engineering*, 15(5): 403-411 (2002).
Li et al., *Appl. Microbiol. Biotechnol.*, 85(4): 909-919 (2010).
Loening et al., *Nature Methods*, 4(8): 641-643 (2007).

(Continued)

*Primary Examiner* — Maryam Monshipouri
(74) *Attorney, Agent, or Firm* — Leydig, Voit & Mayer, Ltd.

(57) ABSTRACT

The invention relates to establishment of a series of artificial luciferases based on artificial amino acid sequences extracted by amino acid alignment of copepod-derived luciferase sequences in a database based on amino acid similarity. The invention provides high luminescence intensity, high luminescence stability, and a spectrum with increased wavelength as luminescence characteristics. A series of artificial luciferases (ALuc) was established. The group of ALucs has superior luminescence characteristics, such as an increase in luminescence intensity, an increase in luminescence stability, or an increase in wavelength of the luminescence spectrum, which were not obtained before. Further, by using the artificial luciferases (ALuc) of the invention, it is possible to provide a novel, superior bioassay system, such as a bioluminescent probe, two-hybrid assay, a luminescent capsule, or the like having improved measurement function.

6 Claims, 39 Drawing Sheets

Specification includes a Sequence Listing.

(56) References Cited

OTHER PUBLICATIONS

Markova et al., *Biochemical and Biophysical Research Communications*, 417: 98-103 (2012).
Markova et al., *The Journal of Biological Chemistry*, 279(5): 3212-3217 (2004).
Michnick et al., *Methods in Enzymology*, 470: 335-368 (2010).
Miyawaki et al., *Current Opinion in Chemical Biology*, 7(5): 557-562 (2003).
Niu et al., *Theranostics*, 2(4): 413-423 (2012).
Okita et al., *Nature*, 448: 313-317 (2007).
Takenaka et al., *Gene*, 425: 28-35 (2008).
Takenaka et al., *Molecular Biology and Evolution*, 29(6): 1669-1681 (2012).
Verhaegen et al., *Anal. Chem.*, 74(17): 4378-4385 (2002).
Welsch et al., *Biochemical and Biophysical Research Communications*, 389: 563-568 (2009).
Japanese Patent Office, International Search Report in International Patent Application No. PCT/JP2013/075202 (dated Dec. 17, 2013).
Takenaka et al., "Two Forms of Secreted and Thermostable Luciferase From the Marine Copepod Crustacean, Metridia Pacifica", GenBank, BAD93333.1 (May 19, 2016).
Kim et al., "Fabrication of a New Lineage of Artificial Luciferases from Natural Luciferase Pools," *ACS Comb. Sci.*, 19(9): 594-599 (2017).

```
ALuc10  MM......FA...C.A..QAN.T.N....DI..V.......QLETDLFTIVEDMNVISRDT.......RG......LPGKK.PLEVL.ELEANAQ..AGCTRGCLICLS.:IKCTAKMKKMKWLP
ALuc15  MM......FA...C.A..QAN.T.N....DI..V.......QLETDLFTIVEDMNVISRDT.......RG......LPGKK.PLEVL.ELEANAQ..AGCTRGCLICLS.:IKCTAKMKKMKWLP
ALuc18  MM......FA...C.A..QAN.T.N....DI..V.......QLETDLFTIVEDMNVISRDT.......RG......LPGKK.PLEVL.ELEANAQ..AGCTRGCLICLS.:IKCTAKMKKMKWLP
ALuc16  MM......FA...C.A..QAN.T.N....DI..V.......QLETDLFTIVEDMNVISRDT.......RG......LPGKK.PLEVL.ELEANAQ..AGCTRGCLICLS.:IKCTAKMKKMKWLP
ALuc23  MM......FA...C.A..QAN.T.N....DI..V.......QLETDLFTIVEDMNVISRDT.......RG......LPGKK.PLEVL.ELEANAQ..AGCTRGCLICLS.:IKCTAKMKKMKWLP
ALuc22  MM......FA...C.A..QAN.T.N....DI..V.......QLETDLFTIVEDMNVISRDT.......RG......LPGKK.PLEVL.ELEANAQ..AGCTRGCLICLS.:IKCTAKMKKMKWLP
ALuc25  MM......FA...C.A..QAN.T.N....DI..V.......QLETDLFTIVEDMNVISRDT.......RG......LPGKK.PLEVL.ELEANAQ..AGCTRGCLICLS.:IKCTAKMKKMKWLP
        **  ::::***:*.*:.***.*.**::  *  *;::    .:********************,     .**:     *******.*****.*******. ********,  **************

ALuc10  GRCESW.GDK..GQGGI..E...VDIPEIPGFK.L.PMEQFIAQVDLC.DCTTGCLKGLANVKCS.LLKKWLPSRCA.FA.KIQAQVD.IKGAGGS
ALuc15  GRCESW.GDK..GQGGI..E...VDIPEIPGFK.L.PMEQFIAQVDLC.DCTTGCLKGLANVKCS.LLKKWLPSRCA.FA.KIQAQVD.IKGAGGS
ALuc18  GRCESW.GDK..GQGGI..E...VDIPEIPGFK.L.PMEQFIAQVDLC.DCTTGCLKGLANVKCS.LLKKWLPSRCA.FA.KIQAQVD.IKGAGGS
ALuc16  GRCESW.GDK..GQGGI..E...VDIPEIPGFK.L.PMEQFIAQVDLC.DCTTGCLKGLANVKCS.LLKKWLPSRCA.FA.KIQAQVD.IKGAGGS
ALuc23  GRCESW.GDK..GQGGI..E...VDIPEIPGFK.L.PMEQFIAQVDLC.DCTTGCLKGLANVKCS.LLKKWLPSRCA.FA.KIQAQVD.IKGAGGS
ALuc22  GRCESW.GDK..GQGGI..E...VDIPEIPGFK.L.PMEQFIAQVDLC.DCTTGCLKGLANVKCS.LLKKWLPSRCA.FA.KIQAQVD.IKGAGGS
ALuc25  GRCESW.GDK..GQGGI..E...VDIPEIPGFK.L.PMEQFIAQVDLC.DCTTGCLKGLANVKCS.LLKKWLPSRCA.FA.KIQAQVD.IKGAGGS
        ******.***..*****.:*****.*.***********.**********,.*************** **.*******.  *,  ******. *******
``` x = any OK
y = hydrophobic
z = hydrophilic

ARTIFICIAL BIOLUMINESCENT ENZYME

CROSS-REFERENCE TO RELATED APPLICATIONS

This patent application is the U.S. national phase of International Patent Application No. PCT/JP2013/075202, filed Sep. 18, 2013, which claims the benefit of Japanese Patent Application No. 2012-237043, filed on Oct. 26, 2012, and Japanese Patent Application No. 2012-236872, filed on Oct. 26, 2012, the disclosure of which is disclosures of which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 74,218 bytes ASCII (Text) file named "720602Sequence-Listing.txt," created Apr. 23, 2015.

TECHNICAL FIELD

The present invention relates to the creation of artificial bioluminescent enzymes that exhibit stable bioluminescence with high luminescence intensity based on common genetic information of marine animal-derived bioluminescent enzymes. Further, the present invention also relates to an optimal reaction solution to be used for assays using bioluminescence.

BACKGROUND ART

The establishment of many novel bioluminescent enzymes (luciferases) has recently been reported. For example, Promega reports the establishment of a novel luminescent enzyme originating from a deep-sea shrimp (Non-patent Document 1). The molecular weight of this enzyme is half (19 kD) that of a known *Renilla* luciferase (RLuc), and its luminescence intensity is 100 folds greater. Further, Shigeri et al. reports 11 types of plankton-derived bioluminescent enzyme (Non-patent Document 20). Some of these luminescent enzymes were evaluated to have a luminescence intensity comparable to that of RLuc.

Further, some deep-sea luminescent animals belonging to the Augaptiloidea superfamily have heretofore been discovered (Non-patent Document 2). In addition, a luminescent enzyme originating from *Gaussia princeps* (GLuc), a luminescent enzyme originating from *Metridia longa* (MLuc), and luminescent enzymes originating from *Metridia pacifica* (MpLuc1 and MpLuc2), which all belong to the Metridinidae family, have also been discovered (Non-patent Documents 15, 19, and 21).

Meanwhile, research for improving the luminescence intensity or luminescence stability of these luminescent enzymes has progressed. Loening et al. established a stable RLuc variant having high luminescence intensity by using a method of introducing amino acid mutations into RLuc (Non-patent Document 14). In this study, a "consensus sequence-driven mutagenesis strategy" was used to specify the mutation introduction site (Non-patent Document 13). Further, the present researchers also succeeded in increasing the luminescence intensity and luminescence stability of GLuc, MpLuc1, and MLuc, which are luminescent enzymes originating from deep-sea luminescent animals, by using a method of predicting the enzyme active site based on a hydrophilic amino acid distribution chart, and introducing a variant into the site (Non-patent Document 11). However, these luminescent enzymes were still insufficient as enzymes usable for various bioassays, and improvement in luminescence characteristics, such as increase in luminescence intensity, has been desired.

The present inventors once suggested production of a thermodynamically stable luminescent enzyme sequence with an attempt to obtain information regarding the luminescence characteristics by bisecting a single luminescent enzyme sequence, and aligning the first half and the second half of the sequence based on the similarity in amino acid (single sequence alignment; SSA) (Non-patent Document 3). This method is based on the premise that a marine animal-derived luminescent enzyme has two enzyme active sites. By aligning the two enzyme active sites based on similar amino acids, it is possible to easily examine the similarity of the enzyme active site in the first half and the enzyme active site in the second half. This method attempts to produce a thermodynamically stable luminescent enzyme sequence by increasing the similarity of the first and second half of the sequence on the aforementioned presumption that the amino acid frequency is relevant to the thermodynamic stability.

Meanwhile, various applied technologies using a bioluminescent enzyme as a "reporter" have also been developed. Niu et al. classified the bioassays using a bioluminescent enzyme as a reporter into three groups: "basic," "inducible," and "activatable" (Non-patent Document 16). This classification is based on the characteristics of the reporter gene. First of all, the difference between "basic" and "inducible" is the presence or absence of an expression controlling character in the reporter expression by the promoter, and the difference in expression amount. A later-described antibody having a bioluminescent enzyme attached thereto corresponds to "basic," and the bioluminescence resonance energy transfer (BRET) and two-hybrid assay belong to the category of "inducible." The reporter-gene probes, which belong to the category of "activatable," are characterized in that the reporter actively responds to ligand stimulation and produces bioluminescence. The later-described protein complementation assay (PCA), protein splicing assay (PSA), integrated-molecule-format bioluminescent probe, bioluminescent capsule, and the like belong to the category of "activatable."

For the bioassays (hereinafter may also be simply referred to as "reporter assays") using these bioluminescent enzymes as a reporter, various luminescent probes have been actively developed based on the aforementioned novel luminescent enzymes. The present inventors have heretofore conducted research and development regarding bioluminescence imaging using unique molecular design technology. More specifically, the inventors developed a method of measuring translocation of transcription factors into the nucleus or nongenomic protein-protein interactions in the cytosol using protein splicing (Non-patent Documents 7 and 8), and an integrated-molecule-format bioluminescent probe in which all of the necessary elements for signal recognition and bioluminescence emission are integrated (Non-patent Documents 4 and 6). Thereafter, the probes were multicolorized, and developed to be capable of simultaneous imaging of multiple signal-transduction processes (Non-patent Document 12). Moreover, the inventors further developed a circular permutation technique (Non-patent Document 9) and a molecular design technology using low-molecular-weight bioluminescent enzymes (Non-patent Document 12)

as strategies for improving the ligand sensitivity of the bioluminescent probe. These technologies have been used as means for efficiently measuring molecular phenomena in cellular and cell-free systems.

Regarding the main research tools for exploring intra- or extracellular molecular phenomena, fluorescence imaging has been used more widely than luminescence imaging. However, due to their autofluorescence property, fluorescent proteins generate a high background, requiring an external light source. Therefore, fluorescence imaging requires a large instrumentation, such as a fluorescence microscope, and a sophisticated light-filtering system. Fluorescence imaging also has a drawback in that the maturation of a fluorescence chromophore takes at least several hours to several days. Further, since the number of simultaneously observable cells is limited for each measurement with a fluorescence microscope, quantitative measurement has been problematic (Non-patent Document 8).

On the other hand, bioluminescence imaging using a bioluminescent enzyme has, despite its many advantages, a critical problem regarding poor luminescence intensity of bioluminescent enzymes. This problem has decreased the popular use of bioluminescence imaging, compared with fluorescence imaging. Because of this poor bioluminescence intensity of bioluminescent enzymes, high-sensitivity detectors were required; therefore, bioluminescent enzymes have been considered inappropriate for single-cell imaging or exploration of organelles.

Further, studies on multicolor fluorescent proteins have greatly progressed, and many facts regarding their coloring mechanisms have been discovered; thus, many fluorescent proteins with diversified fluorescent characters have been developed based on these study results. In contrast, only limited kinds of bioluminescent enzymes exhibit multiple colors. Although it has been known that diversification of bioluminescent colors is advantageous in that (i) it enables simultaneous measurement of multiple cellular signals, and that (ii) it ensures a tissue permeability of red-shifted bioluminescence in living subjects, nearly no systematic study for diversifying the colors of bioluminescent enzymes based on their luminescence mechanisms has been conducted.

Accordingly, there has been a strong desire to newly establish a high-performance bioluminescent enzyme, increase its luminescence intensity and stability, and ensure heat resistance and salt tolerance. Further, a systematic study for red-shift of wavelength of bioluminescent color has also been highly desired.

In addition, appropriate selection of the reaction solution is an important factor in bioassays, and may influence the assay results. In particular, (1) reporter-gene assay, (2) two-hybrid assay, (3) enzyme-linked immunosorbent assay, and (4) radioimmunoassay (RIA) (Non-patent Document 22 and Non-patent Document 23) require more careful selection of the reaction solution.

A bioassay using a so-called "molecular probe" is another example of a bioassay in which the results greatly depend on the selection of the reaction solution. For example, color imaging of intracellular protein-protein interaction, i.e., (1) FRET assay using fluorescence resonance energy transfer of fluorescent protein (Non-patent Document 24), (2) 2-molecule-format protein complementation assay (PCA) characterized by luminescence recovery by bisection of a fluorescent protein or a luminescent protein into two fragments and recombining the fragments, and the like have been developed (Non-patent Document 25). The present inventors also developed an assay method using a protein splicing reaction (protein splicing assay (PSA)) (Non-patent Document 8).

Thereafter, the present inventors developed (1) an integrated-molecule-format bioluminescent probe (may also be simply referred to as a single-chain probe) that enables detection of a single fusion molecular protein-protein interaction (Non-patent Document 6 and Patent Document 4), and, as a derivative method thereof, (2) a bioluminescent probe that is produced through circular permutation of the gene sequence of a luminescent enzyme (Non-patent Document 8 and Patent Document 3). The present inventors further developed (3) a molecular stress sensor (molecular tension-indexed bioluminescent probe) based on the difference in enzymatic activity caused by an artificial stress applied to a luminescent enzyme (Non-patent Document 26 and Patent Document 5).

Recently, the present inventors developed a multiple recognition-type bioluminescent probe obtained as a combined technique of reporter-gene assay and integrated-molecule-format bioluminescent probe (Non-patent Document 27). This probe is characterized by two sensing steps for a single target substance. The present inventors further developed a multicolor bioluminescence imaging probe set by combining two colors of integrated-molecule-format bioluminescent probes (Patent Document 25). This probe is characterized by multicolor imaging of multiple aspects of bioactivity of a test substance.

Bioassays indispensably require a reaction solution, and are roughly classified into (1) a method using a fluorescent protein and (2) a method using a bioluminescent enzyme (luciferase), depending on the type of the luminescence signal. In the method using a fluorescent protein, a high background is generated due to the autofluorescence, and an external light source is necessary. Further, a relatively large luminescence detector having a precise spectral filter is problematically necessary to measure the fluorescence (e.g., a fluorescence microscope) (Non-patent Document 8). On the other hand, although the method using a bioluminescent enzyme does not have the above problems, it indispensably requires substrates because of a drawback such that the light emission of bioluminescence is weaker than that of fluorescence. Further, since the method using a bioluminescent enzyme relies on the luminescence of enzyme, easy changes in luminescence quantity depending on the salt concentration, temperature, pH, heavy-metal ion concentration, and the like become problematic. The method using fluorescence also has similar problems. Therefore, to fix the pH and optimize the luminescence reaction conditions, reaction solutions are widely used both in the fluorescence method and the luminescence method.

Considering such circumstances, the determination of the optimal buffer condition is an important factor to accomplish a successful assay in the various known assays using fluorescence or bioluminescence. Further, optimization of the reaction solution and the additives according to the characteristics of the bioassay has been desired so as to obtain sufficient detection sensitivity, selectivity, and signal stability.

To improve the assay effect, various additives have been used for reaction solutions (assay buffer). The additives must have functions for ensuring homogenous assay conditions, including (1) prevention of protein decomposition by protease, (2) suppression of influences of interfering substances, (3) ensuring the function as a buffer solution for supporting stable signal generation, and (4) causing mild breakage of the plasma membrane. Therefore, the additives (5) must stabilize the protein and (6) must not inhibit the probe performance that is the core of the luminescence reaction.

The major additives of the reaction solution include, as salts, NaCl, KCl, $(NH_4)_2SO_4$, and the like; as an SH reagent, mercapto ethanol, DTT, and the like; as a polyol, glycerol, sucrose, and the like; and as a chelating reagent, EGTA, EDTA, and the like.

Examples of surfactants include polyoxyethylene (10) octylphenyl ether (Triton X-100; TX100), Nonidet P-40 (NP40), polyoxyethylene sorbitan monolaurate (Tween 20; TW20), polyoxyethylene sorbitan monooleate (Tween 80; TW80), polyoxyethylene (20) cetyl ether (Brij58), sodium dodecyl sulfate (SDS), and the like. Heretofore, a suitable surfactant has been selected by referring to the order of the hydrophilic degree of the surfactants, which is TW20>Brij58>TW80>TX100>NP40, and the order of the degree of surface activity, which is NP40>TX100>Brij58>TW20>TW80.

Examples of protease inhibitors to be used for inhibiting protein decomposition include aprotinin (molecular weight: 6.5 kD), leupeptin (molecular weight: 427), pepstatin A (molecular weight: 686), phenylmethylsulfonyl fluoride (PMSF, molecular weight: 174), antipain (molecular weight: 605), chymostatin (molecular weight: 608) and the like. Further, Pefabloc SC (AEBSF, 240 Da), DFP (184 Da), p-APMSF (216 Da), STI (20,100 Da), leupeptin (460 Da), N-tosyl-L-phenylalaninechloromethylketone, 3,4-dichloroisocoumarin (215 Da), EDTA-Na2 (372 Da), EGTA (380 Da), 1,10-phenanthroline (198 Da), phosphoramidon (580 Da), Dithiobis (2-amino-4-methylpentane), E-64 (357 Da), cystatin, bestatin, epibestatin hydrochloride, aprotinin, minocycline, ALLN (384 Da), and the like have been used as protein decomposition inhibitors.

Further, the functional chemical substances below may also be added. By adding sodium molybdate, it is possible to stabilize the receptors and thus protect them from decomposition. Glycerol can be used as a protein blocking agent. Dithiothreitol (DTT) has been used as a reducing agent.

Additionally, as buffers, p-toluenesulfonic acid, tartaric acid, citric acid, phthalate, glycine, trans-aconitic acid, formic acid, 3,3-dimethylglutaric acid, phenylacetic acid, sodium acetate, succinic acid, sodium cacodylate, sodium hydrogen maleate, maleic acid, sodium phosphate, $KH_2PO_4$, imidazole, 2,4,6-trimethylpyridine, triethanolamine hydrochloride, sodium 5,5-diethylbarbiturate, N-ethylmorpholine, sodium pyrophosphate, tris(hydroxymethyl)aminomethane, bicine, 2-amino-2-methylpropane-1,3-diol, diethanolamine, potassium p-phenolsulfonate, boric acid, sodium borate, ammonia, glycine, $Na_2CO_3/NaHCO_3$, sodium borate, or a combination of these substances, have been used.

Under such circumstances, selection of additives to be added to the reaction solution is crucially important, and appropriate selection of the additives and optimization of the reaction solution have been desired in the existing bioassays.

In addition, the known bioassays have a problematic need for multiple reaction buffers. This problem has caused the method to become complex, or increased the cost thereof. This problem has also caused the assay steps performed by the user to become complex.

For example, to perform reporter-gene assay, first of all, a plasmid containing a reporter gene is introduced into cultured cells in a microplate. Thereafter, ligand stimulation was performed for about 12 hours. Then, after the medium is discarded, the cells are washed once with a PBS (phosphate buffered saline) buffer (the first buffer). Next, the cells in the microplate are lysed with a cell lysis buffer (the second buffer) for 20 minutes. This cell lysis buffer is mixed with an assay buffer containing a substrate (the third buffer) in a predetermined proportion, and the luminescence value is immediately measured. As such, reporter-gene assay requires at least three buffers and a long measurement step.

Further, in the method using the "integrated-molecule-format bioluminescent probe," a similar measurement step was necessary. First, an expression vector of the "integrated-molecule-format bioluminescent probe" is introduced into eukaryotic cells cultured in a microplate; the cells are then cultured again for 16 hours. The cells are then subjected to ligand stimulation for 20 to 30 minutes. Finally, the medium is discarded, and the cells are washed once or twice with a PBS buffer (the first buffer). The remaining cells are treated with a cell lysis buffer (the second buffer) for 20 minutes. Thereafter, the lysate is mixed with an assay buffer (the third buffer) containing a substrate at an appropriate ratio, thereby causing a luminescence reaction. The luminescence value is immediately measured with a luminometer (Non-patent Documents 26 and 27).

All of the above known methods use a plurality of reaction buffers, require a cumbersome measurement step, and take a long time. Therefore, there has been a demand for an improved method in which the measurement step can be simplified and the measurement time can be reduced.

CITATION LIST

Patent Documents

Patent Document 1: Specification of U.S. Pat. No. 8,124,424
Patent Document 2: Specification of U.S. Pat. No. 8,043,827
Patent Document 3: Specification of US publication No. US-2009-0269781 (A1)
Patent Document 4: International publication WO2008/084869 (International application No. PCT/JP2008/050370)
Patent Document 5: JP2011-067190A
Patent Document 6: US patent No. US-2009-0123954 (A1)

Non-Patent Documents

Non-patent Document 1: Hall, M. P., Unch, J., Binkowski, B. F. et al., ACS Chem. Biol. 7 2012 1848.
Non-patent Document 2: Herring, P. J., Latz, M. I., Bannister, N. J. et al., Marine Ecology-Progress Series, 94 1993 297.
Non-patent Document 3: Kim, S. B., Protein Engineering Design & Selection, 25 2012 261.
Non-patent Document 4: Kim, S. B., Awais, M., Sato, M. et al., Anal. Chem., 79 2007 1874.
Non-patent Document 5: Kim, S. B., Kanno, A., Ozawa, T. et al., ACS Chem. Biol., 2 2007 484.
Non-patent Document 6: Kim, S. B., Otani, Y., Umezawa, Y. et al., Anal. Chem., 79 2007 4820.
Non-patent Document 7: Kim, S. B., Ozawa, T., Umezawa, Y., Anal. Chem., 77 2005 6588.
Non-patent Document 8: Kim, S. B., Ozawa, T., Watanabe, S. et al., Proc. Natl. Acad. Sci. U.S.A., 101 2004 11542.
Non-patent Document 9: Kim, S. B., Sato, M., Tao, H., Bioconjugate Chem., 19 2008 2480.
Non-patent Document 10: Kim, S. B., Sato, M., Tao, H., Anal. Chem., 81 2009 67.
Non-patent Document 11: Kim, S. B., Suzuki, H., Sato, M. et al., Anal. Chem., 83 2011 8732.
Non-patent Document 12: Kim, S. B., Umezawa, Y., Kanno, K. A. et al., ACS Chem. Biol., 3 2008 359.

Non-patent Document 13: Lehmann, M., Loch, C., Middendorf, A. et al., Protein Eng., 15 2002 403.

Non-patent Document 14: Loening, A. M., Wu, A. M., Gambhir, S. S., Nat. Methods, 4 2007 641.

Non-patent Document 15: Markova, S. V., Golz, S., Frank, L. A. et al., J. Biol. Chem., 279 2004 3212.

Non-patent Document 16: Niu, G., Chen, X. Y., Theranostics, 2 2012 413.

Non-patent Document 17: Okita, K., Ichisaka, T., Yamanaka, S., Nature, 448 2007 313.

Non-patent Document 18: Papworth, C., Bauer, J. C., Braman, J. et al., Strategies, 9 1996 3.

Non-patent Document 19: Takenaka, Y., Masuda, H., Yamaguchi, A. et al., Gene, 425 2008 28.

Non-patent Document 20: Takenaka, Y., Yamaguchi, A., Tsuruoka, N. et al., Molecular Biology and Evolution, 29 2012 1669.

Non-patent Document 21: Verhaegent, M., Christopoulos, T. K., Anal. Chem., 74 2002 4378.

Non-patent Document 22: S. B. Kim, H. Tao, and Y. Umezawa eds., "Cellular and Biomolecular Recognition," edited by R. Jelinek, p. 299 ((2009) (Wiley-VCH, Darmstadt)).

Non-patent Document 23: W. Li and N. B. Caberoy, Applied Microbiology and Biotechnology 85 (4), 909 (2010).

Non-patent Document 24: A. Miyawaki, T. Nagai, and H. Mizuno, Curr. Opin. Chem. Biol. 7 (5), 557 (2003).

Non-patent Document 25: S. W. Michnick, P. H. Ear, C. Landry et al., Meth. Enzymol. 470, 335 (2010).

Non-patent Document 26: S. B. Kim, M. Sato, and H. Tao, Bioconjugate Chem. 20 (12), 2324 (2009).

Non-patent Document 27: S. B. Kim, Y. Takenaka, and M. Torimura, Bioconjugate Chem. 22 (9), 1835 (2011).

Non-patent Document 28: S. B. Kim, Protein Eng. Des. Sel., 25 (6), 261-269 (2012).

Non-patent Document 29: S. B. Kim, Y. Umezawa, H. Tao, Anal. Sci. 25, 1415-1420 (2009).

SUMMARY OF INVENTION

Technical Problem

An object of the present invention is to provide a novel artificial luciferase (ALuc) that is stable, has a high luminescence intensity, and produces luminescence of a long wavelength with a method of aligning amino acid sequences of many bioluminescent enzymes based on the amino acid similarity, and extracting frequently occurring amino acid sequences. Another object of the present invention is to establish various "reporter assay" methods using the ALuc.

Further, the present invention also intends to provide a reaction solution for optimizing the reaction conditions in bioassays, as well as the additives thereof. By such optimization of the reaction solution, the known cumbersome protocol requiring a plurality of reaction solutions (such as a cell lysis buffer and an assay buffer) becomes unnecessary, and it becomes possible to perform a quick and simple measurement step, and enable a highly sensitive and stable luminescence measurement.

More specifically, another object of the present invention is to provide a bioluminescence reaction buffer, in particular, a bioluminescence reaction buffer that enables a high-sensitivity bioassay even without a cell lysis step, which has been required in a conventional bioassay of living cells using bioluminescence, and even with direct measurement of luminescence from ligand stimulation.

Solution to Problem

In order to provide a novel artificial luciferase (ALuc), the present inventors focused attention on marine animal-derived bioluminescent enzymes.

Among all bioluminescent enzymes, marine animal-derived bioluminescent enzymes have high sequence similarity, and have common characteristics in that luminescence is caused by the same or similar substrate (coelenterazine). The present researchers previously found a method for specifying a mutation region by using a hydrophilicity search (Non-patent Document 11). However, this method can (1) merely roughly presume the approximate mutation region, and is thus not suitable to specify the mutation region with high accuracy. Further, (2) although this hydrophilicity search finds a plurality of hydrophilic regions, no indication was made regarding the method for specifying the target region in which the mutation is to be introduced. (3) Based on this research, the researchers developed a novel luminescent enzyme having a high luminescence intensity by using point mutation. However, this novel enzyme had a drawback of severe substrate consumption (also referred to as turnover rate). Therefore, when the enzyme was used for a luminescent probe, the luminescence intensity was increased only 2 to 5 folds; therefore, the problem of luminescence intensity of luminescent enzymes in bioassays could not be resolved. (4) Further, there also was a problem of great changes in luminescence characteristics depending on the components of the reaction buffer. For example, although a reaction buffer made by Promega increased the luminescence intensity, the luminescence intensity or stability of luminescence were not significantly increased when a reaction buffer or a culture medium made by New England Biolabs (NEB) was used.

Further, the point mutation that was used as a major modification means of the development of the above novel enzyme requires significant time and effort. For example, for a luminescent enzyme made of 200 amino acid (amino acid; AA) sequences, the introduction of a single mutation has only a 1/4000 (200 AA×20 types of AA) probability of success. Therefore, a breakthrough on such inefficiency has also been desired.

Accordingly, despite the above research background, the present inventors found the possibility of the establishment of a completely novel artificial bioluminescent enzyme by careful examination of various findings regarding ocean animal luminescent enzymes in the past. The method can be summarized in the following four steps.

(1) First, the inventors carried out the following steps on the assumption that the amino acid sequences of ocean bioluminescent enzymes accumulated in an official database (NCBI) over many years must be considered those that survived over the long course of evolution. First, the inventors aligned the ocean bioluminescent enzyme sequences in the NCBI based on the amino acid similarity, and extracted frequently occurring amino acids based on an individualistic approach. With this method, the inventors produced many artificial luciferase (ALuc) sequences that did not exist in the past. Despite the many reports of amino acid alignment in the past, these past amino acid alignments were performed for a search for mutation regions. Therefore, these methods were called a consensus sequence-driven mutagenesis strategy (Non-patent Document 13). On the other hand, the inventors of the present invention uniquely interpreted this amino acid sequence alignment, and analyzed it in detail. As a result, the inventors conceived of a unique idea of establishing a novel amino acid sequence group of artificial luminescent enzymes by using the amino acid sequence alignment.

(2) The inventors also contrived the following. First of all, the inventors once reported that a single bioluminescent enzyme has two enzyme active sites; as evidence, the inventors disclosed two domains in overlapping fashion (Non-patent Document 3). The inventors further developed this finding to a new idea of not only bisecting a single amino acid sequence and aligning the resulting two sequences, but also using the alignment for the establishment of novel amino acid sequences of artificial luminescent enzymes. First, the inventors bisected the amino acid sequences of all of the copepod-derived luminescence bioluminescent enzymes obtained from the NCBI at an arbitrary portion. After aligning the first and second domains, the inventors compared corresponding amino acids in the amino acid sequences, and determined an amino acid sequence so that the similarity increases. In this manner, the inventors determined many amino acid sequences as candidates of novel artificial luminescent enzymes.

(3) Further, upon the determination of the amino acid sequences of the artificial luminescent enzymes, the inventors intentionally inserted amino acids incongruous with the rule of sequence similarity into the sequence so as to introduce restriction enzyme sites at certain intervals. With this arrangement, the inventors attempted to simplify the future gene recombination.

(4) By examining the sequence characteristics of the artificially produced N-terminus using PSORTII, the localization can be predicted in silico. By using such public software for predicting the sequence behavior, the inventors increased the probability of sequence efficiency.

With this synthesis of novel artificial bioluminescent enzymes, the inventors attempted to establish novel enzymes having high luminescence intensity and an increased wavelength, as well as luminescence stability, heat resistance, and salt tolerance, which could not be obtained in the known enzymes.

More specifically, the inventors aligned the amino acid sequences of plankton-derived luminescent enzymes published in the NCBI or other documents based on amino acid similarity, and thereby determined a series of novel amino acid sequences mainly based on the common amino acids (Example 1-1). Then, artificial genes were synthesized based on these sequences by applying frequently present codons in mouse genes so as to ensure easy expression of the gene codons in mouse-derived animal cultured cells. Each artificial gene was inserted into a mammalian cell expression vector (pcDNA3.1 (+)), thereby synthesizing a series of novel expression vectors. The series of the vectors were individually introduced into African green monkey kidney-derived COS-7 cells, and the luminescence intensity, the luminescence stability, and the shift to the longer wavelength were examined. The results confirmed that by using some of the artificially synthesized genes, luminescent enzymes having significantly high luminescence intensity, stability, heat resistance, and a luminescence spectrum with an increased wavelength can be synthesized.

Relative luminescence intensity of the series of synthesized artificial bioluminescent enzymes (ALuc) were confirmed using a commercially available substrate kit (Example 1-2), and the luminescence stability of ALuc(s) having a high luminescence intensity was confirmed based on the changes in luminescence intensity over time (Example 1-3). Further, the heat resistance and the extracellular secretion ability of ALuc(s) having good luminescence intensity and good luminescence stability were examined (Example 1-4); additionally, luminescence spectra of some particularly potent ALucs were measured to find their degree of increase in wavelength (Example 1-5). A comparison in similarity between ALucs provided by the present invention and the existing luminescent enzymes found that all of the ALucs had identities of, at most, 83% with the existing luminescent enzymes, and that all of the ALucs provided by the present invention were therefore confirmed to be novel artificial bioluminescent enzymes that are completely different from existing luminescent enzymes (Example 1-6).

Further, during the study of various kinds of "reporter assays" using, as the reporter proteins, a series of high-performance artificial luciferases (ALuc) that were obtained in the process of the above luminescence verification, the inventors developed a new-concept bioluminescence visualization probe called a "luminescent capsule." This probe is normally localized inside the plasma membrane, and is within easy reach of substrates and oxygen. Therefore, compared with localization in other organelles, the luminescence intensity of this luminescence imaging is higher. Additionally, since the probe is localized inside the plasma membrane, the probe can rapidly respond to an external toxic substance, thereby changing the luminescence value (Examples 1-7 and 1-8). The operation of this probe was successful because of the appropriate use of the original characteristics of ALuc (secretion signals (secretion peptides; SP) for enabling transfer to the plasma membrane via the endoplasmic reticulum). Furthermore, this probe is capable of carrying a protein (peptide) as a cargo by inserting the protein thereto, thereby transferring any protein (peptide) to the plasma membrane. Further, in order to perform chemical substance toxicity evaluation using a transformed cell into which this luminescent capsule gene is introduced, a novel luminescence device was experimentally produced (Example 1-11). This device has a spectral filter, a microslide holder, a mirror cap, a photomultiplier tube (PMT), and the like. A transformed cell in which the novel synthesis gene (ALuc) is introduced was exposed to a chemical substance. By measuring the light emitted upon exposure using the above device, toxicity evaluation was efficiently performed (Examples 1-11, 1-12, and 1-13).

Then, by providing the novel synthesis luminescent enzymes (ALuc) in an eukaryotic cell two-hybrid assay (mammalian two-hybrid assay) system as a reporter protein, a novel bioassay system with a higher luminescence intensity and higher stability than known assay systems was constructed (Example 1-9).

Further, in the "reporter assay" using the artificial luciferase (ALuc) as a reporter protein, ALuc was used for an "integrated-molecule-format bioluminescent probe." This probe was constructed according to the method disclosed in Non-patent Document 9. The ALuc gene was bisected into two domains, the N-terminus fragment and the C-terminus fragment were exchanged by circular permutation, and a stress hormone receptor and an LXXLL motif were connected to the outer end of the two domains, respectively. This probe had a high S/N ratio both in the presence and absence of stress hormone (cortisol) (Example 1-10). Further, upon the measurement of stress hormone with this probe, some advantageous effects, such as increase in luminescence intensity, decrease in standard error rate, and the like, were obtained by using the above luminescence device together with the probe (Example 1-14).

As such, it was demonstrated that the ALucs of the present invention served as significantly superior reporter proteins that are stable, and that have a high luminescence intensity in various reporter assays.

The present invention was completed based on such findings.

Specifically, the present invention encompasses the following aspects.

[1] A polypeptide having amino acid sequence (i) or (ii) below, and a copepod luciferase activity:
(i) the amino acid sequence represented by SEQ ID NO: 38; and
(ii) an amino acid sequence represented by SEQ ID NO: 38 in which one or more amino acids are deleted in at least one of a region corresponding to positions 1-31 and a region corresponding to positions 217-221.

[1-1] A polypeptide having amino acid sequence (i) or (ii) below, and a copepod luciferase activity:
(i) the amino acid sequence represented by SEQ ID NO: 37; and
(ii) an amino acid sequence represented by SEQ ID NO: 37 in which one or more amino acids are deleted in at least one of a region corresponding to positions 1-29 and a region corresponding to positions 217-221.

[2] The polypeptide according to Item [1] or [1-1] having any of amino acid sequences (iii) to (v) below;
(iii) an amino acid sequence represented by any of SEQ ID NOs: 11 to 17, and 24 to 36;
(iv) an amino acid sequence represented by any of SEQ ID NOs: 11 to 17, and 24 to 36 in which one or several amino acids are deleted, substituted, inserted, or added;
("several" means 1 to 20, preferably 1 to 10, more preferably 1 to 5 amino acids)
(v) an amino acid sequence having an identity of not less than 90% with any of amino acid sequences represented by SEQ ID NOs: 11 to 17 and 24 to 36.

[3] The polypeptide according to Item [1] or [1-1] having amino acid sequence (vi) or (vii) below,
(vi) the amino acid sequence represented by SEQ ID NO: 22; and
(vii) an amino acid sequence represented by SEQ ID NO: 22 in which one or more amino acids are deleted in at least one of a region corresponding to positions 1-29 and a region corresponding to positions 211-215.

[4] The polypeptide according to Item [1], wherein a region corresponding to positions 1-71 in the amino acid sequence represented by SEQ ID NO: 38 is the amino acid sequence represented by SEQ ID NO: 39.

[4-1] The polypeptide according to Item [1-1], wherein a region corresponding to positions 1-69 in the amino acid sequence represented by SEQ ID NO: 37 is the amino acid sequence represented by SEQ ID NO: 39.

[5] The polypeptide according to Item [1], wherein a region corresponding to positions 1-157 in the amino acid sequence represented by SEQ ID NO: 38 is the amino acid sequence represented by SEQ ID NO: 40.

[5-1] The polypeptide according to Item [1-1], wherein a region corresponding to positions 1-155 in the amino acid sequence represented by SEQ ID NO: 37 is the amino acid sequence represented by SEQ ID NO: 40.

[6] The polypeptide according to Item [1], wherein a region corresponding to positions 20-31 in the amino acid sequence represented by SEQ ID NO: 38 is an antibody recognition site.

[6-1] The polypeptide according to Item [1-1], wherein a region corresponding to positions 20-29 in the amino acid sequence represented by SEQ ID NO: 37 is an antibody recognition site.

[7] A nucleic acid encoding the polypeptide according to any one of Items [1] to [6-1].

[8] An expression vector in which the nucleic acid according to Item [7] is inserted in a manner such that the nucleic acid can be expressed.

[9] A transformed cell in which the nucleic acid according to Item [7] is introduced in a manner such that the nucleic acid can be expressed.

[10] A reporter protein to be used for a reporter assay method, the reporter protein comprising the polypeptide according to any one of Items [1] to [6-1].

[11] A luminescent fusion protein comprising a fusion protein containing the reporter protein according to Item [10], and a target protein or a peptide that recognizes a target protein.

[12] The luminescent fusion protein according to Item [11], wherein a membrane localization signal (MLS) is attached to the C-terminus of the reporter protein, and a target polypeptide is inserted between them as a cargo.

[13] The luminescent fusion protein according to Item [12], wherein the target polypeptide is a fluorescent protein or a luciferase.

[14] The luminescent fusion protein according to Item [12], wherein the target polypeptide is a polypeptide that changes the form in the plasma membrane, or a polypeptide having an amino acid sequence recognizable by the polypeptide that changes the form in the plasma membrane.

[15] An expression vector comprising a reporter gene encoding the luminescent fusion protein according to any one of Items [11] to [14].

[16] A transformed cell in which the expression vector according to Item [15] is introduced.

[17] A reporter assay method for assaying expression position, expression timing, or expression amount upon expression of a target gene in a cell in response to external stimulus, the method using the transformed cell according to Item [16].

[18] The assay method according to Item [17], wherein the assay is a reporter-gene assay or a two-hybrid assay.

[19] A bioluminescent probe for measuring the ligand activity of a ligand-binding protein, the bioluminescent probe comprising a fusion protein containing the reporter protein according to Item [10] bisected into an N-terminal side and a C-terminal side, a ligand-binding target protein, and a polypeptide that recognizes a change in steric structure upon binding of a ligand to the target protein.

[20] An expression vector for measuring the ligand activity of a ligand-binding protein, wherein a nucleic acid encoding the bioluminescent probe according to Item [19] is controlled by a control sequence that enables the nucleic acid to be expressed in a cell.

[21] A transformed cell in which the expression vector according to Item [20] is introduced.

[22] The transformed cell according to Item [16], wherein the transformed cell is a stem cell.

[23] A method for detecting the ligand activity of a ligand-binding protein in a test cell, the method using the expression vector according to Item [20].

[24] A bioluminescence imaging method comprising observing the ligand activity of a ligand-binding protein in a test cell using the expression vector according to Item [20].

Further, in the present invention, in order to provide a bioluminescence reaction buffer for enabling a highly sensitive bioassay even when the luminescence is measured directly from ligand stimulation, a suitable combination of a cell lysis solution for cell lysis and a reaction solution for luminescence measurement was examined. The results of the examination revealed that by using a bioluminescence reaction buffer that contains a Tris-buffer and an HBSS buffer as basic buffers, and NP-40 and TW80 as surfactants, it became possible to perform luminescence measurement directly from ligand stimulation during a bioluminescence bioassay, without requiring a lysis step. Further, by adding PEG or like polymers, metal ion, sugar component, halogen ion, and the like, the sensitivity of the bioassay was further increased.

In the present invention, first, the degree of contribution of each additive (heavy-metal ion, halogen ion, polymer additives, polyol, glycol, etc.) of the reaction solutions that have hitherto been used for bioassays was examined. Further, the performances of cell lysis agents (SDS, NP-40, TW80, Triton, etc.) were also examined. This study found some additives that contribute to an increase in bioassay performance, as well as their exemplary effective concentrations. Further, the results of an examination of a combination of a cell lysis solution and a reaction solution for luminescence measurement, which have hitherto been used respectively in the cell lysis step (Step 1) and the assay step (Step 2), revealed that by using a bioluminescence reaction buffer containing a Tris-buffer and an HBSS buffer as basic buffers, and NP-40 and TW80 as surfactants, the cell lysis step can be omitted. With this finding, the present invention succeeded in providing a reaction buffer for biolumines- cence bioassay that enables luminescence measurement directly from ligand stimulation.

By referring to the results of this examination of the additives to be used for bioassays, the inventors completed the present invention, which relates to a reaction buffer for bioluminescence bioassay, and a bioluminescence bioassay method using the reaction buffer.

The processes to complete the present invention are specifically described below.

Heretofore, bioassays have been performed separately using a "cell lysis buffer," a "wash buffer," and an "assay buffer." Therefore, the first example of the present invention examined the optimal compatibility of a cell lysis buffer with an assay buffer (Example 2-1). A comparison between some samples in terms of luminescence intensity and stability confirmed that, aside from the Promega buffer, C3 cell lysis buffer provides a buffer condition suitable for the artificial luciferase (ALuc). C3 buffer is based on a Tris-HCl buffer, and contains NP-40, sodium azide, $MgCl_2$, and NaCl. Further, it was confirmed that HESS or TE buffer (polyethylene glycol having a molecular weight of 400 (PEG 400) is added) is suitable as an assay buffer to be combined with C3 buffer (FIGS. 23A and 23B). Thus, on the assumption that C3 buffer is selected as the basic buffer, a combination of other buffer components was considered. In this consideration, the suitability of the combination with HESS buffer or TE-PEG was taken into account.

Although the present invention relates to all luminescent enzymes, the above artificial luminescent enzyme (ALuc), which has a high luminescence intensity and is continually observable, was mainly used in the examples to find an optimal combination of buffer components.

First, using an artificial luminescent enzyme (ALuc), a series of assay buffers were examined to find assay buffers that can be suitably combined with C3 cell lysis buffer (Example 2-2). The result of observation of the luminescence intensity and stability of the test buffers confirmed that PBS buffer, HBSS buffer, and TE-PEG buffer had good compatibility with C3 buffer (FIG. 24).

Next, by using a system having the most effective combination of C3 cell lysate and HBSS assay buffer, buffer additives were further examined (Example 2-3). Regarding the heavy metal to be added to the assay buffer to provide a luminescence effect, aluminum ion, copper ion, iron ion, Mo ion, zinc ion, and the like were confirmed to be effective additives (FIG. 25).

Further, the system having a combination of C3 cell lysate and HESS assay buffer was used in an actual detection experiment (androgen) using the integrated-molecule-format bioluminescent probe (ALuc) newly developed by the inventors, so as to examine the effect of the addition of polyethylene glycol (PEG) (Example 2-4). The results confirmed that the addition of PEG is effective, and also confirmed that the addition of PEG400 or PEG620 is particularly effective. It was also confirmed that the proportion of PEG is preferably about 1% (FIG. 26). Using the same system as that applied to the integrated-molecule-format bioluminescent probe (ALuc), the effect of addition of halogen ion to an assay buffer was further examined (Example 2-5). The examination confirmed that a certain effect can be expected from the addition of halogen ion. Among halogen ions, KI generally had a more significant effect than KBr, in particular, when the final concentration of KI was about 50 mM. For KBr, a significant effect was obtained when the final concentration was about 100 mM (FIG. 27). Using the same system, the effect of adding sugar to an assay buffer was examined (Example 2-6), with the results that a certain advantageous effect was obtained by the addition of a certain kind of sugar. The addition of sucrose or glucose generally provided a good effect. Although it is not a sugar, glycine also provided a good effect. Regarding the concentration, generally, a concentration of 2 mg/mL (final concentration) provided a good effect (FIG. 28).

As a result of the accumulation of basic study regarding the cell lysis buffer, the reaction buffer, and the additives, the development of a one-shot reaction solution that enables omission of time for cell lysis became more likely.

In order to avoid the cumbersome protocol of the known cumbersome bioassay that uses a cell lysis buffer and an assay buffer separately, a novel buffer was created using the additives found by the present invention.

Specifically, as shown in the compositions of C14 to C22 and FIGS. 29 and 30, a test was conducted by combining the cell lysis buffer and the assay buffer found in the above examples of the present invention. In particular, as shown in the results for C19-C22 (FIG. 29), using a combination of two or more surfactants was significantly effective. Further, as shown in the results for C23-C26 (FIG. 30), it was found that the effect becomes further significant with a certain mixing ratio of the buffers (i.e., a certain mixing ratio of the surfactant). With this contrivance, a novel luminescence reaction solution (this reaction solution will be called a one-shot buffer) that enables immediate luminescence measurement of the living cells without interfering with the luminescence reaction was completed.

The buffer of the present invention is characterized by its construction of the composition of the reaction solution that was made by sufficiently taking advantage of the characteristics of the individual surfactants, while compensating for their disadvantages.

The characteristics are more specifically explained below. First, according to the order of "the hydrophilic degree of the surfactants," which is TW20>Brij58>TW80>TX100>NP40, and the order of "the degree of the power of surfactant,"

which is NP40>TX100>Brij58>TW20>TW80, NP40 and TW80, which respectively have the highest and lowest interface activities, were mixed along with a small amount of SDS; this ensured a powerful lysis ability, while compensating for the disadvantages of the individual surfactants. As a result, a one-shot reaction solution that enables quick cell lysis while enabling luminescence measurement without interfering with the luminescence reaction was completed.

The effects of this one-shot reaction solution are specifically shown in Examples 2-9 and 2-10. A eukaryotic cell for expressing an integrated-molecule-format probe responsive to androgen was stimulated with steroid hormone or a chemical substance. Shortly after the one-shot buffer of the present invention was added to the cell, luminescence measurement was performed (Examples 2-9 and 2-10). The results revealed that the integrated-molecule-format probe having an androgen receptor was most strongly responsive to androgen (FIG. 31). Further, the integrated-molecule-format probe having an estrogen receptor was strongly responsive to an estrogen anticancer drug (OHT) (FIG. 32). These results clearly showed the advantageous effects of the one-shot buffer that enables immediate cell lysis while enabling luminescence measurement.

Based on such findings, the present invention was completed.

Specifically, the present invention also encompasses the following aspects.

[2-1] A bioluminescence reaction buffer to be used for performing a bioluminescence bioassay of living cells without a cell lysis step,
the bioluminescence reaction buffer comprising components (1) and (2) below;
(1) a basic buffer containing a Tris-buffer and an HBSS buffer; and
(2) a surfactant containing NP-40 and TW80.

[2-2] The bioluminescence reaction buffer according to Item [2-1] further comprising SDS as the (2) surfactant.

[2-3] The bioluminescence reaction buffer according to Item [2-1] or [2-2], further comprising at least one of additives (3) to (6) below;
(3) at least one kind of polymer compound selected from PEG and PPG;
(4) at least one polyvalent ion selected from Mg(II), Fe(III), Cu(II), Mo(VI) and Zn(II);
(5) at least one halogen ion selected from Br⁻ and I⁻; and (6) a polyol selected from sucrose, glucose, and glycine.

[2-4] The bioluminescence reaction buffer according to any one of Items [2-1] to [2-3], wherein the volume (v/v) % ratio of the Tris-buffer to the HBSS buffer in the (1) basic buffer is 20 to 50:50 to 20; and
the volume (v/v) % ratio of NP-40 to TW80 in the (2) surfactant is 1:1 to 10.

[2-5] The bioluminescence reaction buffer according to any one of Items [2-1] to [2-4], wherein the bioluminescence bioassay uses a bioluminescent probe responsive to a steroid hormone selected from androgen, estrogen, and stress hormone.

[2-6] A bioluminescence bioassay method, comprising suspending living cells in a bioluminescence reaction buffer without subjecting the living cells to a cell lysis step, and measuring the bioluminescence intensity in the resulting suspension, the method using a bioluminescence reaction buffer containing components (1) and (2) below;
(1) a basic buffer containing a Tris-buffer and an HBSS buffer; and
(2) a surfactant containing NP-40 and TW80.

[2-7] The bioluminescence bioassay method according to Item [2-6], wherein the bioassay method uses a bioluminescent probe responsive to a steroid hormone selected from androgen, estrogen, and stress hormone.

[2-8] A bioassay kit comprising the bioluminescence reaction buffer according to any one of Items [2-1] to [2-4].

Advantageous Effects of Invention

In the present invention, a group of novel artificial bioluminescent enzymes (ALuc) was established by using a method of extracting novel artificial bioluminescent enzyme sequences from many widely-known marine animal-derived luminescent enzyme sequences. Some of these enzymes had a super-high luminescence intensity, an increased wavelength, and superior heat resistance, and stably produced luminescence.

Further, various bioassay systems for "reporter assay" were constructed using the artificial bioluminescent enzymes (ALuc) of the present invention. As a result, upon the application as a luminescence fusion protein (luminescent capsule) fused with a membrane localization signal peptide, or a bioluminescent enzyme probe, a high sensing ability with respect to chemical substances or hormones was confirmed with a sensitivity higher than ever before. Thus, Additionally, by using ALucas a component of known luminescent enzymes that have hitherto been used in reporter-gene assay, yeast two-hybrid assay, mammalian two-hybrid assay, protein splicing assay (PSA), protein complementation assay (PCA), circular permutation assay, and bioluminescence resonance energy transfer (BRET) assay, which have been widely performed, it becomes possible to produce a luminescent probe having a high luminescence intensity and stability, thereby exponentially improving the measurement performance during these assays.

Further, the present invention also provides an optimal one-shot reaction solution for bioassay that does not require time for cell lysis, and ensures high stability and sensitivity.

With such an optimal bioassay reaction solution, the background light during the assay can be suppressed; thus, an increase in signal intensity and an increase in luminescence intensity can be expected. Further, since the experiment step can be simplified or omitted, the time and labor can be reduced. This contributes to improvement in S/N ratio, improvement in reproducibility, and reduction in cost in the bioassays.

BRIEF DESCRIPTION OF DRAWINGS

FIG. 1A Determination of amino acid sequences of novel artificial bioluminescent enzymes by dividing each of the amino acid sequences of bioluminescent enzymes obtained from a public database (NCBI) into a top portion, a first portion, and a second portion, and aligning the first portions and second portions based on the amino acid similarity, thereby increasing the similarity. The dotted-outline box denotes the template of the novel artificial bioluminescent enzymes. The enzyme active site is present twice in the lower region. The arrows indicate the selection of amino acids in view of increase in homology.

FIG. 1B(1) Determination of N-terminus (top portion) of the artificial bioluminescent enzyme. Candidate amino acids for composing a novel sequence were selected based on public amino acid sequence prediction software (SORTII) and the sequences of known luminescent enzymes.

FIG. 1B(2) Determination of C-terminus (top portion) of the artificial bioluminescent enzyme FIG. 1C An example of a sequence of the artificial bioluminescent enzyme of the present invention. In the figure, "x" represents any amino acid. The lower case "y" represents a hydrophobic amino acid. "z" represents a hydrophilic amino acid.

FIG. 1D An example of a sequence of the artificial bioluminescent enzyme of the present invention. "AlucCM" denotes the amino acid sequence represented by SEQ ID NO: 37. In the figure, "x" represents any amino acid (or blank). "o" represents a hydrophobic amino acid, "j" represents a hydrophilic amino acid, "." represents a low-molecular-weight aliphatic amino acid, "@" represents a high-molecular-weight aliphatic amino acid, "+" represents a positively charged amino acid, and "−" represents a negatively charged amino acid.

FIG. 1E An example of a sequence of the artificial bioluminescent enzyme of the present invention. "ALucCM" denotes an amino acid sequence represented by SEQ ID NO: 38. In the figure, "x" represents any amino acid (or blank). "o" represents a hydrophobic amino acid, "j" represents a hydrophilic amino acid, "." represents a low-molecular-weight aliphatic amino acid, "@" represents a high-molecular-weight aliphatic amino acid, "+" represents a positively charged amino acid, and "−" represents a negatively charged amino acid.

The luminescence reaction characteristics of the functional artificial bioluminescent enzymes established in the example (FIG. 21) were compared. The results revealed that ALuc33, ALuc34, etc., had relatively high luminescence intensity, and that the luminescence intensity gradually increased after the introduction of the substrate, and reached its highest value within 6 to 12 minutes.

Figure 23:
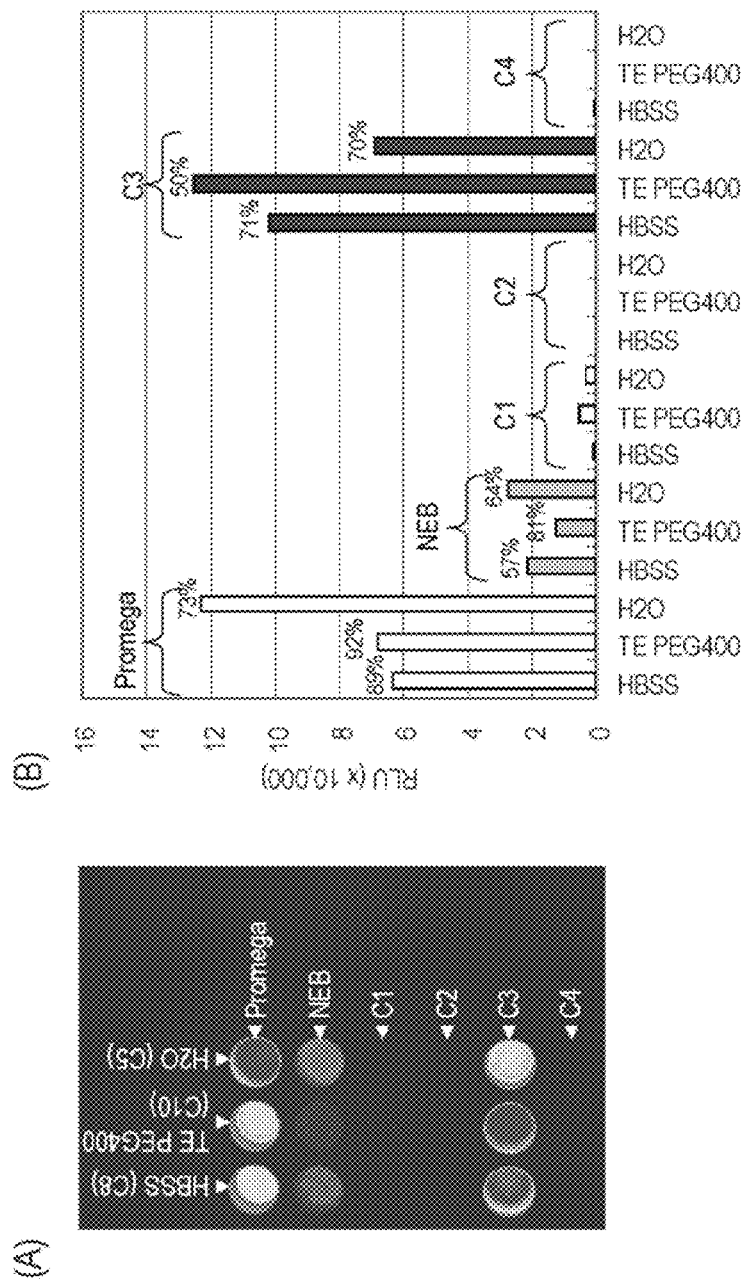

FIG. 23 Examination of an optimal combination of a cell lysis buffer and an assay buffer.
(A) An image showing a comparison of luminescence values of different buffer combinations. The image shows that the combination of lysis using a C3 buffer and an assay using an HBSS or TE buffer was most effective.
(B) A graph showing a comparison of luminescence values of different buffer combinations.

Figure 24:
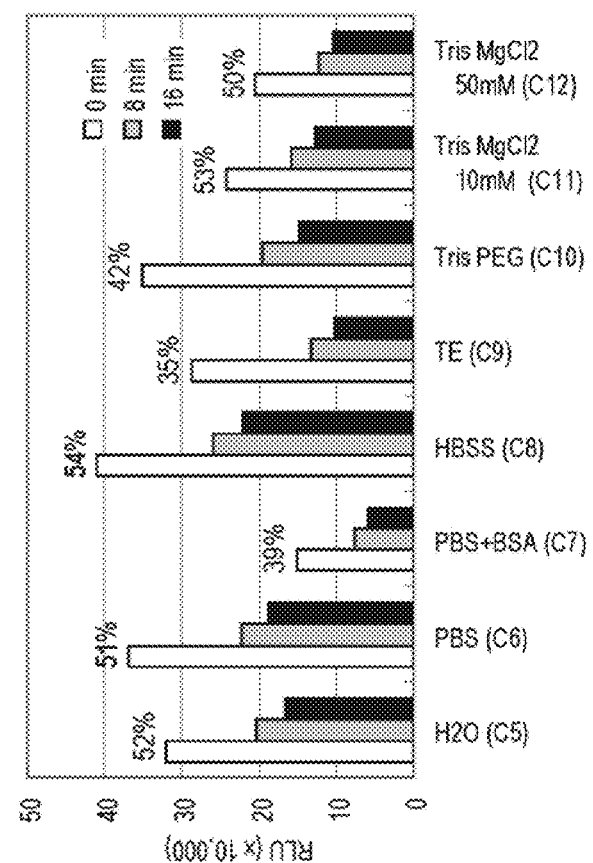
Figure 24:
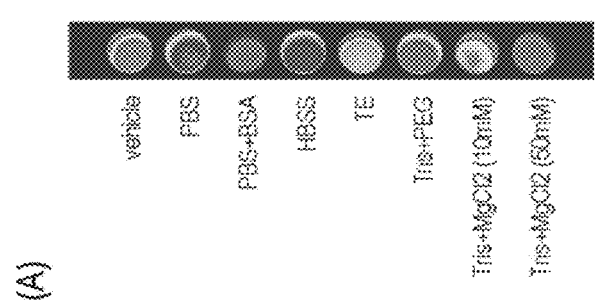

FIG. 24 Consideration of a combination of a C3 cell lysis buffer and a series of assay buffers.
(A) An image showing a comparison of luminescence intensity for different assay buffers.
(B) A graph showing a comparison of luminescence intensity of different assay buffers.

Among assay buffers, PBS buffer, HBSS buffer, and TE-PEG buffer had a good compatibility with C3. The percentages shown above the bars denote the residual luminescence intensity after 8 minutes, relative to the original luminescence intensity (100%).

Figure 25:
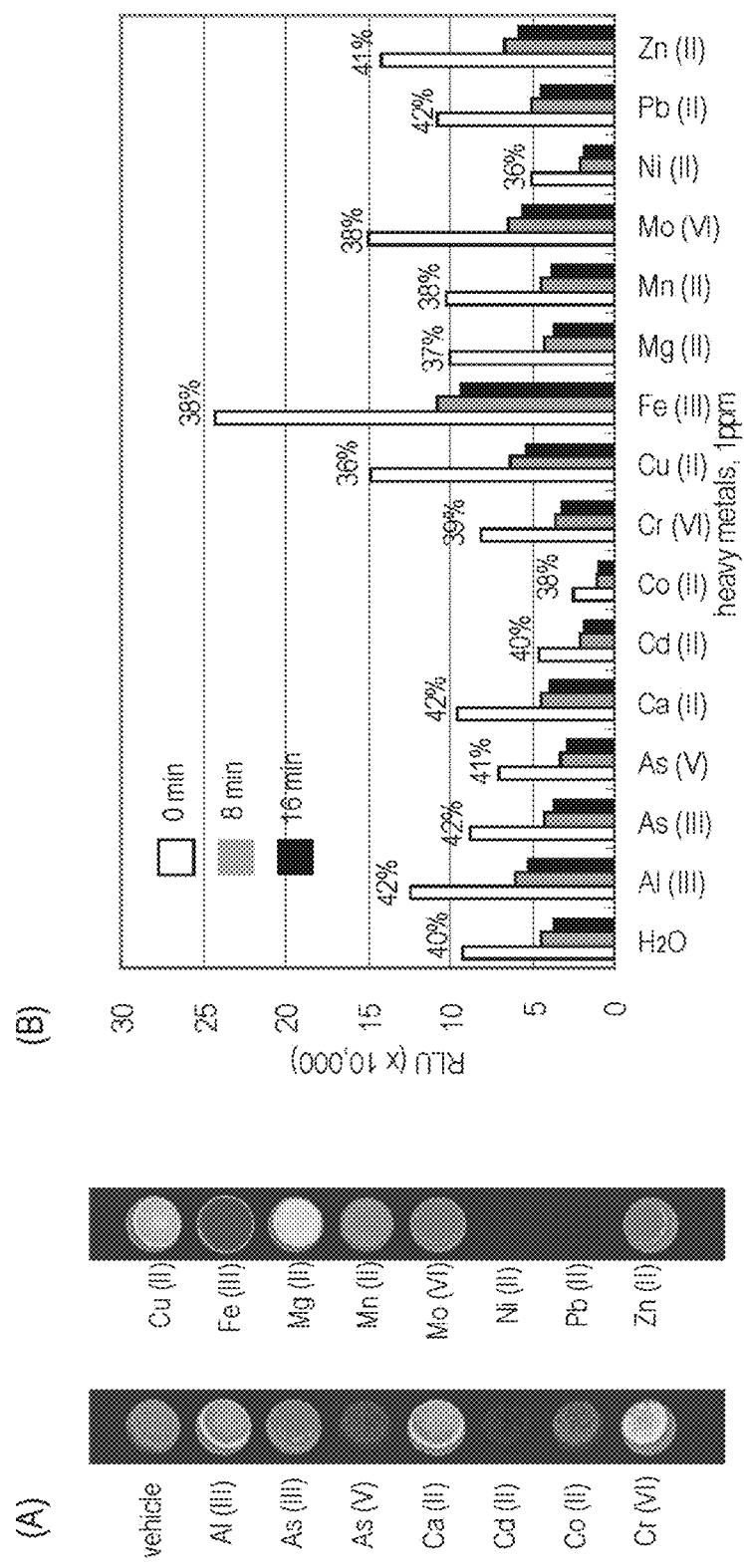

FIG. 25 Comparison in luminescence effect by addition of heavy-metal ion as a buffer additive.
(A) Images of luminescence intensity obtained by addition of heavy metals.
(B) A graph showing luminescence intensity obtained by addition of heavy metals.

Aluminum ion, copper ion, iron ion, Mo ion, and zinc ion were found to be effective as additives of assay buffer. The percentages shown above the bars denote the residual luminescence intensity after 8 minutes, relative to the original luminescence intensity (100%)

Figure 26:
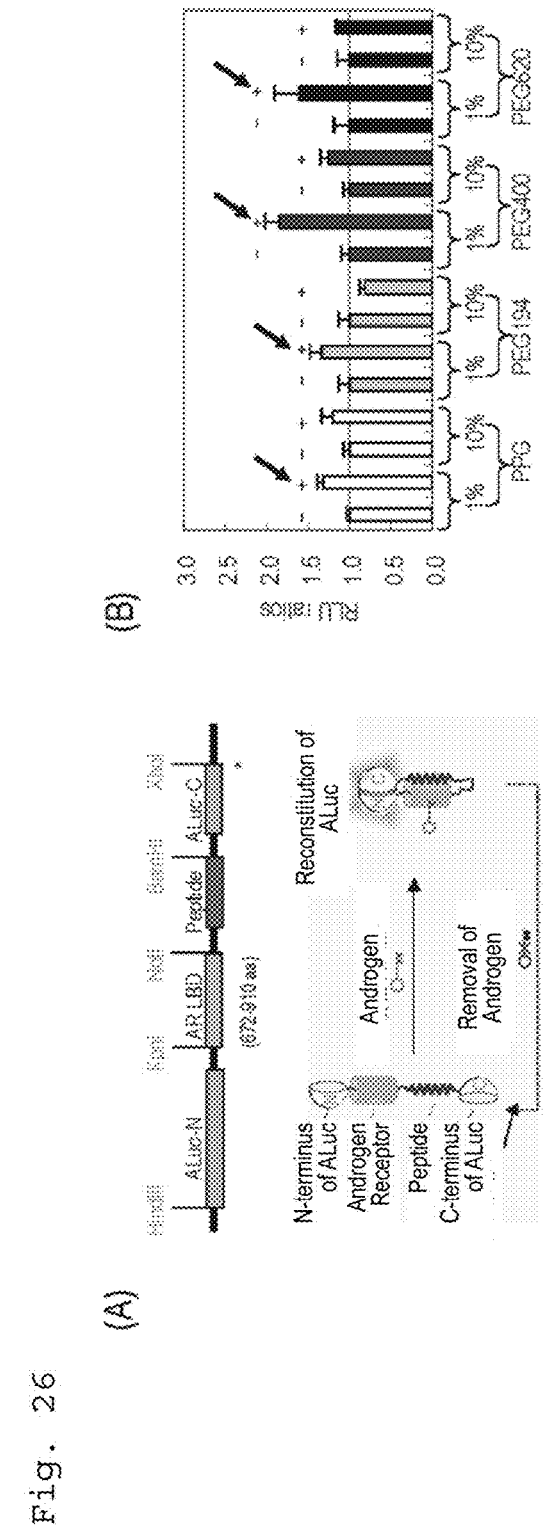

FIG. 26 Comparison in effect of addition of polyethylene glycol (PEG) in a luminescence reaction using integrated-molecule-format bioluminescent probe.
(A) The molecular structure and the working mechanism of an integrated-molecule-format probe used in the present example.
(B) Comparison in hormone recognition ability with the use of a buffer containing PEG.

The S/N ratio was higher in the case using a buffer containing 1% PEG than in other cases. The addition of polyethylene glycol mw. 400 (PEG 400) was particularly effective. The symbols "−" and "+" above the bars denote the presence or absence of androgen (DHT) in the measurement.

Figure 27:
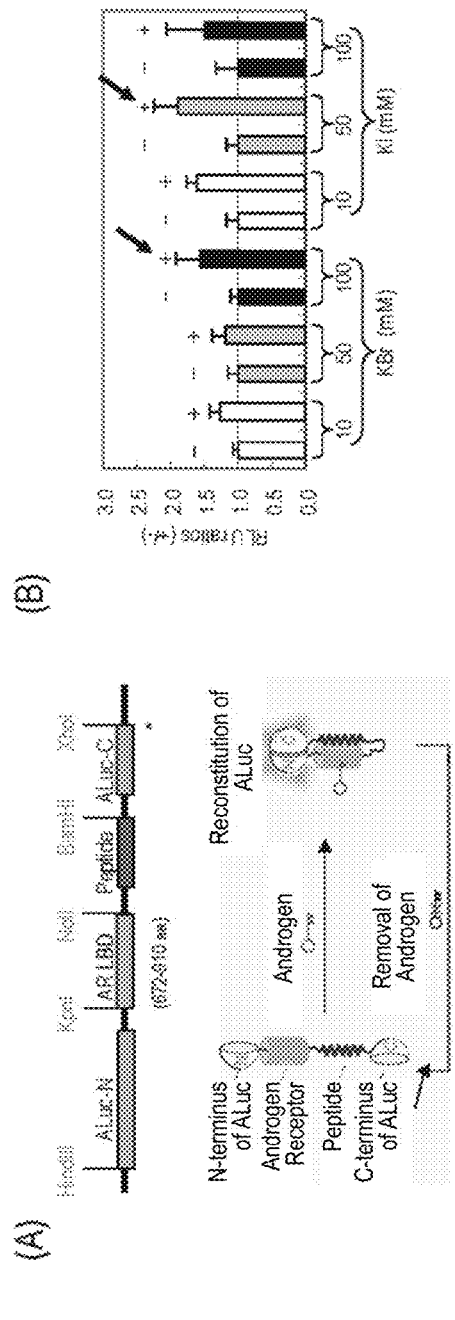

FIG. 27 Comparison in halogen ion addition effect in a luminescence reaction using an integrated-molecule-format bioluminescent probe.
(A) The molecular structure and the working mechanism of an integrated-molecule-format probe used in the present example.
(B) A graph showing luminescence intensity obtained by halogen ion addition. A high S/N ratio was obtained by addition of $I^-$ ion. The symbols "−" and "+" above the bars denote the presence or absence of androgen (DHT) in the measurement.

Figure 28:
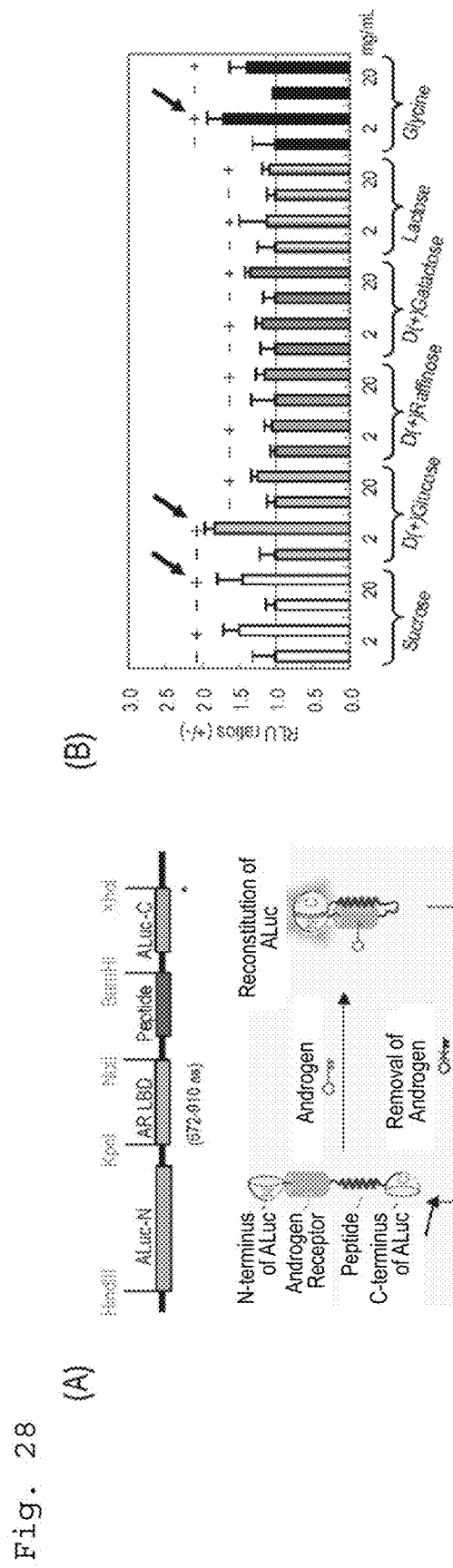

FIG. 28 Comparison in polysaccharide addition effect in a luminescence reaction using an integrated-molecule-format bioluminescent probe.
(A) The molecular structure and the working mechanism of an integrated-molecule-format probe used in the present example.
(B) A graph showing luminescence intensity obtained by addition of polysaccharide.

Additions of glucose, sucrose, and glycine were found to be effective. The symbols "−" and "+" above the bars denote the presence or absence of androgen (DHT) in the measurement.

Figure 29:
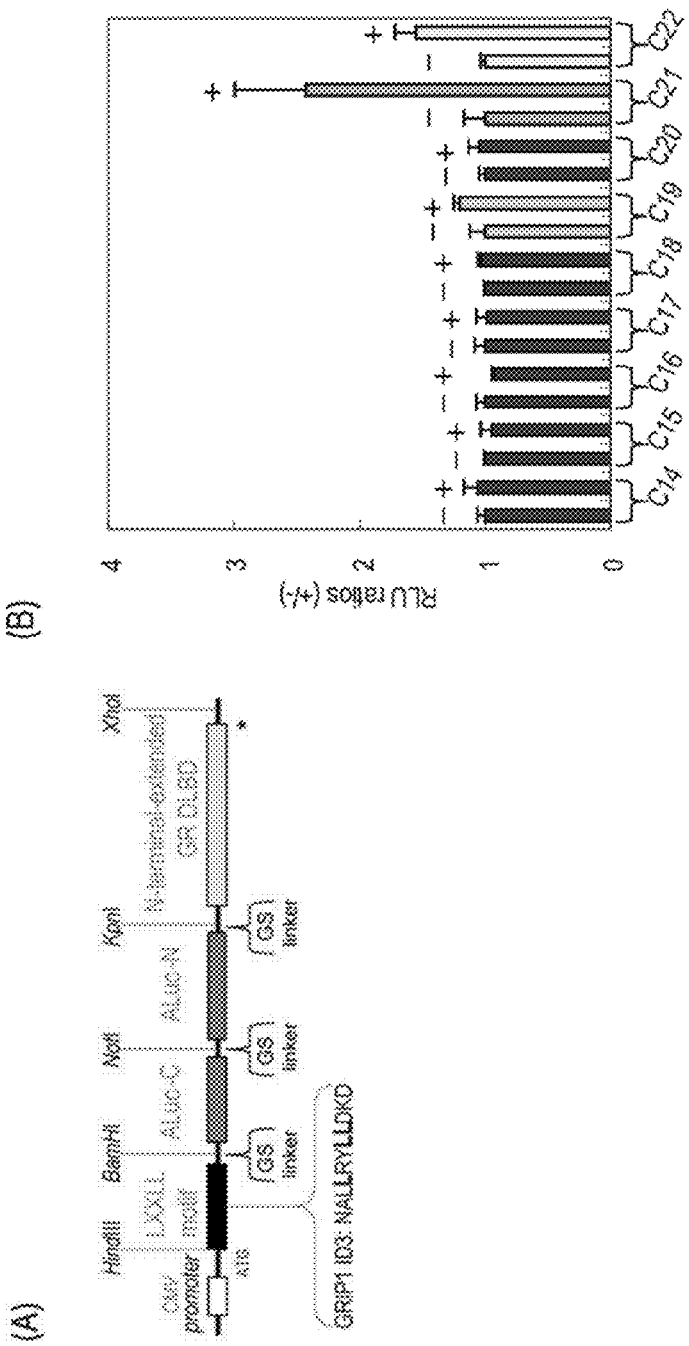

FIG. 29 Experiment for confirming the performance of one-shot buffer.
(A) Molecular structure of cSimgr8 probe. ALuc represents an artificial bioluminescent enzyme (artificial luciferase) that we established. GR LBD represents a stress hormone receptor.
(B) After stimulation of COS-7 cells including pcSimgr8 vector for 20 minutes in the presence or absence of a stress hormone, the luminescence intensity was measured using each one-shot buffer (C14-22). RLU ratio (+/−) denotes a luminescence intensity ratio in the presence of stimulation, compared with that in the absence of stimulation. The symbols "−" and "+" above the bars denote the presence or absence of androgen (DHT) in the measurement.

Figure 30:
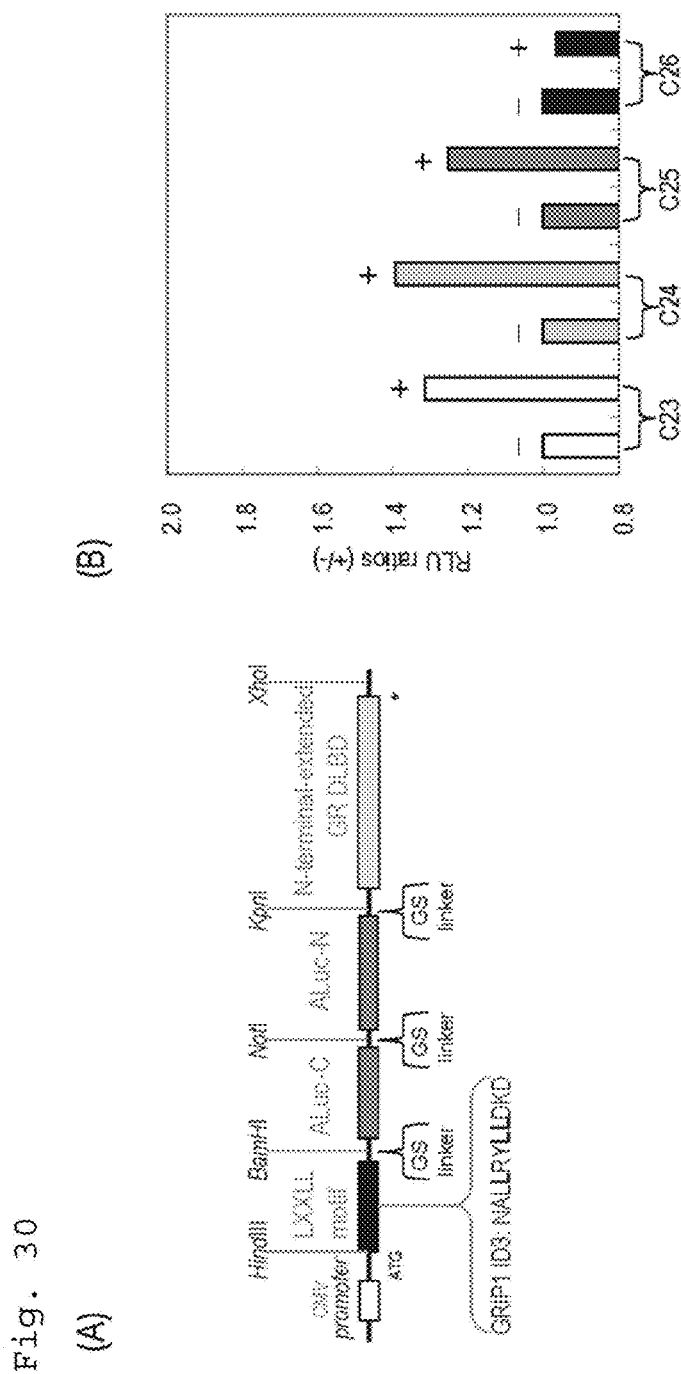

FIG. 30 Experiment for confirming the performance of one-shot buffer.
(A) Molecular structure of cSimgr8 probe ALuc represents an artificial bioluminescent enzyme (artificial luciferase) that we established. GR LBD represents a stress hormone receptor. After stimulating COS-7 cells containing (B) pcSimgr8 vector for 20 minutes in the presence and absence of stress hormone, luminescence intensity was measured using each one-shot buffer (C23-26). RLU ratio (+/−) denotes a luminescence intensity ratio in the presence of stimulation, compared with that in the absence of stimulation. The symbols "−" and "+" above the bars denote the presence or absence of androgen (DHT) in the measurement.

Figure 31:
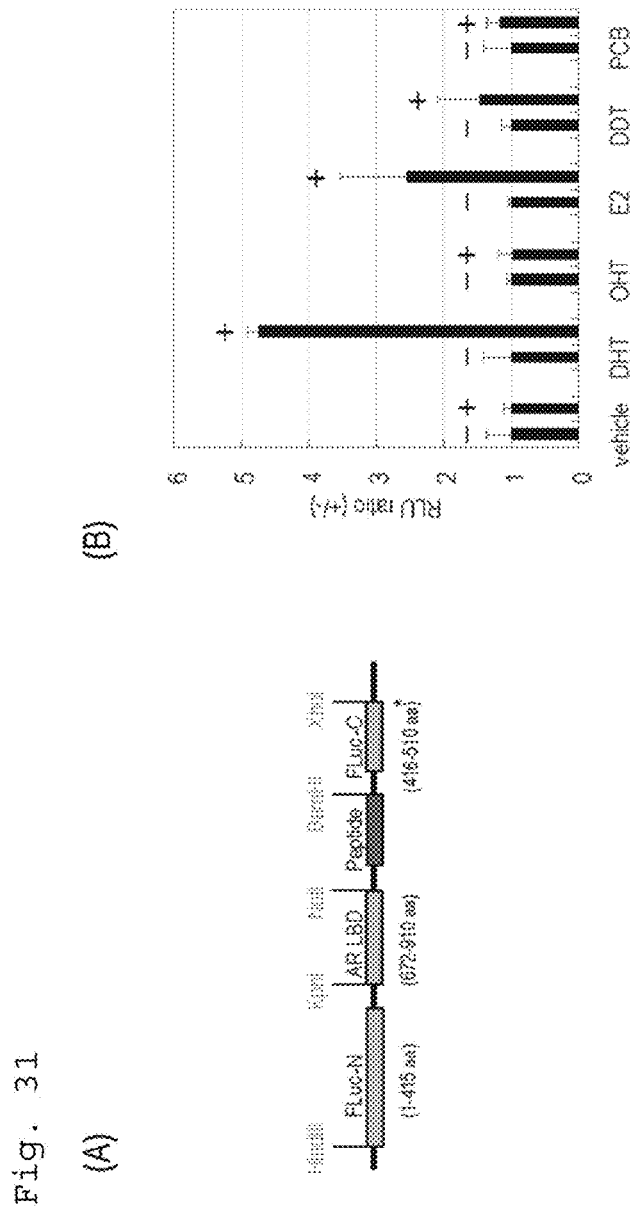

FIG. 31 Experiment for confirming the performance of one-shot buffer.
(A) Molecular structure of Leu-rich probe. AR LBD represents a androgen receptor (androgen receptor ligand-binding domain). FLuc represents firefly luciferase.
(B) Cells containing pLeu-rich vector were stimulated with DHT, OHT, $E_2$, DDT, and PCB for 20 minutes, and compared with the control (0.1% DMSO) stimulation. The results showed that the luminescence response was high with respect to androgen. The symbols "−" and "+" above the bars denote the presence or absence of androgen (DHT) in the measurement.

Figure 32:
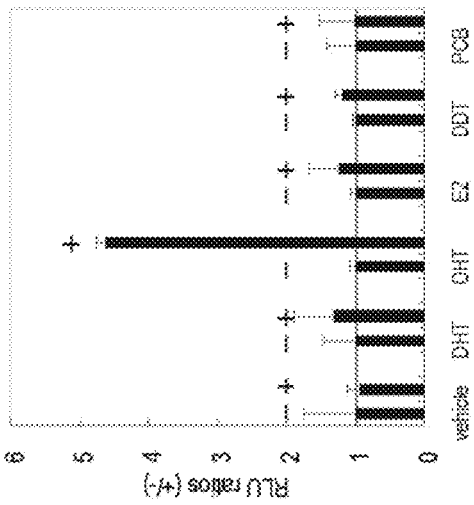
Figure 32:
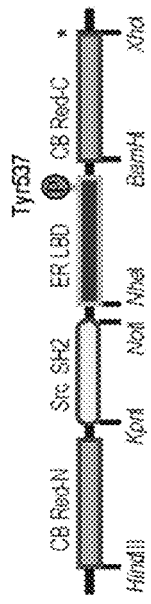

FIG. 32 Experiment for confirming the performance of one-shot buffer.
(A) Molecular structure of Simer-r2 probe ER LBD represents a estrogen receptor (estrogen receptor ligand-binding domain). CB Red represents a red luminescent enzyme originating from click beetle.
(B) Cells containing pSimer-r2 vector were stimulated with DHT, OHT, $E_2$, DDT, and PCB for 20 minutes, and compared with the control (0.1% DMSO) stimulation. The results showed that the luminescence response was high with respect to an anti-breast cancer drug (OHT). The symbols "−" and "+" above the bars denote the presence or absence of androgen (DHT) in the measurement.

[I] ARTIFICIAL BIOLUMINESCENT ENZYME

1. Artificial Luciferases (ALucs) of the Present Invention (1-1) Copepod Luciferase:

Regarding luminescent marine animals, it is known that marine animals derived from *Metridia okhotensis, Pleuromamma abdominalis, Lucicutia ovaliformis, Heterorhabdus tanneri, Heterostylites major, Gaussia princeps, Renilla reniformis, Metridia pacifica, Lucicutia grandis, Lucicutia bicornuta, Pleuromamma xiphias, Pleuromamma scutullata, Haloptilus pseudooxycephalus, Candacia longimana, Candacia columbiae, Candacia bipinnata, Calanus jashnovi, Neocalanus cristatus, Neocalanus flemingeri, Neocalanus plumchrus, Scaphocalanus magnus, Spinocalanus spinipes, Euchaeta marina, Undeuchaeta plumose, Undeuchaeta major, Xanthocalanus kurilensis, Scaphocalanus magnus Gaidius variabilis, Euchirella amoena, Cypridina (Cypridina noctiluca;* CLuc), *obelin, aqualine,* or *Oplophorus* produce luciferase.

In the present invention, "copepod luciferase" indicates, among luminescent marine animals, luciferase produced by small crustaceans called copepods that live as luminescent plankton. Specific examples of "copepod luciferase" include MoLuc1, MoLuc2, PaLuc1, PaLuc2, LoLuc, HtLuc1, HtLuc2, HmLuc1, HmLuc2, *Gaussia* luciferase (GLuc), *Renilla* luciferase (RLuc), *Metridia* luciferase (MLuc, MpLuc1, MpLuc2), *Cypridina noctiluca* luciferase (CLuc), and the like. Regarding the substrate specificity, "copepod luciferase" specifically oxidizes "coelenterazine." "Copepod luciferase" generally has an enzymatic property of catalyzing luminescent reaction under a deep-sea environment, i.e., an optimum pH of about 7.5 to 8 and an optimum temperature of about 4 to 10° C.; however, it also catalyzes luminescence under various conditions other than the above. Hereinafter, "copepod luciferases" refers to luciferases sharing common enzyme activity and structural characteristics with luciferases originating from known copepods. Specifically, "copepod luciferases" denotes luciferases having an optimum pH of about 5 to 8 and an optimum temperature of about 4 to 25° C., and an enzymatic activity that catalyzes luminescent reaction using "coelenterazine" as a substrate. The luciferases have two enzymatic activity domains and a secretion signal at their N-terminus, and a molecular weight of about 20 kD (18-28 kD), which is the smallest in the luminescent enzymes. The amino acid sequence homology of "copepod luciferases" is not less than 50%, and the amino acid sequence structure, such as hydrophilic and hydrophobic patterns, and the position of the enzymatic activity region are similar. "Copepod luciferases" are luciferases having higher luminescence intensity than other marine organism-derived luciferases.

In the present specification, "coelenterazine" is not limited to native coelenterazine (native CTZ), but includes various derivatives of native coelenterazine. That is, "coelenterazine" can also be referred to as "coelenterazine-type." Specific examples of coelenterazine include native coelenterazine (Native CTZ), coelenterazine ip (CTZ ip), coelenterazine i (CTZ i), coelenterazine hcp (CTZ hcp), coelenterazine 400A (CTZ 400A), coelenterazine fcp (CTZ fcp), coelenterazine cp (CTZ cp), coelenterazine f (CTZ f), coelenterazine h (CTZ h), coelenterazine n (CTZ n), and the like.

(1-2) Artificial Luciferases (ALucs) of the Present Invention

Since the novel artificial luciferases (ALucs) of the present invention have been discovered based on the amino acid sequences of the "copepod luciferases," they have the basic enzyme properties of "copepod luciferases," such as the substrate specificity and suitable pH described above. The artificial luciferases of the present invention are also novel artificial luciferases having significantly excellent luminescence characteristics such as luminescence intensity, luminescence in a long wavelength, and luminescence stability.

Examples of the typical artificial luciferase (ALuc) of the present invention include ALuc10 (SEQ ID NO: 11), ALuc15 (SEQ ID NO: 12), ALuc16 (SEQ ID NO: 13), ALuc17 (SEQ ID NO: 24), ALuc18 (SEQ ID NO: 14), ALuc19 (SEQ ID NO: 25), ALuc21 (SEQ ID NO: 26), ALuc22 (SEQ ID NO: 15), ALuc23 (SEQ ID NO: 16), Luc24 (SEQ ID NO: 27), ALuc25 (SEQ ID NO: 17), ALuc26 (SEQ ID NO: 28), ALuc27 (SEQ ID NO: 29), ALuc28 (SEQ ID NO: 30), ALuc29 (SEQ ID NO: 31), ALuc30 (SEQ ID NO: 32), ALuc31 (SEQ ID NO: 33), ALuc32 (SEQ ID NO: 34), ALuc33 (SEQ ID NO: 35), and ALuc34 (SEQ ID NO: 36). The artificial luciferase (ALuc) of the present invention can be expressed as a polypeptide having an amino acid sequence of any one of Items (i) to (iii) below and copepod luciferase activity:

(i) an amino acid sequence represented by any of SEQ ID NOs: 11 to 17 and 24 to 36;
(ii) an amino acid sequence represented by any of SEQ ID NOs: 11 to 17 and 24 to 36 in which one or several amino acids are deleted, substituted, inserted, or added,
(herein "several" means 1 to 20, preferably 1 to 10, more preferably 1 to 5 amino acids);
(iii) an amino acid sequence having an identity of not less than 90% with any of amino acid sequences represented by SEQ ID NOs: 11 to 17 and 24 to 36.

For example, an amino acid sequence having an identity of not less than 95%, not less than 96%, not less than 97%, not less than 98%, not less than 99%, and not less than 99.5% is more preferable.

Figure 1A:
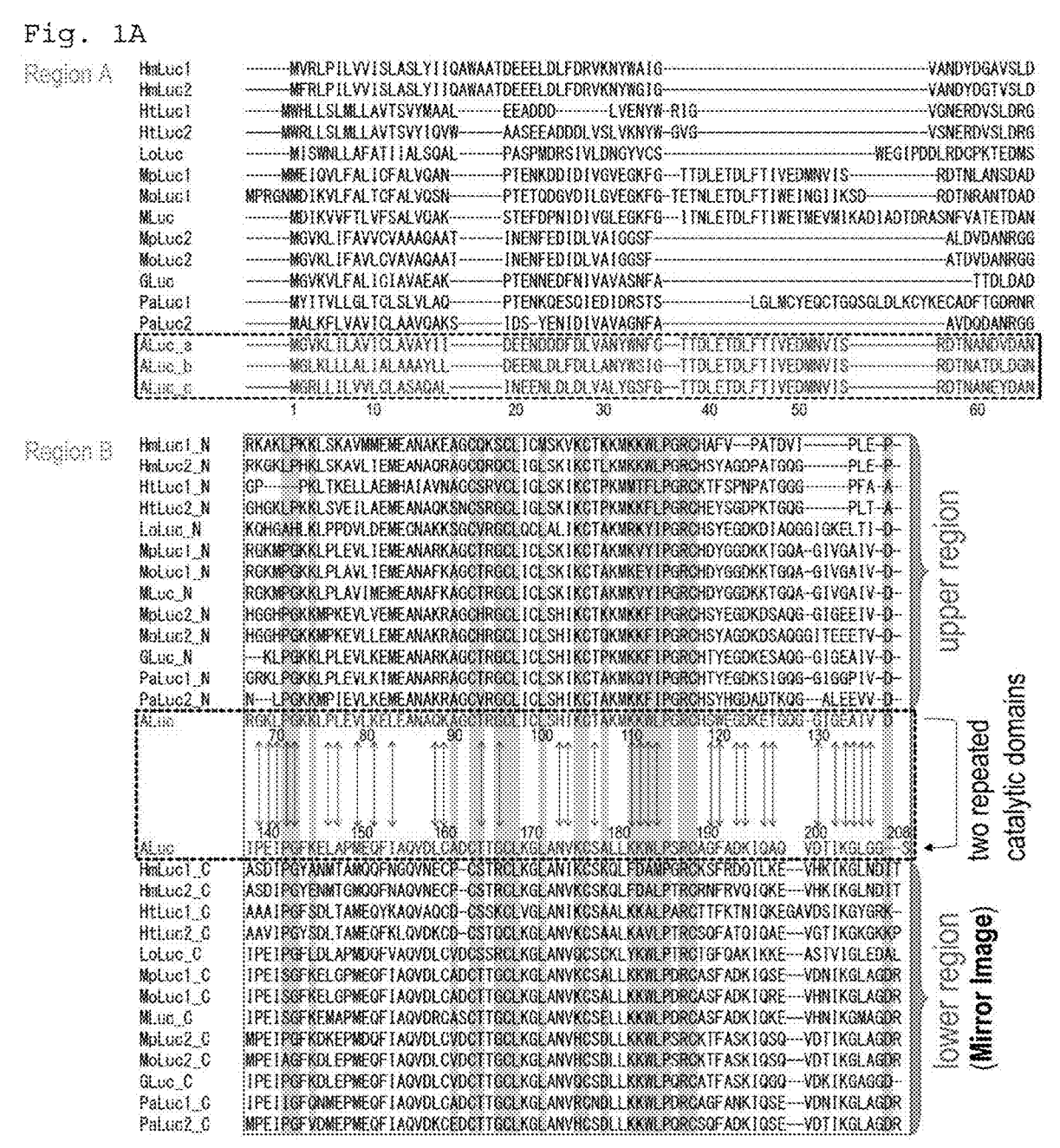
Figure 1B:
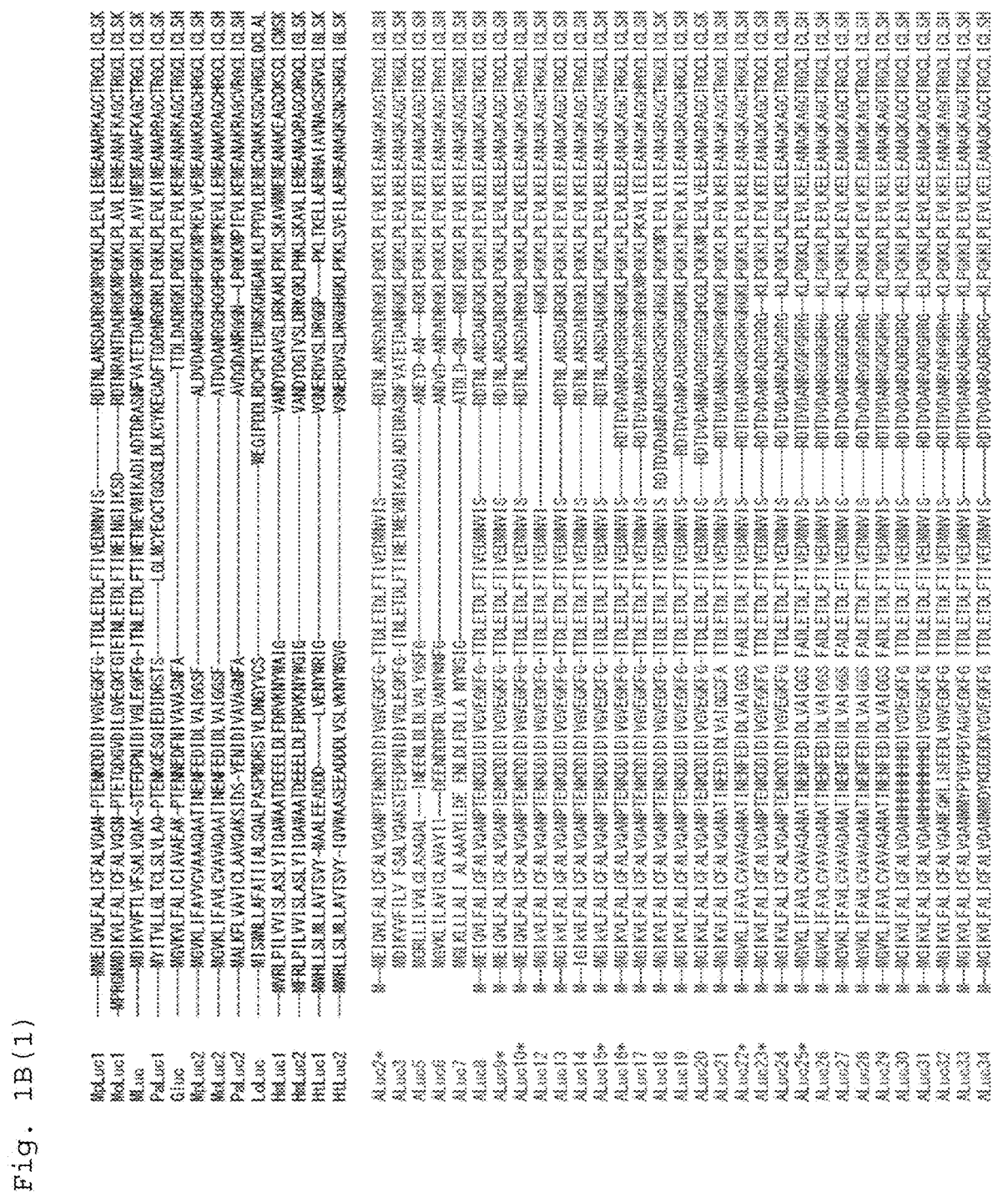
Figure 1B:
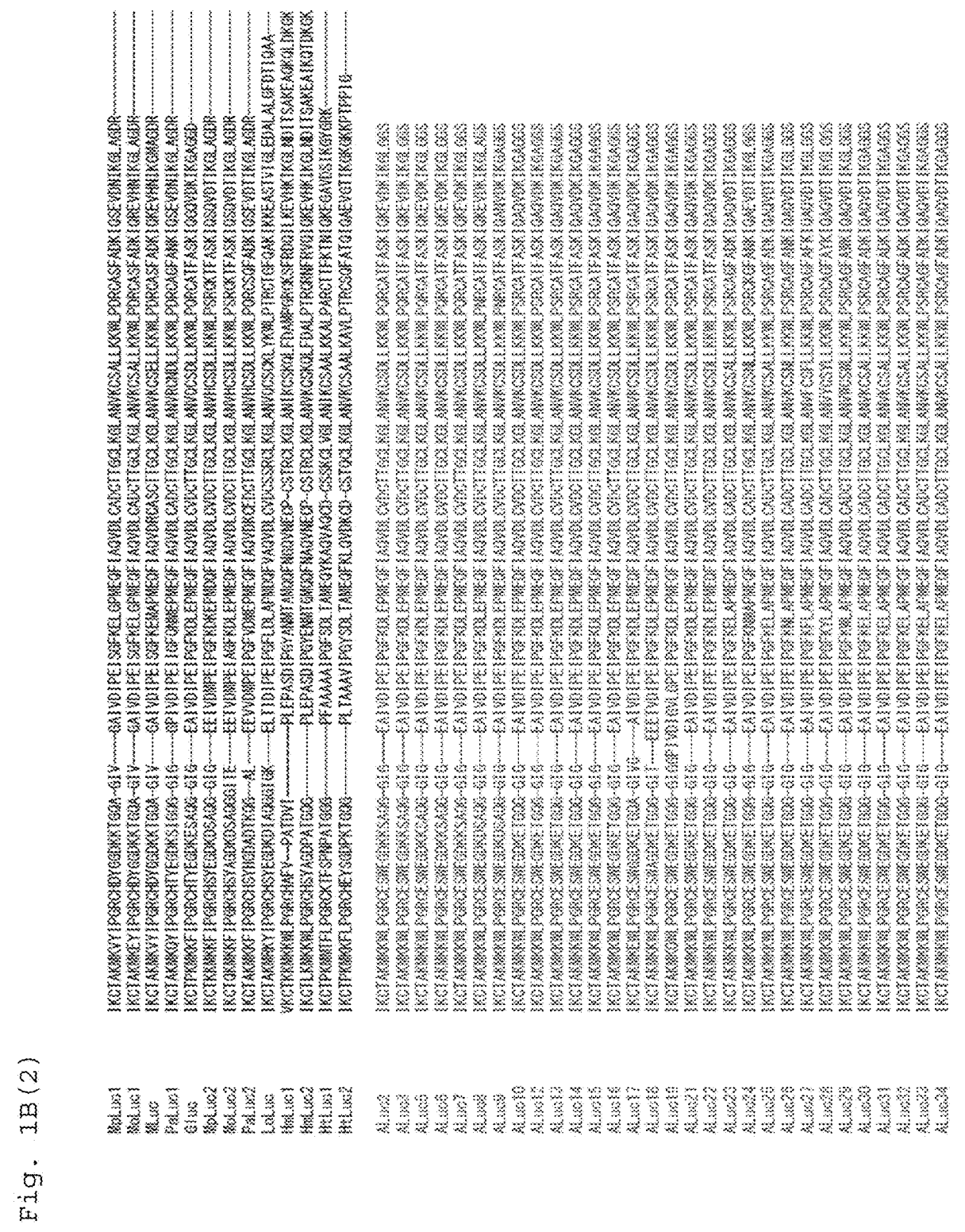

The amino acid sequences of the artificial luciferases (ALucs) of the present invention have common basic frame structures shown in FIG. 1C, FIG. 1D, and FIG. 1E. As long as the artificial luciferase has such a basic frame structure, an equivalent high performance copepod luciferase activity can be obtained even when amino acids at other positions are freely selected amino acids. Accordingly, the artificial luciferase (ALuc) of the present invention can be expressed as a polypeptide having an amino acid sequence of any one of Items (iv) to (vii) below and copepod luciferase activity:

(iv) the amino acid sequence represented by SEQ ID NO: 37;
(v) an amino acid sequence represented by SEQ ID NO: 37 in which one or more amino acids are deleted in at least one of a region corresponding to positions 1-29 and a region corresponding to positions 214-218;
(iv) the amino acid sequence represented by SEQ ID NO: 38;
(v) an amino acid sequence represented by SEQ ID NO: 38 in which one or more amino acids are deleted in at least one of a region corresponding to positions 1-31 and a region corresponding to positions 217-221;
(vi) the amino acid sequence represented by SEQ ID NO: 22; or
(vii) an amino acid sequence represented by SEQ ID NO: 22 in which one or more amino acids are deleted in at least one of a region corresponding to positions 1-29 and a region corresponding to positions 211-215.

In the amino acid sequence represented by SEQ ID NO: 22, amino acids from positions 1-20 of the N-terminal side are secretion signals (secretion peptide; SP), and a peptide at positions 211-215 of the C-terminal side is a Glycine rich linker peptide (commonly known as a GS linker). Accordingly, part or all of the amino acids in these regions may be deleted. The same applies to positions 1-20 of the N-terminal side and positions 214 to 218 of the C-terminal side in the amino acid sequence represented by SEQ ID NO: 37, and positions 1-20 of the N-terminal side and positions 217-221 of the C-terminal side in the amino acid sequence represented by SEQ ID NO: 38. In copepod luciferases such as *Metridia pacifica* luciferase 1 (MpLuc1) and *Pleuromamma* luciferase, the secretion signals correspond to amino acids at positions 1-18 in *Metridia pacifica* luciferase 1 (MpLuc1), and correspond to amino acids at positions 1-19 in *Pleuromamma* luciferase. It is known that these amino acids may be deleted.

As proved in Example 1-21, etc., described below, the function of artificial bioluminescent enzyme is not significantly impaired even when position 20 to 29 in the amino acid sequence represented by SEQ ID NO: 22 (corresponding to a region of positions 20-29 in the amino acid sequence represented by SEQ ID No. 37, and a region of positions 20-31 in the amino acid sequence represented by SEQ ID NO: 38) are substituted with a functional amino acid sequence (e.g., antigen recognition site, affinity chromatography recognition site, or official signal). Accordingly, part or all of the amino acids in this region may be deleted.

In the amino acid sequences represented by SEQ ID NOs: 22, 37, and 28, amino acids represented by Xaa are explained in detail below.

Of the amino acids represented by Xaa in SEQ ID NO: 37, amino acids at positions 3, 20-27, 29, 30, 33, 35, 62-64, 67, 74, 75, 83, 84, 87, 88, 127, 137-145, 147, 156, 158, 185, 188, 199, and 203 may be any amino acids. Of these, amino acids at positions 74-75 and 137-140 may be deleted. Preferably, position 3 is E or G; positions 20-27 are PTENKDDI (SEQ ID NO: 41), ATINEEDI (SEQ ID NO: 42), ATINENFE (SEQ ID NO: 43), HHHHHHHH (SEQ ID NO: 44), EKLISEE (SEQ ID NO: 45), MMYPYDVP (SEQ ID NO: 46), or MMDYKDDD (SEQ ID NO: 47); position 29 is I, L, Y, or K; position 30 is V, D, or A; position 33 is E, G, or A; position 35 is K, S, or G; positions 62-64 are ANS or DAN; position 67 is D or G, positions 75-76 are GG or K (deletion of one residue), or may be deleted; positions 83-84 are LE, KA, or KE; positions 87-88 are KE, IE, LE, or KI; position 127 is E, G, or A; positions 137-145 are IGEA (deletion of four residues, SEQ ID NO: 48), IVGA (deletion of four residues, SEQ ID NO: 49), ITEEE (deletion of three residues, SEQ ID NO: 50), or IGGPIVD (SEQ ID NO: 51); position 147 is D or L; position 156 is D, E, N, F, Y, or W; position 158 is E or L; position 185 is K, F, Y, or W; position 188 is D, A, N, F, Y, or W; position 199 is A or K; and position 203 is S, D, N, F, Y, or W.

Amino acids at positions 13, 16, 36, 148, 171, and 215 are hydrophobic amino acids (for example, V, F, A, or L), and it is preferable that position 13 is V or F; position 16 is V or A; position 36 is F or G; position 148 is I or G; position 168 is V or A; and position 215 is A or L.

Amino acids at positions 5, 65, 73, 99, 117, and 211 are hydrophilic amino acids (for example, Q, K, D, R, H, E, or T), and it is preferable that position 5 is Q or K; position 65 is D or R; position 73 is K, H, R, or E; position 99 is T or H; position 117 is K, E, or Q; and position 211 is K or T.

Amino acids at positions 4, 6, 7, 10, 11, 15, 31, 32, 37-39, 61, 66, 72, 76, 81, 136, 157, and 200 are aliphatic amino acids, and it is preferable that positions 4, 6, 7, 10, 11, 15, 32, 61, 76, 81, and 157 are high molecular weight aliphatic amino acids (e.g., I, V, L, or M), and more preferably, position 4 is I or V; position 6 is V or L; and position 7 is L or I; position 10 is L or V; position 11 is I or L; position 15 is L or V; position 32 is I or V; position 61 is L or V; position 76 is L or M; position 81 is L or M; and position 157 is L or M. It is also preferable that positions 31, 34, 37-39, 66, 72, 136, and 200 are low molecular weight aliphatic amino acids (e.g., A, G, T, or L), and more preferably, position 31 is G, L, or A; position 34 is G or I; position 37 is G, A, S, or F; position 38 is T or F; position 39 is T or A; position 66 is A or G; position 72 is G or may be deleted; position 136 is G or A; and position 200 is T or G.

Amino acids at positions 70, 71, 95, and 108 are positively-charged amino acids (basic amino acids such as K, R or H), and it is preferable that positions 70 and 71 are each R, or may be deleted; position 95 is K or R; and position 108 is H or K.

Amino acids at positions 60 and 208 are negatively-charged amino acids (acidic amino acids such as N, D, Q, or E), and it is preferable that position 60 is N or D, and position 208 is Q or E.

Of the amino acids represented by Xaa in SEQ ID No. 38, amino acids at positions 3, 20-29, 31, 32, 35, 37, 64-66, 69, 76-77, 85-86, 89-90, 129, 140-144, 148-151, 159, 161, 188, 191, 202, and 206 may be any amino acids. Of these, amino acids at positions 22-23, 39-40, 76-77, 140, and 148-151 may be deleted. Preferably, position 3 is E or G; positions 20-29 are PTENKDDI (deletion of two residues, SEQ ID NO: 52), ATINEEDI (deletion of two residues, SEQ ID NO: 53), ATINENFEDI (SEQ ID NO: 54), HHHHHHHH (deletion of two residues, SEQ ID NO: 55), EKLISEE (deletion of two residues, SEQ ID NO: 56), MMYPYDVP (deletion of two residues, SEQ ID NO: 57), or MMDYKDDD (deletion of two residues, SEQ ID NO: 58); position 31 is I, L, Y, or K; position 32 is V or A; position 35 is E or G; position 37 is K or S; positions 64-66 are ANS or DAN; position 69 is D or G; positions 76-77 are GG or K (deletion of one residue), or may be deleted; positions 85-86 are LE, KA, or KE; positions 89-90 are KE, IE, LE, or RI; position 129 is E, G, or A; positions 140-144 are TEEET (SEQ ID NO: 59), GEAI (deletion of one residue, SEQ ID No. 60), or VGAI (deletion of one residue, SEQ ID NO: 61); positions 148-151 are GVLG (SEQ ID NO: 62), GEAI (deletion of one residue, SEQ ID NO: 60), or VGAI (deletion of one residue, SEQ ID NO: 61); positions 148-151 are GVLG (SEQ ID NO: 62) or I (deletion of three residues), or all may be deleted; position 159 is D, E, N, F, Y, or W; position 161 is E or L; position 188 is K, F, Y, or W; position 191 is D, A, N, F, Y, or W; position 202 is A or K; and position 206 is S, D, N, F, Y, or W.

Amino acids at positions 13, 16, 174, and 218 are hydrophobic amino acids (e.g., V, F, A, or L), and it is preferable that position 13 is V or F; position 16 is V or A; position 174 is V or A; and position 218 is A or L.

Amino acids at positions 5, 67, 75, 101, 119, and 214 are hydrophilic amino acids (e.g., Q, K, D, R, H, E, or T), and it is preferable that position 5 is Q or K; position 67 is D or R; position 75 is K, H, R, or E; position 101 is T or H; position 119 is K, E, or Q; and position 211 is K or T.

Amino acids at positions 4, 6, 7, 10, 11, 15, 33, 34, 39-41, 63, 68, 77, 78, 83, 138, 160, and 203 are aliphatic amino acids, and amino acids at positions 39, 40, and 70 may be deleted. It is preferable that positions 4, 6, 7, 10, 11, 15, 34, 63, 78, 83, and 160 are high molecular weight aliphatic amino acids (e.g., I, V, L, or M); however, they may be less-frequently occurring low molecular weight aliphatic amino acids. More preferably, position 4 is I or V; position 6 is V or L; position 7 is L or I; position 10 is L or V; position 11 is I or L; position 15 is L or V; position 34 is I or V;

position 63 is L or V; position 78 is L or M; position 83 is L or M; and position 160 is L or M. It is also preferable that positions 33, 39-41, 68, 74, 137, and 203 are low molecular weight aliphatic amino acids (e.g., A, G, or T); however, they may be less-frequently occurring high molecular weight aliphatic amino acids. More preferably, position 33 is G, L, or A; position 39 is G, A, S, or F, or may be deleted; position 40 is T or may be deleted; position 41 is T or A; position 68 is A or G; position 74 is G or may be deleted; position 137 is G or A; and position 203 is T or G.

Amino acids at positions 72, 73, 97, and 110 are positively-charged amino acids (basic amino acids such as K, R or H), and amino acids at positions 72 and 73 may be deleted. It is preferable that positions 72 and 73 are each R, or may be deleted; position 97 is K or R; and position 110 is H or K.

Amino acids at positions 62 and 211 are negatively-charged amino acids (acidic amino acids such as N, D, Q, or E), and it is preferable that position 62 is N or D, and position 211 is Q or E.

Of the amino acids represented by Xaa in SEQ ID NO: 22, amino acids at positions 3, 22, 26, 27, 30, 33, 35, 37-39, 62, 63, 67, 71-75, 87, 127, 138, 140-142, 155, 185, and 197 may be any amino acids. Of these, part or all of the amino acids at positions 71-75 and 140-142 may be deleted. Of hydrophilic amino acids, it is preferable that positions 3, 22, 27, 33, 127, 140, 141, and 155 are E; positions 26, 30, 62, 67, and 185 are D; positions 35 and 87 are K; position 37 is S; positions 38, 39, 138, 142, and 197 are T; position 63 is N; position 71 is R; and position 73 is D or H. Of hydrophobic amino acids, it is preferable that positions 3, 37, 67, 72, 74, 75, 138, and 197 are G; positions 22, 27, and 141 are I; position 30 is V; positions 33, 39, 62, 63, 127, 140, 155, and 185 are A; position 87 is L; and positions 26 and 38 are F.

Amino acids at positions 4, 6, 7, 10, 11, 13, 15, 16, 20, 31, 34, 36, 61, 66, 81, and 168 are hydrophobic amino acids, and it is preferable that position 4 is I or V; position 6 is V or L; position 7 is I or L; position 10 is V or L; position 11 is I or L; and position 13 is V or F; position 15 is V or L; position 16 is V or A; position 20 is A or P; position 31 is L or G; position 34 is I or G; position 36 is F or G; position 61 is V or L; position 66 is A or G; position 81 is L or M; and position 168 is V or A.

Amino acids at positions 5, 24, 25, 60, 64, 65, 70, 95, 108, 153, 200, and 208 are hydrophobic amino acids, and it is preferable that position 5 is Q or K; position 24 is K or E; position 25 is D or N; position 60 is D or N; position 64 is N or S; position 65 is D or R; position 70 is K or R; position 95 is K or R; position 108 is K or H; position 153 is E or D; position 200 is D or S; and position 208 is K, H, or T.

Typical examples of the amino acid sequence represented by SEQ ID NO: 22 include ALuc10, ALuc15, ALuc16, ALuc18, ALuc22, ALuc23, and ALuc25.

One embodiment of the artificial luciferase of the present invention includes the amino acid sequence represented by SEQ ID NO: 39 as the region corresponding to positions 1-71 in the amino acid sequence represented by SEQ ID NO: 38 (corresponding to the region of positions 1-69 in the amino acid sequence represented by SEQ ID NO: 37, and the region of positions 1-69 in the amino acid sequence represented by SEQ ID NO: 22). Typical examples include ALuc15, ALuc16, ALuc17, ALuc18, and ALuc24.

Another embodiment of the artificial luciferase of the present invention includes the amino acid sequence represented by SEQ ID NO: 40 as the region corresponding to positions 1-157 in the amino acid sequence represented by SEQ ID NO: 38 (corresponding to the region of positions 1-155 in the amino acid sequence represented by SEQ ID NO: 37, and the region of positions 1-152 in the amino acid sequence represented by SEQ ID NO: 22). Typical examples include ALuc22, ALuc25, ALuc26, ALuc27, ALuc28, and ALuc29.

Still another embodiment of the artificial luciferase of the present invention includes an antibody recognition site (epitope sequence) therein. "Antibody recognition site" or "epitope sequence" can also be referred to as "antigen site." Typical examples include ALuc30, ALuc31, ALuc32, and ALuc34.

Specifically, in the artificial luciferase having an antibody recognition site (epitope sequence) therein, a region corresponding to positions 20-31 in SEQ ID NO: 38 or a region corresponding to positions 20-31 in SEQ ID NO: 37 includes an antibody recognition site (epitope sequence). Preferable examples of the antibody recognition site (epitope sequence) include His-tag (HHHHHH) (SEQ ID NO: 5), FLAG-tag (DYKDDDDK) (SEQ ID NO: 6), Myc-tag (EQKLISEEDL) (SEQ ID NO: 7), and HA-tag (YPYDVPDYA) (SEQ ID NO: 8); however, they are not limited thereto.

In an example of the artificial luciferase having an His-tag therein, amino acids at positions 20-31 in SEQ ID NO: 38 or amino acids at positions 20-31 in SEQ ID NO: 37 are all H (His×8 sequence). Typical examples include ALuc30 and Aluc31.

In an example of the artificial luciferase having a c-Myc-tag therein, the sequence of the region corresponding to positions 20-31 in SEQ ID NO: 38 or the sequence of the region corresponding to 20 to 31 in SEQ ID NO: 37 is EQKLISEEDL (Myc-tag sequence, SEQ ID NO: 7). Typical examples include ALuc32.

In an example of the artificial luciferase having an HA-tag therein, amino acids at positions 20-31 in SEQ ID NO: 38 or amino acids at positions 20-31 in SEQ ID NO: 37 are YPYDVPDYA (HA-tag sequence, SEQ ID NO: 8). Typical examples include ALuc33.

In an example of the artificial luciferase having a FLAG-tag therein, amino acids at positions 20-31 in SEQ ID NO: 38 or amino acids at positions 20-31 in SEQ ID NO: 37 are DYKDDDDK (FLAG-tag sequence, SEQ ID NO: 6). Typical examples include ALuc34.

2. Establishment of Novel Artificial Luciferase (ALuc) of the Present Invention (2-1) Luminescence Characteristics Required for Novel Luciferase (ALuc) of the Present Invention Luminescence characteristics required for copepod luciferase include high luminescence intensity as well as a red-shifted luminescence spectrum, high luminescence stability, heat resistance, and salt tolerance. Since the shift of the luminescence spectrum to the long wavelength side enhances transmittance of luminescence through tissues such as skin tissues or organs, the red-shifted luminescence spectrum is one of the important luminescence characteristics of a reporter protein, which is used as a luminescence enzyme for bioassays or diagnostic probes. Further, because of strong bioluminescence intensity, an effect of detection in various bioassays, even when a small amount of luminescence molecules is used, is expected. Furthermore, when the temporal luminescence stability is ensured, luminescence signal reliability is enhanced, and a reduction in fading during molecular imaging is anticipated. Still further, because they have heat resistance and salt tolerance, luminescence signals are advantageously reliably ensured, even under various bioassay environments. In the comparison of the artificial luciferases (ALucs) of the present invention, the presence or absence of these characteristics is mainly compared to establish more excellent artificial luciferase (ALuc).
(2-2) Method for Establishing Novel Luciferase:

One of the conventional methods for establishing novel luciferase is a method in which mRNA is directly extracted from body fluids of various copepods, the mRNA is converted to DNA using a reverse transcriptase, and the DNA is inserted to an expression vector (e.g., pcDNA3.1 (+)) for expression, followed by evaluation, thus discovering novel luciferase. Another method is a method in which a mutation is introduced into an already established luciferase to produce and enhance new properties. This method is commonly used as a method for establishing a novel mutation. In this method, a known method, such as site-directed mutagenesis (also called the quick-change method), can be suitably used as a nucleotide mutation method (Non-patent Literature 18).

However, none of the above methods ensures the establishment of high-performance artificial luciferase. For example, various novel luciferases have been established from luminescent animals; however, very few of them have properties sufficient for immediate use in industry, and most of them have been forgotten, without being used in practical applications. In very few cases, properties are modified by mutagenesis; however, mutagenesis generally has a low success rate, and there are very few examples of mutagenesis with good results. Specifically, when one mutation is introduced into a protein having 200 amino acids, the success rate is 1/4000 (200 AA×20 AA (kinds of amino acids)); accordingly, as the number of amino acid mutations increase, e.g., two mutations, three mutations, etc., the number of times mutations are introduced will be immeasurable, which is not practical.

The present inventors established novel artificial luciferases (ALucs) focusing on the following points.
(2-3) Strategies for Establishment of Artificial Luciferase of the Present Invention
Point 1:

First, a "consensus sequence-driven mutagenesis strategy" is suggested as a conventional method to understand protein sequences (Non-patent Literature 13). This is a method for analyzing a sequence, in which it is assumed that frequently occurring amino acids obtained from the alignment of similar amino acid sequences in the known database have the most thermodynamically stable effect. However, the alignment method based on the amino acid similarity has a drawback such that the results may be largely influenced by biased selection, or by the number of similar sequences in the database. While keeping this point in mind, the present researchers made the alignment of similar amino acid sequences represented by Example 1-1.
Point 2:

An approach (single sequence alignment; SSA) is also suggested in which the sequence of luciferase is fragmented into two sequences, and the first sequence and the second sequence are aligned to obtain a hint regarding the luminescence characteristics (Non-patent Literature 3). This approach is based on the premise that a luciferase derived from a copepod luminescent animal has two enzyme active sites. By aligning these two enzyme active sites based on the amino acid similarity, the similarity of the enzyme active sites in the first and second sequences can be easily compared. As described above, since there is a hypothesis that the frequency of amino acids is associated with thermodynamic stability, the present inventors intended to form a thermodynamically stable luciferase sequence by increasing the similarity between the first and second sequences.
Point 3:

Luciferases derived from copepods that have been discovered thus far are known to be similar in the central region and the C-terminal side, but have great variation at the N-terminal side. It is also known that luciferases derived from plankton have about 17 amino acids at the N-terminal side as secretion signals. To complete the entire sequence of ALuc by efficiently determining the sequence at the N-terminal side, which is not known, (1) a method in which similar amino acid sequences in the known database are aligned based on amino acid similarity to extract frequently occurring amino acids is used in combination with (2) a sequence analysis using known software (PSORTII) for looking up the properties of the extracted amino acid sequence to finally determine various candidates for the sequence of ALuc at the N-terminal side.

For example, the properties of an artificially produced sequence at the N-terminal side were examined using PSORTII, and localization shown below is predicted (examples).
N-terminal side of ALuc2
0%: extracellular
22.2%: cytosol
33.3%: ER
N-terminal side of ALuc3
67%: extracellular
11.1%: cyto
11.1%: ER
SP1
44.4%: endoplasmic reticulum
33.3%: mitochondrial
11.1%: Golgi
11.1%: nuclear
SP2
33.3%: extracellular, including cell wall
22.2%: vacuolar
22.2%: cytoplasmic
22.2%: endoplasmic reticulum
SP4
55.6%: extracellular, including cell wall
22.2%: endoplasmic reticulum
11.1%: cytoplasmic
11.1%: vacuolar
Point 4:

The thus-far established length of the amino acid sequence of luciferase derived from copepods varies, and the molecular weight thereof also varies in the range of 20 to 36 kD; such variations are mainly attributable to the varied N-terminal side sequence. In the present invention, to determine the N-terminal side sequence, the N-terminal side amino acid sequence is, under the principle of extraction of frequently occurring amino acids, constructed by making groups, i.e., a group having a relatively short N-terminal side sequence (ALuc5-7), and a group having a relatively long N-terminal side sequence (ALuc2-3 and ALuc8-25); the entire amino acid sequence of the artificial luciferase (ALuc) is thereby determined.
(2-4) Synthesis of Artificial Luciferases (ALucs) of the Present Invention Amino acid sequence determination is conducted according to the strategies of points 1 to 4 described above, thus producing various novel candidate sequences. For actual expression of these amino acid sequences, a gene codon corresponding to each amino acid is applied based on the gene codon table. For advantageous expression in mammalian cells, specifically, for suitable expression in mouse cells, codons are determined. One example of the nucleotide sequence is shown as SEQ ID NO: 23.

A plurality of restriction enzyme sites are introduced into the gene sequences, and synthesis is requested from a manufacturer (Operon) specializing in gene synthesis. By using synthesis genes encoding artificial luciferase (ALuc), which are obtained after being inserted into vectors, sub-cloned vectors inserted into pcDNA3.1 (+) produced by Invitrogen are produced. The vectors are introduced into African green monkey kidney-derived COS-7 cells, and the luminescence characteristics of the resulting artificial luciferases (ALucs) are measured using various spectro-scopes (e.g., luminometer (GloMax 20/20 n; Promega), spectrophotometer (AB-1850; ATTO), image analyzer (LAS-4000; FujiFilm), and microplate reader (Corona)). Their enzymatic activities are evaluated according to the method described in section (3-1) below, and the results are fed back to the amino acid sequences to thereby establish the novel artificial luciferases (ALucs) of the present invention.

3. Enzymatic Activity of Artificial Luciferase (ALuc) of the Present Invention (3-1) Enzymatic Activity Confirmation Method The enzymatic activity of ALuc can be examined, for example, according to the following method.

First, using a known lipid reagent for gene introduction, an expression vector encoding ALuc is introduced into African monkey-derived COS-7 cells; as a control, an expression vector having a known GLuc without any muta-tion into the cells is also introduced in the same manner. At a predetermined time (from 10 to 20 hours, for example, 16 hours) after the introduction of the vector, a cell lysate is prepared using a known lysis reagent.

Thereafter, the cell lysate is mixed with a known substrate solution containing coelenterazine, and its color intensity, temporal stability in luminescence, etc., are measured.

The luminescence intensity may be found by measuring the intensity at a specific wavelength using a known lumi-nescence spectrophotometer after addition of a known sub-strate. By performing the measurement every minute, the temporal stability in luminescence can be evaluated. To measure a shift to a longer wavelength, scanning of the entire wavelength is necessary.

(3-2) Characteristics of Enzymatic Activity of Artificial Luciferase (ALuc) of the Present Invention Typical examples of the artificial luciferase (ALuc) of the present invention include ALuc10 (SEQ ID NO: 11), ALuc15 (SEQ ID NO: 12), ALuc16 (SEQ ID NO: 13), ALuc17 (SEQ ID NO: 24), ALuc18 (SEQ ID NO: 14), ALuc19 (SEQ ID NO: 25), ALuc21 (SEQ ID NO: 26), ALuc22 (SEQ ID NO: 15), ALuc23 (SEQ ID NO: 16), ALuc24 (SEQ ID NO: 27), ALuc25 (SEQ ID NO: 17), ALuc26 (SEQ ID NO: 28), ALuc27 (SEQ ID NO: 29), ALuc28 (SEQ ID NO: 30), ALuc29 (SEQ ID NO: 31), ALuc30 (SEQ ID NO: 32), ALuc31 (SEQ ID NO: 33), ALuc32 (SEQ ID NO: 34), ALuc33 (SEQ ID NO: 35), and ALuc34 (SEQ ID NO: 36).

Characteristics of enzymatic activity commonly observed in conventional copepod luciferases are as follows.
(1) Exhibiting transient high-intensity light and poor lumi-nescence stability,
(2) Having a secretion signal at the N-terminal side,
(3) The size of the luminescence enzyme being smaller than that of other luminescence enzymes, and
(4) Commonly exhibiting blue light (480 nm).

The ALuc series of the present invention maintain char-acteristics (2) and (3), but have much higher luminescence stability (Item (1) above) than conventional copepod luciferases. In particular, ALuc15, ALuc16, ALuc17, ALuc18, ALuc19, ALuc20, ALuc21, ALuc22, ALuc23, ALuc24, ALuc25, ALuc26, ALuc27, ALuc28, ALuc29, ALuc30, ALuc31, ALuc32, ALuc33, and ALuc34 exhibit remarkably stable luminescence signals. Regarding the luminescent color (Item (4) above), ALuc15, ALuc16, ALuc17, ALuc18, ALuc19, ALuc20, ALuc21, ALuc22, ALuc23, ALuc24, ALuc25, ALuc26, ALuc27, ALuc28, ALuc29, ALuc30, ALuc31, ALuc32 ALuc33 and ALuc34 all exhibit luminescence spectra shifted to the long wavelength (green or yellow).

In view of the above, the present invention is confirmed to produce artificial luminescent enzymes of great promise that maintain the advantageous features of conventional copepod luciferases while overcoming common problems of conventional copepod luciferases.

4. Functional Improvement of Artificial Luciferase (ALuc) of the Present Invention The usages of the artificial luciferase (ALuc) of the present invention typically include those as a luminescent enzyme component of a known bioluminescent probe, and, owing to its high luminance and stable luminescence signal, as a substitute for a reporter gene for fluorescent imaging in vivo. The present invention is mainly used in mammals such as humans in vivo, or in mammalian cells in vitro.

Accordingly, the advantageous modifications for improv-ing other functions include modification of the codons corresponding to the amino acid into codons suitable for host organisms for easy expression, and an improvement of expression promoters for indirect functional improvement. Further, by linking a functional peptide to an N- or C-ter-minus of artificial luciferase (ALuc) of the present invention, various additional functions can be expected. For example, by linking a membrane localization signal (MLS) to the N- or C-terminus, the ALuc can be localized in the plasma membrane. In this case, the secretion signal at the N-termi-nal side (positions 1-20, or part of the sequence) derived from ALuc may be present or absent; however, since the secretion signal is transferred across endoplasmic reticulum, the folding efficiency of an ALuc-containing fusion protein can sometimes be increased. In the present invention, when two or more types of peptides, including a signal peptide, are linked, the length, reading frame, etc., are adjusted using a well-known suitable linker, even when the linker is not specified. Localization of ALuc in the plasma membrane allows smooth external supply of the substrate or oxygen. Thus, a luminescent probe (e.g., luminescent capsule) con-taining ALuc as a base can quickly respond to the external signal (see Example 1-8). The present invention adopts the above as required. The modification strategies for improving functions are specifically described below; however, the present invention is not limited to these examples.

5. Application of Luciferase (ALuc) of the Present Invention to "Reporter Analysis Method"

(5-1) "Reporter Analysis Method" of the Present Invention

The ALuc of the present invention and the gene thereof can be preferably used as a "reporter protein" or a "reporter gene" in "reporter analysis methods."

The "reporter protein" or "reporter gene" used in the present invention indicate a luminescent label used for examining the behavior of a target protein or a target gene in cells in response to external stimulus. The "reporter analysis method" in the present invention is an analysis wherein the behavior of a target protein or a target gene in cells in response to external stimulus is observed in view of the luminescence by ALuc, luminescence amount, luminescence timing, or luminescence site, by using the ALuc of the present invention or its gene as a reporter protein or reporter gene. Specifically, the reporter analysis method is a method for qualitatively or quantitatively measuring the expression site, expression timing, or expression amount of the target gene as the luminescence site, luminescence timing, or luminescence amount of reporter protein ALuc.

More specifically, the reporter protein is typically used as a fusion protein by fusing it with the N- or C-terminus of the target protein; however, reporter proteins bisected into the N-terminal side and the C-terminal side are fused with the target protein in a direct manner or via other peptide sequence. The reporter protein is typically used for examining the behavior of the target protein after expression, by linking it to the 5'- or 3' terminus of the target gene to form a chimera gene. Similarly, the reporter gene can be bisected, with one part linked to the 5'-terminus of the target gene, and the other linked to the 3'-terminus of the target gene; or both can be inserted into the target gene for use.

The reporter protein of the present invention can be described as follows using the definition of ALuc above.

The reporter protein comprising a polypeptide having an amino acid sequence represented by any one of following items (i) to (vii) and having copepod luciferase activity;
(i) an amino acid sequence represented by any of SEQ ID NOs: 11 to 17 and 24 to 36;
(ii) an amino acid sequence represented by any of SEQ ID NOs: 11 to 17 and 24 to 36 in which one or several amino acids are deleted, substituted, inserted, or added (herein "several" means 1 to 20, preferably 1 to 10, more preferably 1 to 5 amino acids);
(iii) an amino acid sequence having an identity of not less than 90% with any of amino acid sequences represented by SEQ ID NOs: 11 to 17 and 24 to 36;
(iv) the amino acid sequence represented by SEQ ID NO: 37;
(v) an amino acid sequence represented by SEQ ID NO: 37 in which one or more amino acids are deleted in at least one of a region corresponding to positions 1-29 and a region corresponding to positions 214-218;
(vi) the amino acid sequence represented by SEQ ID NO: 38;
(vii) an amino acid sequence represented by SEQ ID NO: 38 in which one or more amino acids are deleted in at least one of a region corresponding to positions 1-31 and a region corresponding to positions 217-221;
(viii) the amino acid sequence represented by SEQ ID NO: 22; or
(ix) an amino acid sequence represented by SEQ ID NO: 22 in which one or more amino acids are deleted in at least one of a region corresponding to positions 1-29 and a region corresponding to positions 211-215.

When the reporter protein of the present invention is used in in vivo conditions, e.g., in a living body, the "reporter gene" comprising a nucleic acid encoding the amino acid sequence represented by the above (i) to (ix) is linked with a target gene, and incorporated into a vector, etc., thus introducing the vector into target cells.

Hereinafter, the "reporter analysis method" of the present invention is categorized into three groups: "basic," "inducible," and "activatable," which are disclosed in Non-patent Literature 16 of Niu et al.; and application of the ALuc of the present invention to each analysis method is explained. Herein, the "basic" method is the simplest reporter analysis system in which ALuc is linked with each subject protein for labeling. Typical examples include a bioluminescent enzyme fusion protein that is linked with an antibody (i.e., bioluminescent enzyme label antibody). The "inducible" method differs from the "basic method" in that the expression of the reporter is controlled by a promoter. Typical examples include so-called reporter gene assays and two hybrid assays (reporter is expressed depending on stimulus) in addition to a bioluminescence resonance energy transfer (BRET) method. The "activatable" method is a reporter analysis method utilizing the mechanism wherein the reporter itself actively reacts in response to ligand stimulation to illuminate. Typical examples include an integrated-molecule-format bioluminescent probe and a luminescent capsule. This method can also be applied to a protein complementation assay (PCA), protein splicing assay (PSA), etc.

(5-2) Basic Method

When the ALuc of the present invention is applied to a "basic method" as a reporter protein, a fusion protein in which the ALuc is simply linked with a target protein may be produced. The basic method differs from the other reporter analysis methods in that expression during the production of the fusion protein is performed by using an uncontrolled-type promoter.

In the present specification, the "fusion protein" includes (i) a fusion protein integrally expressed from a gene encoding a fusion protein containing a reporter protein, which is ALuc, and a target protein or a peptide recognizing the target protein; and (ii) a fusion protein obtained by separately expressing a reporter protein, which is ALuc, and a target protein or a peptide recognizing the target protein, and linking them by a chemical reaction. Examples of the means for linking separately expressed proteins, etc., by a chemical reaction include linking using a cross linker, linking using an avidin-biotin binding ability, binding using chemical reactivity of amino acid residues, and the like.

A bioluminescent fusion protein that binds to a typical antibody is hereby explained. A bioluminescent fusion protein is completed by producing a chimera DNA in which an ALuc gene is linked with the upstream or downstream of cDNA of antibody single chain variable fragment (scFv), and introducing the DNA into a suitable expression vector. The reporter analysis method of this embodiment is shown in Example 1-15 or Example 1-16 of the present specification.

(5-3) "Inducible" Method

Application of a bioluminescent enzyme to an "inducible method" as a reporter protein has been employed for analyzing the expression timing and expression amount of genes obtained upon the production of recombination protein using recombinant DAN technology. In particular, a bioluminescent enzyme has been widely used as an index indicating the expression timing and expression amount change in response to external stimulus. Examples of analysis systems included in "inducible methods" include reporter gene assays, yeast two-hybrid assays, mammalian two-hybrid assays, protein splicing assays (PSA), protein complementation assays (PCA), circular permutation assays, bioluminescence resonance energy transfer assays (BRET), and the like. Use of the ALuc of the present invention as a reporter gene essential for these analysis systems remarkably improves assay measurement performance. The reporter analysis method of this embodiment is shown in Example 1-9 of the present specification.

Hereinafter, the reporter gene assay and the two-hybrid assay, which are typical "inducible method" analysis systems, are explained in detail.

(i) Reporter Gene Assay

Although reporter gene assays have been widely used as means for analyzing activation of transcription factors in response to external stimulus and gene expression regulation, they are typically used for detecting endocrine disruptors (environmental hormones) that disturb signal transduction via nuclear receptors. The expression of a target gene (e.g., hormonal response gene) involving signal transduction via nuclear receptors is caused when the complex of a ligand and a receptor binds to a cis region (hormone-response element) that regulates the transcription of the gene. This is an assay in which a plasmid that contains a reporter gene such as luciferase at the downstream of the cis region of each hormone-response gene is introduced into cells, and the amount of the hormone molecule, which is to be a ligand, or the amount of the endocrine disruptor is detected by the amount of bioluminescence.

Examples of host cells used herein include yeast cells, bacteria cells such as Escherichia coli, and insect cells, as well as mammalian cells such as COS cell, CHO-K1 cell, HeLa cell, HEK293 cell, and NIH3T3 cell used for general gene recombination. The present invention is mainly used in mammals, such as humans in vivo, or in mammalian cells in vitro.

In the reporter gene assay, firefly luciferase that has been widely used has the following drawbacks: (i) due to its large molecular weight, the start of expression takes a long period of time, thereby imposing a great burden on the host cells, and (ii) due to the low luminescence intensity of firefly luciferase, it generally takes 1 to 2 days after stimulation to obtain a sufficient accumulation of luciferase (reporter). However, by selecting the ALuc of the present invention as a reporter protein, these problems are overcome.

Since the use of the ALuc of the present invention as a reporter protein ensures a significantly high luminescence intensity of the reporter, it has an advantage of very prompt measurement after the stimulation. Accordingly, the measurement time can be greatly reduced compared to conventional reporter proteins while ensuring high temporal stability in luminescence, thereby enabling luminescence measurement even for a cell strain with insufficient gene introduction. Further, since the red-shifted luminescence improves transmittance through the plasma membrane or skin, the background level is reduced, and high measurement accuracy can be attained.

More specifically, the ALuc of the present invention is employed in these reporter gene assays in such a manner that the luminescent enzyme is linked to a known eukaryotic cell expression vector containing a special promoter in an upstream portion, and the vector is then introduced into a eukaryotic cell. After a predetermined time, the measurement is performed either in the presence or absence of signal (stimulation) (Non-patent Literature 20). The known pTransLucent vector can be used as this expression vector for reporter gene assay that can carry the ALuc of the present invention; the ALuc can easily be incorporated therein using a known method.

(ii) Two-Hybrid Method

The two-hybrid method is one of the techniques for discovering protein-protein interactions. In 1989, a yeast two-hybrid (Y2H) system using a Saccharomyces cerevisiae yeast was first established. This method utilizes the fact that the DNA binding domain (GAL4 DBD) and the transcriptional activation domain (TA) of GAL4 protein, which is a transcriptional activator, are separable. Fused GAL4 DBD and protein A (bait) are expressed as a fusion protein, and simultaneously, fused transcriptional activation domain (TA) and protein B (prey) are expressed in the cell as a fusion protein. Thus, interaction between proteins A and B can be observed. When proteins A and B bind, DBD approaches TA and binds to the "UASG" base sequence, which promotes the expression of the reporter gene that is linked to the downstream of the sequence. If the reporter gene is luciferase, the compatibility of proteins A and B can be detected by monitoring bioluminescence in the presence of its specific substrate. This enables screening of protein and peptide that interact with protein A (bait). The protein B (prey) used herein can be supplied from an expression library.

Examples of host cells include, in addition to yeast cells, bacteria such as Escherichia coli, mammalian cells, and insect cells. Other than GAL4 DBD, which is a transcriptional activator derived from a yeast, "LexA" etc., which is a repressor protein derived from Escherichia coli, can be used. A DNA encoding such a protein is linked to a DNA encoding a bait protein (i.e., protein A described above) such as a ligand binding region of a ligand-responsive transcriptional regulator, and then linked to the downstream of a promoter capable of functioning in host cells. On the other hand, usable examples of the "transcriptional activation region of a transcriptional activator" include a GAL4 transcriptional activation region, an Escherichia coli-derived B42 acid transcriptional activation region, a herpes simple virus VP16 transcriptional activation region, and the like. A DNA encoding such a transcriptional activation region is linked to a DNA encoding a prey protein (i.e., protein B described above), and then linked to the downstream of the promoter capable of functioning in host cells.

Specifically, examples of the vector that has a DNA encoding a DNA binding region of transcriptional regulator GAL4 and that can use a budding yeast as a host cells include plasmid pGBT9 (produced by Clontech), etc. Examples of the vector that has a DNA encoding a GAL4 transcriptional activation region and that can be used in budding yeast include plasmid pGAD424 (produced by Clontech), etc. Examples of the vector that has a DNA encoding a GAL4 DNA binding region and that can be used in mammalian cells include pM (produced by Clontech), pBIND (produced by Promega), etc. Examples of the vector that has a DNA encoding a simple herpes virus VP16 transcriptional activation region and that can be used in mammalian cells include pVPl6 (produced by Clontech), pACT (produced by Promega), etc. Examples of the vector that has a DNA encoding a LexA DNA binding region and that can be used in mammalian cells include pLesA (produced by Clontech), etc. Examples of the vector that has a DNA encoding B42 and that can be used in mammalian cells include pB42AD (produced by Clontech), etc.

In this case, for example, a vector in which the ALuc gene of the present invention is inserted as a reporter gene into the downstream of the region (e.g., "USAG") to which GAL4 binds may be formed. In the case of mammalian hosts, by using a commercially available pG5Luc vector (Promega) or pFR-Luc vector (Stratagene), the luciferase (ALuc) of the present invention can be easily used by a known method in place of firefly luciferase incorporated into the vector. The luciferase (ALuc) of the present invention can also be used in place of chloramphenicol acetyltransferase (CAT) of a commercially available pG5CAT vector (Clontech).

(5-4) "Activatable" Method

The analysis system carrying a bioluminescent enzyme as a reporter protein according to the "activatable" method has been also studied and developed by the present inventors as a "bioluminescent probe" technique. Examples of application of the ALuc of the present invention to a "bioluminescent probe" and an "intracellular imaging method" using the bioluminescent probe are explained below as typical examples of the "activatable" method. Before this explanation, the "luminescent fusion protein (luminescent capsule)" developed for the first time in the present invention is explained. In addition, the ALuc of the present invention can be suitably used as a reporter protein used in protein complementation assays (PCA) and protein splicing assays (PSA), which are included in the "activatable" method.

(i) Production of Luminescent Fusion Protein (Luminescent Capsule)

By binding a membrane localization signal to the C-terminus of the ALuc of the present invention, the ALuc can be localized in the plasmamembrane. Such a molecular design allows smooth supply of the substrate and oxygen, enabling visualization of stable bioluminescence with extremely high intensity. For the visualization, it is possible to insert a polypeptide or protein gene as a cargo between the ALuc and a nucleic acid encoding the signal peptide. This allows efficient transfer of the cargo protein to the plasma membrane surface, and makes the place where the protein is transferred illuminated. One typical example is as follows. When the DEVD sequence or IETD sequence responsive to cell death signal is inserted between proteins, the DEVD sequence or IETD sequenceactively responds to the activities of caspase-3 or caspase-8 as signals at the cell death, and functions as a visualization system. The present inventors name the luminescent fusion protein with this structure a "luminescent capsule."

Compared to conventional luminescent probes, the luminescent capsule shows stable optical properties with remarkably high intensity, and is responsive to a specimen that cannot pass through the plasma membrane. The luminescent capsule has a structure in which a "membrane localization signal (MLS)" is linked to the "C-terminus of the luminescent enzyme" as a basic frame structure. Since the effect of a compound causing a form change on the cell surface, such as a compound inducing cell death, can be visualized as a form change in the plasma membrane surface, by this structure or even when the luminescent enzyme of the present invention is linked to a tandem to enhance the amount of luminescence, easy observation is possible. Preferably, it is possible to insert between the MLS and the C-terminus of the luminescent enzyme, a polypeptide causing a form change in the plasma membrane surface, or the partial recognition sequence of the peptide, specifically, the full length or the partial recognition sequence of a G-protein coupled receptor (GPCR) or c-SRC. Further, by inserting a polypeptide inducing cell death or the recognition sequence of the peptide as a cargo between the MLS and C-terminus of the luminescent enzyme, cell death can be visualized. More specifically, when a peptide sequence (generally 20 amino acids or less, preferably 10 amino acids or less) recognized by caspases, proteases (e.g., serine protease and cystein protease), or digestive enzymes (e.g., trypsin and amylase), for example, an amino acid sequence containing "DEVE" or "IETD" used in Example 1-7 is inserted as a cargo, cell death can be visualized by caspase-3 activities. Further, by linking a fluorescence protein or another luminescent enzyme as a cargo between the luminescent enzyme and MLS, the amount of luminescence on the plasma membrane surface is increased as in the case where the luminescent enzyme of the present invention is linked to a tandem, allowing easy observation of the plasma membrane form. Since this fusion protein even responds to a ligand that cannot pass through the plasma membrane, screening with respect to various stimulations is possible.

The luminescent capsule of the present invention is a luminescent fusion protein in which a protein or polypeptide, which is intended to be expressed on the plasma membrane surface, is inserted between the membrane localization signal (MLS) and the C-terminus of the ALuc of the present invention. Typical examples include (a) a luminescent fusion protein wherein a fluorescence protein or luciferase is inserted between the membrane localization signal (MLS) and the C-terminus of the ALuc of the present invention (the luciferase may be ALuc other than the present invention), and (b) a luminescent fusion protein wherein a polypeptide changing the form in the plasma membrane, or a polypeptide having 20 or less amino acids, preferably 10 or less amino acids recognized by the polypeptide changing the form in the plasma membrane, is inserted between the membrane localization signal (MLS) and the C-terminus of the ALuc of the present invention. The polypeptide changing the form in the plasma membrane is particularly preferably a polypeptide inducing cell death, and more preferably a polypeptide having 20 or less amino acids containing caspase or the recognition sequence of the caspase, i.e., "DEVD" or "IETD."

(ii) Application to Luminescent Probe

Further, by incorporating the ALuc of the present invention into the integrated-molecule-format luminescent probe (Non-patent Literature 4, Non-patent Literature 6, Non-patent Literature 9, Non-patent Literature 10, Patent Literature 1 to 4) or the two-molecule-format luminescent probe (Non-patent Literature 5 and Non-patent Literature 8), which are recited in the pending patents applied by the present inventors, the presence or absence of ligand and the intensity of ligand activity can be observed with high luminance. By comprising, as the probe components, (i) the bisected luminescent enzyme (N- and C-terminal fragments), and (ii) a ligand-binding protein responsive to the target ligand and (iii) a recognition protein that recognizes the bond of the ligand with the ligand-binding protein, which are linked to the vicinity of the bisected luminescent enzyme, it is possible to form a high-performance luminescent probe. This luminescent probe functions such that, as the recognition protein recognizes the ligand binding of the ligand-binding protein, the two adjacent fragments of the bisected enzyme complement each other and thereby change the enzymatic activity. Here, due to the high luminescence intensity and stability of the bisected enzyme, it is possible to perform reliable measurement with an improved detection limit.

In the present invention, "integrated molecule-format luminescent probe" denotes a known bioluminescent probe in which all components for visualization imaging are integrated in a single fusion molecule (disclosed in Patent Literature 1-2). For example, "integrated molecule-format luminescent probe" denotes a fusion protein that comprises, as fundamental components, the two fragments of N- and C-terminals obtained by bisecting the ALuc of the present invention, a ligand-binding protein, and a recognition protein for recognizing the ligand-binding protein. Similarly, "two molecule-format luminescent probe" in the present invention denotes a bioluminescent probe in which the two fragments of N- and C-termini obtained by bisecting the ALuc of the present invention are present in the fusion protein containing the ligand-binding protein, and in the fusion protein containing the recognition protein, respectively (see Example 1-10 of the present invention).

When the ALuc of the present invention is used for these bioluminescent probes, the ALuc must be bisected into an N-terminal fragment and a C-terminal fragment. The bisected portion is the same as the bisected portion shown in Example 1-10 or corresponding portions of other ALucs.

Patent Literature 1 to 4 disclose the details regarding the actual method for using the superluminescent enzyme of the present invention as an integrated molecule-format luminescent probe. More specifically, the luciferase (ALuc) of the present invention is bisected, and a chimera DNA encoding a luminescent probe in which a ligand-binding protein and a peptide sequence, which recognizes the change in steric structure upon binding of a ligand to the protein, are linked in a linear chain form. Generally, the chimera DNA is subcloned into a vector suitable for the cells in which the chimera DNA is intended to be expressed, and the vector is introduced into the cells to be expressed. However, the chimera DNA may be ligated to a control sequence at an upstream portion to be directly introduced into the cells. The target cells are preferably mammalian-derived cells, such as human cells. Other suitable examples include cells that exist in a living subject, and culture cells that retain the native function, yeast cells, insect cells, and prokaryotic cells such as Escherichia coli. The type of the vector is also not particularly limited. A suitable vector capable of being expressed in the target host cells is appropriately selected. The introduction of the vector into the cells is performed using known transfection methods such as a microinjection method or an electroporation method, or a transfection method using a lipid (BioPORTER (Gene Therapy Systems, Inc.), Chariot (Active Motif), etc.).

Since the bioluminescent probe using the superluminescent enzyme of the present invention is introduced into cells as a chimera DNA and expressed in the cells as a fusion protein, by measuring the change in light amount emitted from the cells after subjecting the transformed cell to ligand stimulation, the property or levels of activity of the ligand may be evaluated.

When the superluminescent luciferase (ALuc) of the present invention is incorporated in the bioluminescent probe, the "ligand-binding protein," which can be incorporated in the probe together with the ALuc, is intended to mean a protein that binds with a ligand at the ligand binding site. The ligand-binding protein may serve to, in response to the bond with the ligand, for example, change the steric structure, cause phosphorylation, or facilitate protein-protein interaction. Examples of such ligand-binding proteins include nuclear receptors (NR) to which such ligands as hormones, chemical substances, or signal transduction proteins bind; cytokine receptors; and various protein kinases. A suitable ligand-binding protein is selected depending on the target ligand. The ligand that binds to the ligand-binding protein is not particularly limited insofar as it binds to the ligand-binding protein. The ligand may be an extracellular ligand that is introduced in response to extracellular stimulus, or an intracellular ligand that is produced inside the cells. Examples thereof include agonists or antagonists of the receptor protein (for example, intranuclear receptor, or G-protein-linked receptor), signal transduction proteins such as cytokine, chemokine, or insulin, intracellular second messenger, lipid second messenger, phosphorylated amino acid residue, G-protein-linked receptor ligand, and like ligands that specifically bind to proteins involved in intracellular signal transduction.

For example, when the intracellular second messenger, the lipid second messenger, or the like is used as a ligand, the binding domain of each second messenger may be used as the ligand-binding protein. "Second messenger" denotes a different kind of intracellular signal transduction substance that is newly produced as a result of the bond of the extracellular signal transduction substance, such as a hormone or neurotransmission substance, with a receptor that exists in the plasma membrane. Examples of the second messengers include cGMP, AMP, PIP, $PIP_2$, $PIP_3$, inositol trisphosphate ($IP_3$), $IP_4$, $Ca^{2+}$, diacylglycerol, and arachidonic acid. For example, for $Ca^{2+}$ as the second messenger, calmodulin (CaM) may be used as the ligand-binding protein.

(iii) Intracellular Imaging

Further, using the gene encoding the ALuc enables stable introduction of the ALuc into various cell strains. For example, using the gene enables stable introduction of the ALuc into the undifferentiated embryonic cells, ES cells, novel induced pluripotent stem cells (iPS cells). Since the cells do not emit light themselves, it has been very difficult to research the intracellular molecular phenomenon and tissue specificity of the cells. To address this difficulty, a molecular probe containing the ALuc is introduced into somatic cells before the embryo is formed, and then the embryo is differentiated into various tissues. This enables measurement of specific molecular phenomena in respective organs with high sensitivity.

This process is performed according to the method of Yamanaka et al. (Non-patent Literature 17).

Further, by linking the ALuc of the present invention to a suitable signal peptide, the ALuc can be used for luminance imaging of various organelles. For example, by linking a GAP-43-derived MLCCMRRTKQV sequence (SEQ ID NO: 1) to an N- or C-terminus of ALuc, the ALuc may be localized in the plasma membrane. Linking a GRK-KRRQRRR sequence (SEQ ID NO: 2) to a terminus enables localization in cell cytoplasm. Further, for localization in endoplasmic reticulum (ER) and cellular nucleus, KDEL (SEQ ID NO: 3) and DPKKKRKV (SEQ ID NO: 4) sequences, respectively, are linked to a terminus. Furthermore, by linking to HIS-tag (HHHHHH) (SEQ ID NO: 5), FLAG-tag (DYKDDDDK) (SEQ ID NO: 6), Myc-tag (EQKLISEEDL) (SEQ ID NO: 7), HA-tag (YPYDVPDYA) (SEQ ID NO: 8), V5-tag (GKPIPNPLLGLDST) (SEQ ID NO: 9), T7-tag (MASMTGGQQMG) (SEQ ID NO: 10) or like antigen sites, the ALuc can be used for immunostaining or separation/refinement in acellular systems. In these usages, known immunostaining technologies or immunocytochemistry may be adopted.

[II] DETERMINATION OF OPTIMUM REACTION SOLUTION FOR BIOASSAY

1. Buffer for Bioassay (1-1) Lysis Buffer (Cell Lysis Solution) and Assay Buffer (Reaction Solution)

Conventionally conducted bioassays involve two separate assay buffers: a buffer for lysis (cell lysis solution); and a buffer for assay (reaction solution). This is because high lytic activity and low inhibitory effect on a luminescent enzyme are considered essential for quick lysis of the cells, whereas stable assay conditions and removal or analysis of self-luminescence inducing components to reduce background are considered essential for a bioassay reaction.

Promega Corporation has been selling a lysis buffer and an assay buffer under the respective trade names of Luciferase Lysis Buffer (catalog number: E291A) and Luciferase Assay Buffer (catalog number: E290A). New England Biolabs Inc. (NEB) has also been selling a lysis buffer and an assay buffer under the respective trade names of Luciferase Lysis Buffer (catalog number: B3321) and Luciferase Assay Buffer (catalog number: E3300S). Although neither Promega nor NEB discloses the formulations of their commercial products, both disclose complex protocols in which a lysis buffer and an assay buffer are separately used.

In the present invention, as stated above, studies on the buffer component formulations shown below were conducted with the intent of simplifying the complex protocols, and enhancing the reaction stability and the sensitivity.

(a) surfactant: polyoxyethylene octylphenyl ether (Triton X-100; TX100), Nonidet P-40 (NP40), polyoxyethylene sorbitan monolaurate (Tween20; TW20), polyoxyethylene sorbitan monooleate (TW80), polyoxyethylene cetyl ether (Brij58), sodium dodecyl sulfate (SDS), and the like. The degree of hydrophilicity is indicated as TW20>Brij58>TW80>TX100>NP40; and the degree of the power of surfactant is indicated as NP40>TX100>Brij58>TW20>TW80.

(b) salts: NaCl, KCl, $(NH_4)_2SO_4$, and the like (c) SH reagents: mercaptoethanol, DTT, and the like (d) polyols: glycerol, glucose, sucrose, and the like (e) glycols: polyethylene glycol (PEG), polypropylene glycol (PPG)

(f) chelate reagents: EGTA, EDTA, and the like (g) protease inhibitors: aprotinin (molecular weight: 6.5 kD), leupeptin (molecular weight: 427), pepstatin A (pepstatin, molecular weight: 686), phenylmethylsulfonyl fluoride (PMSF, molecular weight: 174), antipain (antipain, molecular weight: 605), chymostatin (chymostatin, molecular weight: 608), pefabloc SC (AEBSF, 240 Da), DFP (184 Da), p-APMSF (216 Da), STI (20,100 Da), leupeptin (460 Da), N-tosyl-L-phenylalaninechloromethylketone, 3,4-dichloroisocoumarin (215 Da), EDTA-$Na_2$ (372 Da), EGTA (380 Da), 1,10-phenanthroline (198 Da), phosphoramidon (580 Da), dithiobis (2-amino-4-methylpentane), E-64 (357 Da), cystatin, bestatin, epibestatin hydrochloride, aprotinin, minocycline, ALLN (384 Da), and the like (g) buffer agents: p-toluenesulfonic acid, tartaric acid, citric acid, phthalate, glycine, trans-aconitic acid, formic acid, 3,3-dimethylglutaric acid, phenylacetic acid, sodium acetate, succinic acid, sodium cacodylate, sodium hydrogen maleate, maleic acid, sodium phosphate, $KH_2PO_4$, imidazole, 2,4,6-trimethylpyridine, triethanolamine hydrochloride, sodium 5,5-diethylbarbiturate, N-ethylmorpholine, sodium pyrophosphate, tris(hydroxymethyl)aminomethane, bicine, 2-amino-2-methylpropane-1,3-diol, diethanolamine, potassium p-phenolsulfonate, boric acid, sodium borate, ammonia, glycine (glycine), $Na_2CO_3$/$NaHCO_3$, sodium borate, or a combination thereof (h) Others: sodium molybdate (stabilization of receptors), dithiothreitol (dithiothreitol, DTT) (reducing agent)

(1-2) Buffer Component 1, a Basic Buffer, of the Present Invention (HBSS Buffer)

In the present invention, the HBSS buffer (Hanks' balanced salt solution) is used as a basic composition. An HBSS buffer was prepared in accordance with a known protocol (e.g., see the website of National Institute of Biomedical Innovation at http://cellbank.nibio.go.jp/legacy/sheet/att00011.htm), as described below.

First, the following four types of solutions are prepared beforehand, and mixed for use.

Solution 1: 1.4% $NaHCO_3$ solution

Solution 2: a solution prepared by dissolving 80.0 g of NaCl, 4.0 g of KCl, 2.0 g of $MgSO_4.7H_2O$, 0.6 g of $Na_2HPO_4.2H_2O$, 10.0 g of glucose, and 0.6 g of $KH_2PO_4$ in 800 ml of water Solution 3: a solution prepared by dissolving 1.4 g of $CaCl_2$ in 100 ml of water Solution 4: a solution prepared by weighing 0.4 g of phenol red, making it into a paste with a small amount of water, and adding water thereto to give 150 ml of a solution The mixture is adjusted to a pH of 7.0 with a sodium hydroxide solution (N/20) so as to give 200 ml.

For use, 2.5 ml of solution 1, 8 ml of solution 2, 1 ml of solution 3, and 1 ml of solution 4 are added to 87.5 ml of sterile water. When phenol red is not necessary, solution 4 can be omitted.

(1-3) Buffer Component 2, a Basic Buffer, of the Present Invention (Tris-Buffer)

The Tris buffer refers to a widely used conventional buffer component (as used herein, "tris" is an abbreviation for tris(hydroxymethyl)aminomethane, which is typically prepared by adding HCl to 10 mM of a tris salt to thereby adjust the pH, and optionally adding 1 mM of EDTA thereto as an additive), and is used in a variety of biological studies because of its high biocompatibility. Nonetheless, there has been insufficient study of the effects of the Tris buffer on a bioluminescent reaction.

In the present invention, it was found that a Tris buffer can be suitably used for bioluminescence, and can be a basic buffer component usable in both lysis and assay.

(1-4) Buffer Formulation in the Present Invention

The above-stated basic buffer components, an HESS buffer and a Tris-buffer, are combined for use. These buffers are mixed at a ratio of 20 to 50:50 to 20, preferably 40 to 60:60 to 40, and most preferably 60:40 in volume % (v/v).

The surfactants NP-40, TW80, and SDS are combined for use. The NP-40, TW80, and SDS are mixed at a ratio of 1:0.1 to 1:0 to 0.5, preferably 1 to 2:0.5 to 2:0.1 to 1, and most preferably 1:1:0.1 in volume % (v/v).

The surfactant TW80 is mixed with other surfactants and the ratio is adjusted to be 1 to 10 volume % (v/v), and preferably 5 to 10 volume % (v/v).

For polyols, polyethylene glycol (PEG), and a sugar component (sucrose, glucose) are combined. PEG400 is contained in an amount of 0.01 to 10 volume % (v/v), and the sugar component (sucrose, glucose) is contained in an amount of 0 to 20 mg/mL. PEG400 is preferably contained in an amount of 0.1 to 10 volume % (v/v), and the sugar component (sucrose, glucose) is preferably contained in an amount of 2 to 10 mg/mL.

For heavy metals, Fe(III), Cu(II), Mo(VI), and Zn(II) can be contained singly or in a combination in a concentration within a range of 0.01 to 1 PPM, and preferably 1 PPM.

The halogen ions $Br^-$ and I can be contained singly or in combination in a concentration of 1 to 100 mM, and preferably 50 to 100 mM.

It is further preferable to optionally add a reducing agent, such as vitamin C, to improve the luminescence stability.

In the Examples, buffer formulations that showed excellent results in the bioluminescence measurement step after the cell lysis step were basically those for which a C3 buffer was used as a cell lysis solution. The probable reason for the excellent results is that the C3 buffer comprises, in addition to a Tris-HCl buffer as a basic buffer, NP-40 having excellent surfactant power and MgCl2 having high physiological compatibility. The buffer combinations that particularly showed excellent results are as follows:
1. After cell lysis with a C3 buffer, C8 and C10 assay buffers were used.
2. After cell lysis with a C3 buffer, a C6 assay buffer was used.
3. After cell lysis with a C3 buffer, an assay buffer prepared by adding Al(III), Ca(II), Cu(II), Fe(III), or Mg(II) to an HBSS buffer was used.
4. After cell lysis with a C3 buffer, an assay buffer prepared by adding 1% PEG or PPG to an HBSS buffer was used.
5. After cell lysis with a C3 buffer, an assay buffer prepared by adding 50 mM of KI or 100 mM of KBr to an HESS buffer was used.
6. After cell lysis with a C3 buffer, an assay buffer prepared by adding 2 mg/mL of D(+)glucose or glycine to an HBSS buffer was used.

From the above results, preferable buffer formulations as a one-shot reaction solution were narrowed down as shown below.

Specifically, it was found that a basic formulation of "one-shot reaction solution" in a bioluminescent enzyme utilization technique, where prompt lysis and observation under high luminescent intensity are required, can be established by combining a Tris-HCl buffer, which is a basic buffer of the C3 buffer, with an HESS buffer, and further combining a surfactant, NP-40 or SDS, salts such as Al(III), Ca(II), Cu(II), Fe(III), or Mg(II), PEG or PPG, a halogen ion (I$^-$, Br$^-$, and D(+)glucose or glycine.

On the basis of such an idea, C14 to C18 buffers basically comprising a combination of a C3 buffer and an HESS buffer were established as a "one-shot reaction solution." However, when used for bioluminescence probes, C14 to C18 buffers failed to show preferable results. When C19 to C22 buffers comprising TW80 in place of an HBSS buffer were used, C19, C21, and C22 buffers prepared by combining TW80 with a C3 buffer in an amount of 1 to 10% without adding SDS were found to serve as a one-shot buffer that enables fast measurement. TW80 was selected as an additional additive because TW80 can balance with NP-40 in terms of surfactant hydrophilicity and the power of surfactant.

The present inventors had previously found in experiments conducted using another luminescent enzyme that a Tris-HCl buffer, when comprising the surfactant NP-40 in combination with SDS, increases luminescence intensity (the results not shown). Thus, the present inventors conducted the following experiment using a C4 buffer comprising SDS in addition to a Tris-HCl buffer and NP-40, in place of a C3 buffer comprising a Tris-HCl buffer and NP-40 as basic components. More specifically, the present inventors conducted the experiments using, as a one-shot buffer, C23 to C26 buffers each comprising, in addition to a C4 buffer as a basic component, TW80 and an HBSS buffer in a different formulation. The present inventors found that C23, C24, and C25 enable fast measurement with high S/N ratios.

As described above, one-shot reaction buffers for a bioluminescent enzyme were established by combining a C4 buffer with a C13 buffer comprising an HBSS buffer as a basic component, and adding TW80 and D-luciferin as a substrate thereto.

(1-5) Buffer Solution Used in the Examples of the Present Invention

The following shows the formulations of the buffer solutions used in the Examples of the present invention.

TABLE 1

Buffer Formulations

| Name (Abbrev. Name) | Buffer Basic Substance | Additive 1 | Additive 2 | Additive 3 | Additive 4 |
|---|---|---|---|---|---|
| Composition 1 (C1) | 20 mM Tris-HCl (pH 7.5) 2.5 mM Sodium Pyrophosphate 1 mM Glycerophosphate | 1% Triton | 1 mM EDTA 1 mM EGTA | 1 mM Na$_3$VO4 1 µg/ml Leupeptin | 150 mM NaCl |
| Composition 2 (C2) | 50 mM Tris-HCl (pH 6.8) | 1% (w/v) SDS | 10% (v/v) 2-Mercaptoethanol | 10% (v/v) Glycerol | 0.001% (w/v) Bromophenol Blue |
| Composition 3 (C3) | 20 mM Tris-HCl (pH 7.4) | 0.05% (w/v) NP-40 | 0.05% Sodium Azide | 2.5 mM Magnesium Chloride | 200 mM NaCl |
| Composition 4 (C4) | 25 mM Tris-HCl (pH 7.6) | 1% NP-40 0.1% SDS | 1% Sodium Deoxycholate | | 150 mM NaCl |
| Composition 5 (C5) | H$_2$O | None | None | None | |
| Composition 6 (C6) | Sodium Phosphate Buffer (PBS) | 145 mM NaCl | | | |
| Composition 7 (C7) | Sodium Phosphate Buffer (PBS) | 145 mM NaCl | 0.5% BSA | | |
| Composition 8 (C8) | HBSS buffer | | | | |
| Composition 9 (C9) | Tris buffer | EDTA | | | |
| Composition 10 (C10) | Tris buffer | EDTA | Polyethylene Glycol (PEG) | | |
| Composition 11 (C11) | Tris buffer | 10 mM MgCl$_2$ | | | |
| Composition 12 (C12) | Tris buffer | 50 mM MgCl$_2$ | | | |
| Composition 13 (C13) | HBSS buffer | PEG 100 0.01% | Fe (III) 0.1 ppM, As (v) 0.1 ppM | | |

TABLE 2

Buffer Formulations

| Name (Abbrev. Name) | 1st Buffer | 2nd Buffer | Additive 1 | Additive 2 | Mixing Ratio of 1$^{st}$ and 2$^{nd}$ Buffers |
|---|---|---|---|---|---|
| Composition 14 (C14) | Formulation of C3 | HBSS Buffer | | | 2:8 |
| Composition 15 (C15) | Formulation of C3 | HBSS Buffer | | | 4:6 |

TABLE 2-continued

Buffer Formulations

| Name (Abbrev. Name) | 1st Buffer | 2nd Buffer | Additive 1 | Additive 2 | Mixing Ratio of 1st and 2nd Buffers |
|---|---|---|---|---|---|
| Composition 16 (C16) | Formulation of C3 | HBSS Buffer | | | 6:4 |
| Composition 17 (C17) | Formulation of C3 | HBSS Buffer | | | 8:2 |
| Composition 18 (C18) | Formulation of C3 | HBSS Buffer | | | 10:0 |
| Composition 19 (C19) | Formulation of C3 | | TW80 1% | | |
| Composition 20 (C20) | Formulation of C3 | | TW80 1% | SDS 0.1% | |
| Composition 21 (C21) | Formulation of C3 | | TW80 5% | | |
| Composition 22 (C22) | Formulation of C3 | | TW80 10% | | |
| Composition 23 (C23) | Formulation of C4 + TW80 1% | HBSS Buffer | | | 2:8 |
| Composition 24 (C24) | Formulation of C4 + TW80 1% | HBSS Buffer | | | 4:6 |
| Composition 25 (C25) | Formulation of C4 + TW80 1% | HBSS Buffer | | | 6:4 |
| Composition 26 (C26) | Formulation of C4 + TW80 1% | HBSS Buffer | | | 8:2 |
| Composition 27 (C27) | Formulation of C4 + TW80 1% | Formulation of C13 | | | Compositional Ratio of C4 to C13 = 6:4 |
| Composition 28 (C28) | Formulation of C4 + TW80 1% | Formulation of C13 | D-luciferin | | Compositional Ratio of C4 to C13 = 6:4 |
| Composition 29 (C29) | Formulation of C4 + TW80 1% | Formulation of C13 | $Mg^{2+}$ (1 ppm) D-luciferin | | Compositional Ratio of C4 to C13 = 6:4 |

2. Bioassay of Interest in the Present Invention

The present invention relates to a buffer formulation that is expected to be applied to the following bioassays. In conducting a reporter-gene assay, two-hybrid assay, protein complementation assay, intein-mediated protein splicing assay, or single-chain probe-based assay, a measurement is directly carried out with cultured cells without carrying out the "cell lysis step."

For example, in a reporter-gene assay, cells transfected with a reporter expression vector in a 96-well plate are ligand-stimulated. After that, when the cells produce luminescence, 50 μL of the reaction solution is added, and a measurement is immediately conducted.

When an integrated-molecule-format bioluminescent probe is used, cells for expressing the integrated-molecule-format bioluminescent probe in a 96-well plate are ligand-stimulated. After stimulation, 50 μL of the reaction solution is added, and a measurement is immediately conducted.

3. Luminescent Enzyme for Use in Bioassay of the Present Invention

The luminescent enzyme for use in the bioassays of the present invention includes all types of luminescent enzymes. Examples of the luminescent enzyme include bioluminescent enzymes derived from insects and marine animals, typically firefly luciferases, click beetle luciferases, *Renilla* luciferases, and copepod luciferases (*Metridia longa* luciferase, *Metridia pacifica* luciferase).

As used herein, the term "copepod luciferases" refers to luciferases sharing common enzyme activity and structural characteristics with luciferases originating from known copepods. Specifically, such luciferases are those having an optimum pH of about 5 to 8, an optimum temperature of about 4 to 25° C., and enzyme activity that catalyzes a luminescent reaction with coelenterazine as a substrate. The luciferases comprise two enzyme active domains with a secretion signal at their N-terminus, and have a molecular weight of about 20 kD (18 kD to 28 kD), which is the smallest among all of the luminescent enzymes.

Preferable examples of luminescent enzymes usable in the bioassays of the present invention include the aforementioned novel artificial luciferases (ALuc) according to the present invention.

4. Measuring Procedure and Measuring Apparatus Used in the Present Invention

The ligand activity can be measured in accordance with a typical bioluminescence assay, and conventional protocols can be used without any restriction.

Luminometers (e.g., Mini Lumat LB 9506, Berthold; and GloMax 20/20n, Promega) have typically been used to measure bioluminescence intensity. A cell lysis solution is poured over cultured cells in a plate to thereby produce a cell lysate. After the cell lysate is mixed with a substrate, the luminescence is immediately measured.

To measure the ligand activity of cultured cells in a 96-well plate, a ready-made bioluminescence plate reader (e.g., Mithras LB 940, Berthold; and SH-9000, Corona) can be used. Using a substrate solution autoinjector attached to the plate reader, a substrate can instantaneously be introduced, and bioluminescence generated by the expressed probe can instantaneously be measured in the presence of the ligand.

5. Analyte of Interest in Screening Method

Examples of analytes in these screening methods include organic or inorganic compounds (particularly compounds of low molecular weight), proteins having bioactivity, and peptides. These substances may be those whose function and structure are either known or unknown. A "combinatorial chemical library" can be an effective means as a group of analytes for efficiently identifying target substances. The preparation and screening of a combinatorial chemical library are well known in the art (see, e.g., U.S. Pat. Nos. 6,004,617 and 5,985,365). Alternatively, a commercially available library may be used (e.g., libraries available from ComGenex (US), Asinex (Russia), Tripos Inc. (US), ChemStar, Ltd. (Russia), 3D Pharmaceuticals (US), and Martek Biosciences). By applying a combinatorial chemical library to a cellular cluster for expressing a probe, a "high-throughput screening" can be carried out.

6. Kit

The present invention also provides a bioassay kit comprising the aforementioned reaction buffers for bioluminescence. The kit according to the present invention may optionally comprise various components for carrying out a bioassay. Examples of such components include, but are not limited to, luminescent enzymes, vectors comprising genes for encoding luminescent enzymes, cells for expressing luminescent enzymes, luminescent substrates, various instruments (96-well plates, and tubes), and control samples. The kit may also comprise a user manual describing the procedure for carrying out the bioassays according to the present invention.

Preferable examples of luminescent enzymes include bioluminescent enzymes derived from insects and marine animals, typically firefly luciferases, click beetle luciferases, *Renilla* luciferase, copepod luciferases (*Metridia longa* luciferase, *Metridia pacifica* luciferase), and the artificial luciferases (ALuc) described in section [I] above. The artificial luciferases (ALuc) are particularly preferable examples.

A vector comprising a gene for encoding a luminescent enzyme can be produced in accordance with a known technique depending on the intended bioassay (e.g., reporter-gene assay, two-hybrid assay, protein complementation assay, intein-mediated protein splicing assay, and single-chain probe-based assay).

When the luminescent enzyme for use is, for example, a copepod luciferase or the artificial luciferases (ALuc) of the present invention, a preferable luminescent substrate is coelenterazine, which refers to both native coelenterazine (native CTZ) and the derivatives of native coelenterazine.

Examples of control samples include positive controls comprising a luminescent enzyme in a predetermined amount, and negative controls not comprising a luminescent enzyme.

The kit according to the present invention can be produced by combining the above-described components in accordance with a known technique. The kit according to the present invention can be used for carrying out the aforementioned bioassays of the present invention.

[III] TERMS AND CONCEPTS USED IN THE PRESENT INVENTION

The other terms and concepts used in the present invention are specifically defined in the descriptions of embodiments and examples of the invention. The terms are generally selected from the IUPAC-IUB Commission on Biochemical Nomenclature, or based on interpretations of idiomatic terms and words in the related field. Except for the techniques with apparent sources, the various techniques used to carry out the present invention can be easily and consistently performed by one of ordinary skill in the art with reference to published documents, etc. For example, genetic engineering and molecular biological techniques can be carried out according to J. Sambrook, E. F. Fritsch & T. Maniatis, "Molecular Cloning: A Laboratory Manual (2nd edition)," Cold Spring Harbor Laboratory Press, Cold Spring Harbor, N.Y. (1989); D. M. Glover et al. ed., "DNA Cloning," 2nd ed., Vols. 1 to 4, (The Practical Approach Series), IRL Press, Oxford University Press (1995); Ausubel, F. M. et al., Current Protocols in Molecular Biology, John Wiley & Sons, New York, N.Y., 1995; Japanese Biochemical Society ed., "*Zoku Seikagaku Jikken Koza* 1 [Continuation of Biochemistry Experimental Series 1], *Idensi Kenkyu Ho* [Gene Study Method] II," Tokyo Kagaku Dojin (1986); Japanese Biochemical Society ed., "*Shin Seikagaku Jikken Koza* 2 [New Biochemistry Experimental Series 2], *Kakusan* [Nucleic Acid] III (*Kumikae DNA Gijutsu* [DNA Recombinant Technology])," Tokyo Kagaku Dojin (1992); R. Wu ed., "Methods in Enzymology," Vol. 68 (Recombinant DNA), Academic Press, New York (1980); R. Wu et al. ed., "Methods in Enzymology," Vols. 100 (Recombinant DNA, Part B) & 101 (Recombinant DNA, Part C), Academic Press, New York (1983); R. Wu et al. ed., "Methods in Enzymology," Vols. 153 (Recombinant DNA, Part D), 154 (Recombinant DNA, Part E), & 155 (Recombinant DNA, Part F), Academic Press, New York (1987), etc.; the methods mentioned in the documents referenced in these documents; or other various similar methods and modified methods thereof that are substantially the same as the disclosed methods. The proteins, peptides, and DNAs encoding them used in the present invention are available from existing databases (e.g., URL: http://www.ncbi.nlm.nih.gov).

EXAMPLES

The following examples specifically describe the present invention in more detail; however, the present invention is not limited to the Examples.

The other terms and concepts used in the present invention are based on the interpretations of idiomatic terms and words in the related field. Except for the techniques with apparent sources, the various techniques used to carry out the present invention can be easily and consistently performed by one of ordinary skill in the art with reference to published documents, etc. The various analyses were performed in accordance with the methods disclosed in instruction manuals, catalogs, or the like of the analytical instruments, reagents, and kits used in the analyses.

The disclosures of the technical documents, patent publications, and specifications of pending patent applications cited herein are incorporated into the present specification by reference.

(Example 1-1) Extraction of Amino Acid Sequences of Artificial Luciferases (ALucs)

According to the publicly known database of the National Center for Biotechnology Information (NCBI), etc., copepod luciferase sequences were aligned based on the similarity of amino acids to find frequently occurring amino acids. Based on the frequently occurring amino acids, novel artificial luciferase (ALuc) prototypes were made (FIG. 1A). Each of the luciferase sequences in the database was fragmented into the top portion, the first portion, and the second portion, and frequently occurring amino acid sequences were extracted from the similarity alignment of top portion sequences (FIG. 1B). Further, by overlapping the first portion and the second portion, not only frequently occurring amino acids but also amino acid sequences having high homology between the first portion and the second portion were extracted, thus making about 23 artificial luciferase sequences.

Based on the many artificial luciferase (ALuc) sequences obtained from the similarity alignment above, gene codons optimized for mouse cells were suitably applied to construct the same number of artificial gene sequences. Based on these gene sequences, actual artificial genes were obtained from an outsourcing company (Operon Biotechnology, Co., Ltd.) specializing in artificial gene synthesis.

(Example 1-2) Comparison of Luminescence Intensity, Luminescence Stability, and Red-Shifted Degree of Artificial Luciferases (ALucs)

The artificial luciferase (ALuc) genes synthesized by the above process were subcloned into mammalian cell expression vectors (pcDNA3.1 (+)). Each expression vector was transfected with African green monkey kidney-derived COS-7 cells, and the luminescence intensity, luminescence stability, and red-shifted degree of artificial luciferases (ALucs) were compared (FIGS. 2 to 5).

Figure 2:
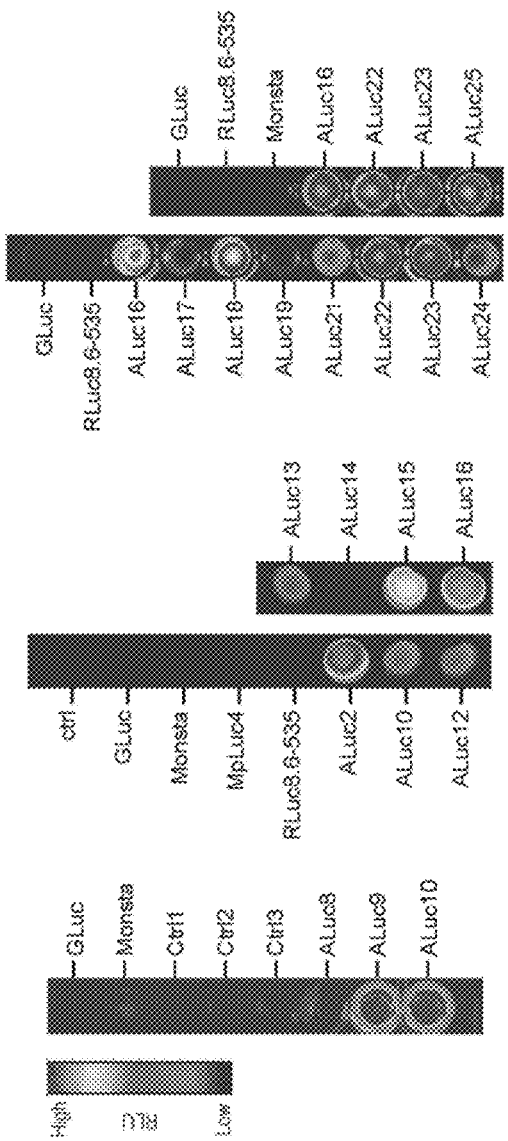
FIG. 2 Comparison of luminescence intensity of the artificial bioluminescent enzymes (ALuc). The luminescence intensity on a 96-well plate was measured using a known image analyzer (LAS-4000; FujiFilm). The luminescence intensity was shown in similar false colors from red (high luminescence intensity) to blue (low luminescence intensity). Yellow denotes an intermediate luminescence intensity. GLuc, MpLuc4, and RLuc8.6-535 are luminescent enzymes that have been evaluated to have the highest bioluminescence intensity.

First, the luminescence intensity of artificial luciferases (ALucs) was compared (FIG. 2). For the comparison, COS-7 cells containing a vector encoding each luciferase were cultured overnight, and then the relative luminescence intensity was measured by using an assay solution, which is a mixture of a cell lysis solution and a substrate, produced by Promega, and a luminescence image analyzer (LAS-4000).

The results indicated that ALuc2, ALuc9, ALuc10, ALuc15, ALuc16, ALuc18, ALuc22, ALuc23, ALuc25, etc. exhibited relatively high luminescence intensity. According to the luminescence intensity measurement by using the luminescence image analyzer, these ALucs were confirmed to have luminescence intensity about 50 folds higher than that of conventional *Gaussia*-derived luciferase (GLuc), *Renilla reniformis*-derived luciferase (*Renilla* luciferase), and *Metridia pacifica*-derived luciferase (MpLuc4).

(Example 1-3) Examination of Luminescence Stability of Artificial Luciferases (ALucs)

Figure 3:
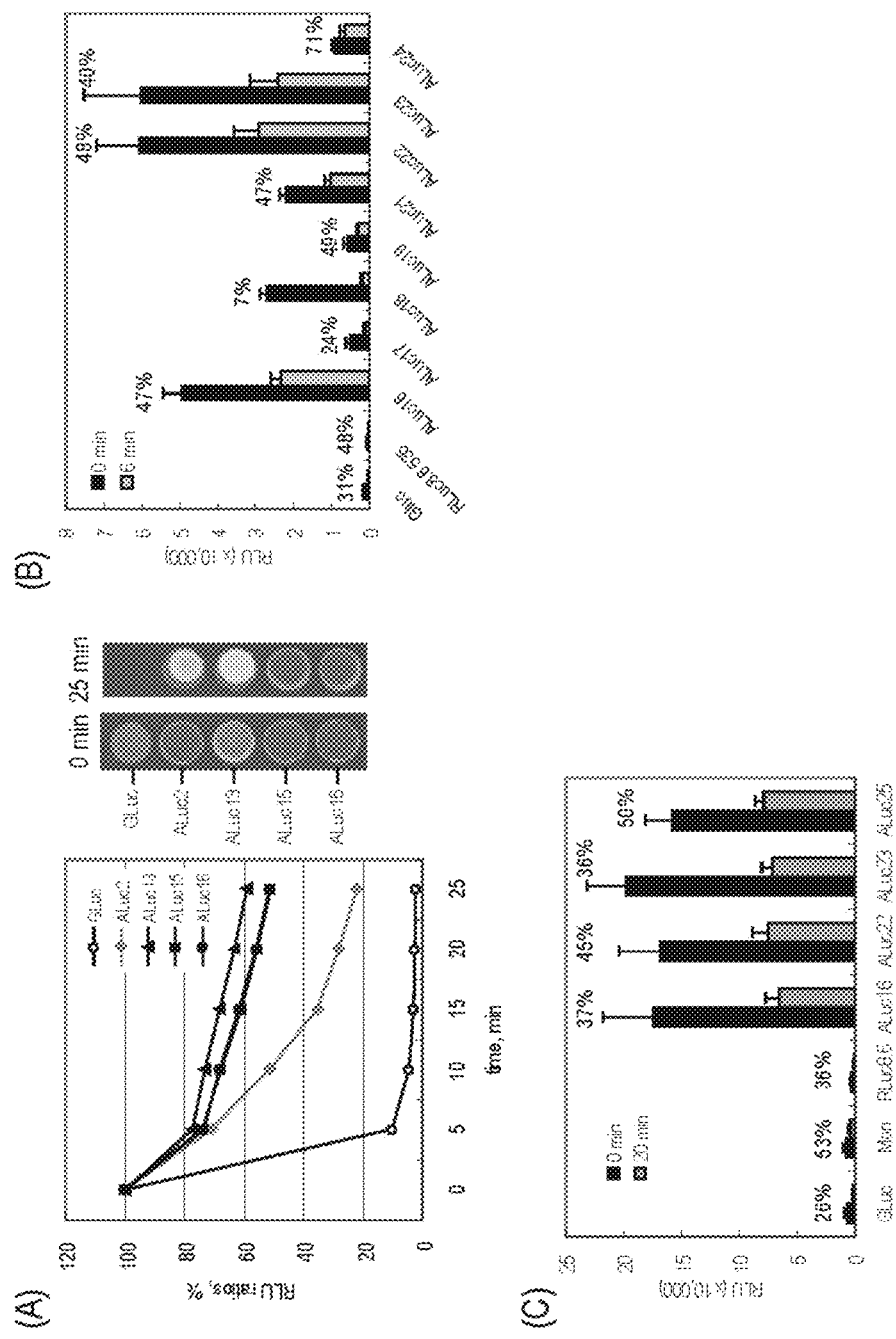
FIG. 3 Comparison of luminescence stability of the artificial bioluminescent enzymes (ALuc). (A) Changes in luminescence intensity over time after introduction of substrate. ALuc15 and ALuc16 maintained 60% of their original luminescence intensity even 25 minutes after the introduction of substrate. The image on the right shows their luminescence images. (B) Comparison of luminescence intensity of the artificial bioluminescent enzymes (ALuc) after 0 minutes (black bar) from the introduction of substrate, and after 6 minutes (gray bar) from the introduction of substrate. ALuc24 was excellent in luminescence stability, but slightly low in luminescence intensity. The luminescence intensity of ALuc22 decreased to about half of the original luminescence intensity after 6 minutes. (C) Comparison of luminescence intensity of the artificial bioluminescent enzymes (ALuc) after 0 minutes (black bar) from the introduction of substrate, and after 20 minutes (gray bar) from the introduction of substrate.

The luminescence stability of the artificial luciferases (ALucs) of the present invention was examined in various respects (FIG. 3). COS-7 cells containing each luciferase gene were cultured for 9 hours, and treated with a cell lysis solution produced by Promega for 20 minutes. Temporal changes in luciferase luminescence intensity after the introduction of a substrate-containing reaction solution produced by Promega were observed every five minutes (FIG. 3A). As a result, after the substrate injection, a sudden luminescence decrease phenomenon was observed in conventional GLuc or ALuc2; however, ALuc15 and ALuc16 retained about 60% of their initial luminescence intensity even 25 minutes after the substrate injection.

This experiment was expanded to artificial luciferases ALuc16 to ALuc25 (FIG. 3BC). The results indicated that ALuc16, ALuc22, ALuc23, ALuc25, etc., had advantageous initial luminescence intensity. The results also confirmed that ALuc24 had relatively low luminescence intensity, but exhibited extremely higher luminescence sustainability than other artificial luciferases (ALucs). In contrast, conventional luciferases (GLuc and RLuc8.6-535) had extremely poor luminescence intensity and poor luminescence sustainability.

(Example 1-4) Heat Resistance and Degree of Extracellular Secretion of Artificial Luciferases (ALucs)

Figure 4:
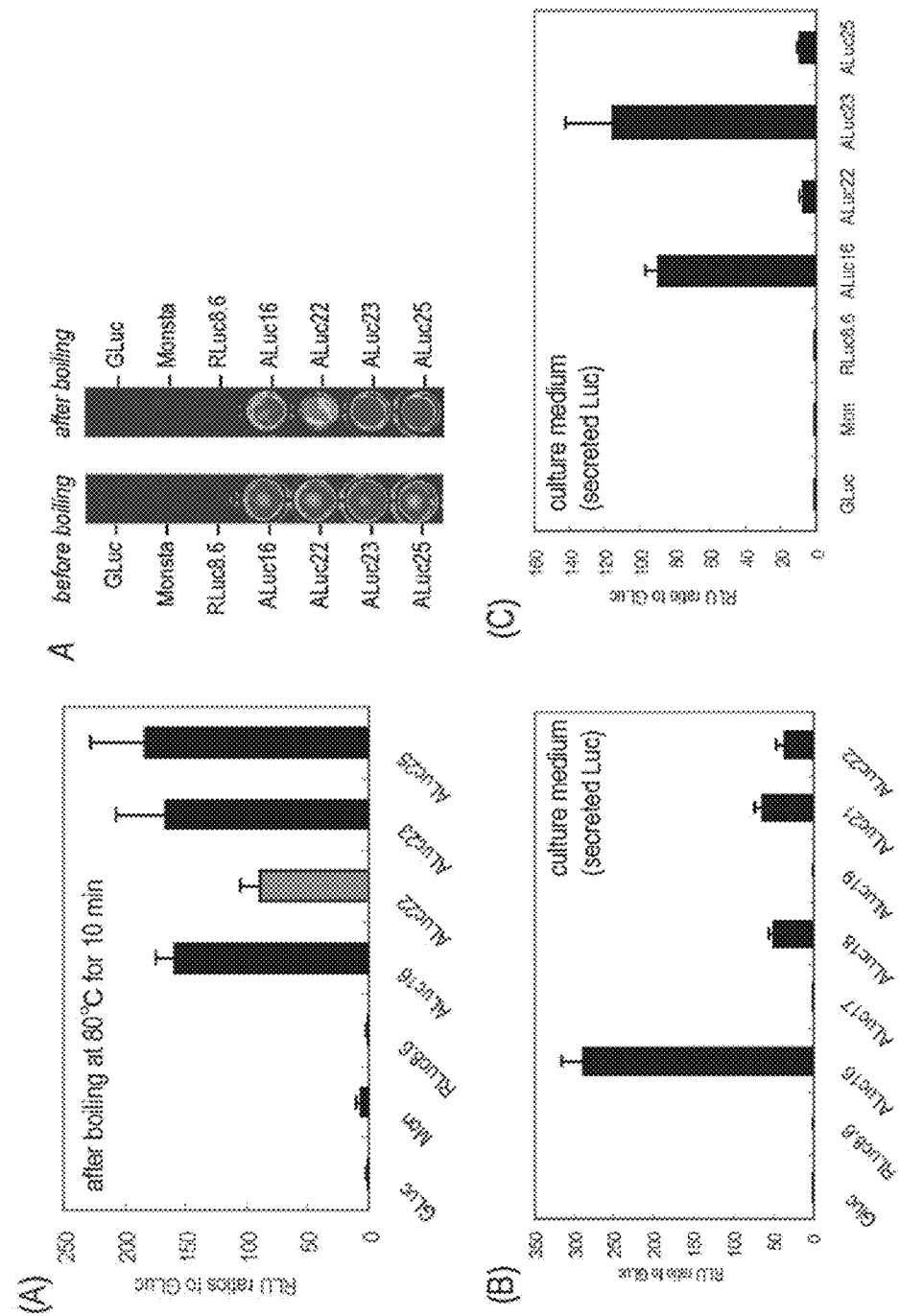
FIG. 4 Comparison of heat resistances and extracellular secretion degree of the artificial bioluminescent enzymes (ALuc). (A) Comparison of luminescence intensity of bioluminescent enzymes after heating at 80° C. for 10 minutes. The luminescence intensity of ALuc22 significantly decreased. The image on the right shows luminescence images before and after the heating. (B) Comparison of luminescent enzyme amounts in the culture medium. The extracellular secretion amount of ALuc16 was higher than those of other artificial bioluminescent enzymes. (C) Comparison of luminescent enzyme amounts in the culture medium. The extracellular secretion amounts of ALuc16 and ALuc23 were higher than those of the other artificial bioluminescent enzymes.
Figure 5:
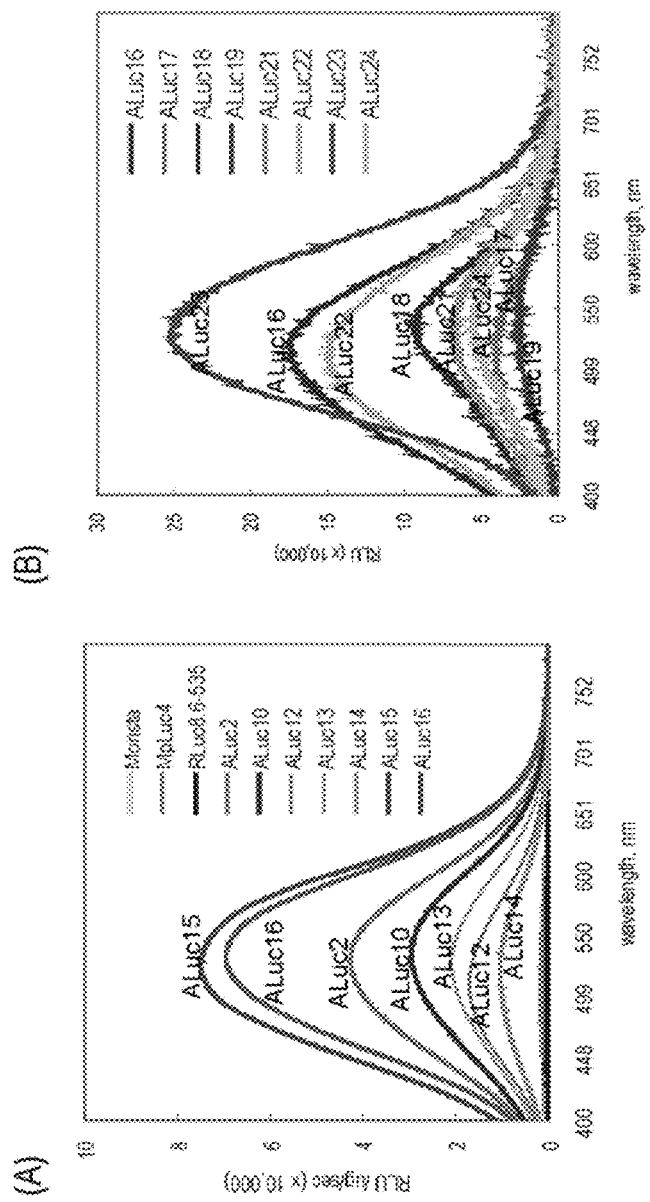
FIG. 5 Comparison of bioluminescence spectra of the artificial bioluminescent enzymes. (A) Luminescence spectra of artificial bioluminescent enzymes ALuc2 to ALuc16. (B) Luminescence spectra of artificial bioluminescent enzymes ALuc16 to ALuc24. Compared with known bioluminescent enzymes, these bioluminescent enzymes had luminescence spectra with significantly superior brightness and longer wavelength.

The heat resistance and degree of extracellular secretion of artificial luciferases of the present invention were measured (FIG. 4). First, to measure heat resistance, COS-7 cells containing each luciferase were lysed in cell lysis solutions produced by Promega to prepare lysates. Subsequently, same samples were allowed to stand at room temperature or heated at 80° C. for 10 minutes, and changes in luminescence intensity were compared by using a (substrate-containing) reaction solution produced by Promega.

The results confirmed that the luminescence intensity of ALuc22 was reduced by about 40% by heating. In contrast, in other luciferases (ALuc16, ALuc23, and ALuc25), a remarkable reduction in luminescence intensity that may be due to heating was not observed.

Further, each luciferase (ALuc) was introduced into COS-7 cells, culturing was performed overnight, and then the amount of each luciferase (ALuc) secreted from the cells was measured based on the luminescence intensity of the medium (FIG. 4B). The results confirmed that ALuc16 and ALuc23 showed relatively high extracellular secretion. In contrast, ALuc22, ALuc25, etc., showed strong luminescence, but showed low extracellular secretion and poor luminescence intensity from the media.

(Example 1-5) Red-Shifted Degree of Bioluminescence of Artificial Luciferases (ALucs) of the Present Invention The red-shifted degree of bioluminescence was measured based on the luminescence spectrum of each artificial luciferase (ALuc) of the present invention. First, each artificial luciferase (ALuc) was introduced into COS-7 cells, followed by culturing overnight. Subsequently, the cells were treated with a lysate produced by Promega for 20 minutes, and immediately after the introduction of a substrate-containing reaction solution produced by Promega to the 5 µL (FIG. 5A) or 2 µL (FIG. 5B) lysate, the spectra were measured by using a spectrophotometer (AB-1850, ATTO). The results indicated that many of the artificial luciferases (ALucs) of the present invention showed red-shifted luminescence spectra. The degree of the shift was such that ALuc15, ALuc16, ALuc23, etc., showed 50 to 80 nm red-shifted spectra as compared to the general spectrum peaks (470-480 nm) of conventional copepod luciferases.

The results indicated that when the ALuc of the present invention was used in bioimaging, it exhibited tissue transmittance with extremely high signal bioluminescence.

Figure 6:
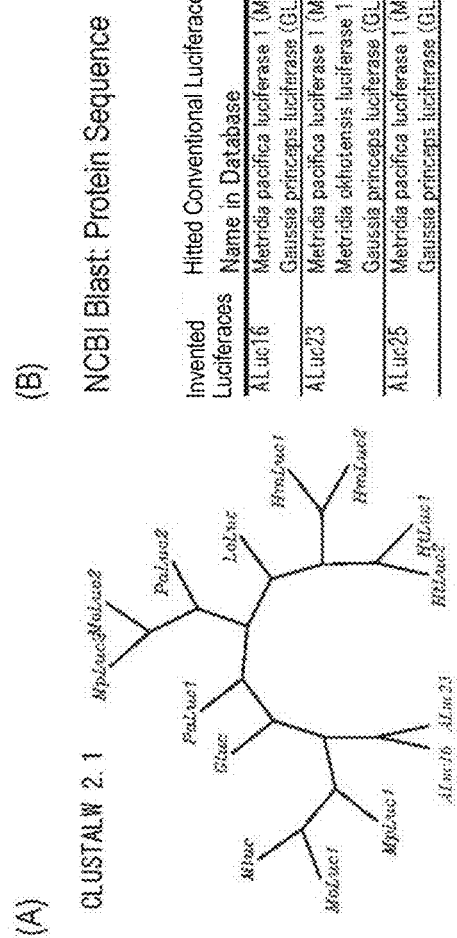
FIG. 6 Comparison regarding homology and similarity between amino acid sequences of existing luminescent enzymes derived from luminescent animals, and amino acid sequences of the novel artificial bioluminescent enzymes (ALuc). (A) Comparison regarding their sequence homology using CLUSTALW 2.1. (B) Comparison regarding their sequence similarity based on NCBI Blast. The above analyses found that the similarity with MpLuc1 was the highest, i.e., 83% and 72%. The similarity with MoLuc1 was the second highest, i.e., 74%.

(Example 1-6) Correlation and Similarity Between Artificial Luciferases (ALucs) of the Present Invention and Luciferases Derived from Known Luminescent Organisms The correlation and similarity between the amino acid sequences of the artificial luciferases (ALucs) newly synthesized in Examples 1-1 to 1-5 and the amino acid sequences of luciferases derived from known luminescent organisms were compared (FIG. 6).

First, the similarity between the ALucs of the present inventions and other luminescence enzymes was examined by using CLUSTALW2.1. The results indicated that the closest luciferase was MpLuc1, and MoLuc1 and MLuc also hit. According to the protein sequence comparison of NCBI Blast, ALuc23 had 83% similarity with MpLuc1, and 74% similarity with MoLuc1. The similar amino acid similarity measurement indicated that ALuc25 had the highest similarity with MpLuc1, and the homology was 72%.

Figure 7:
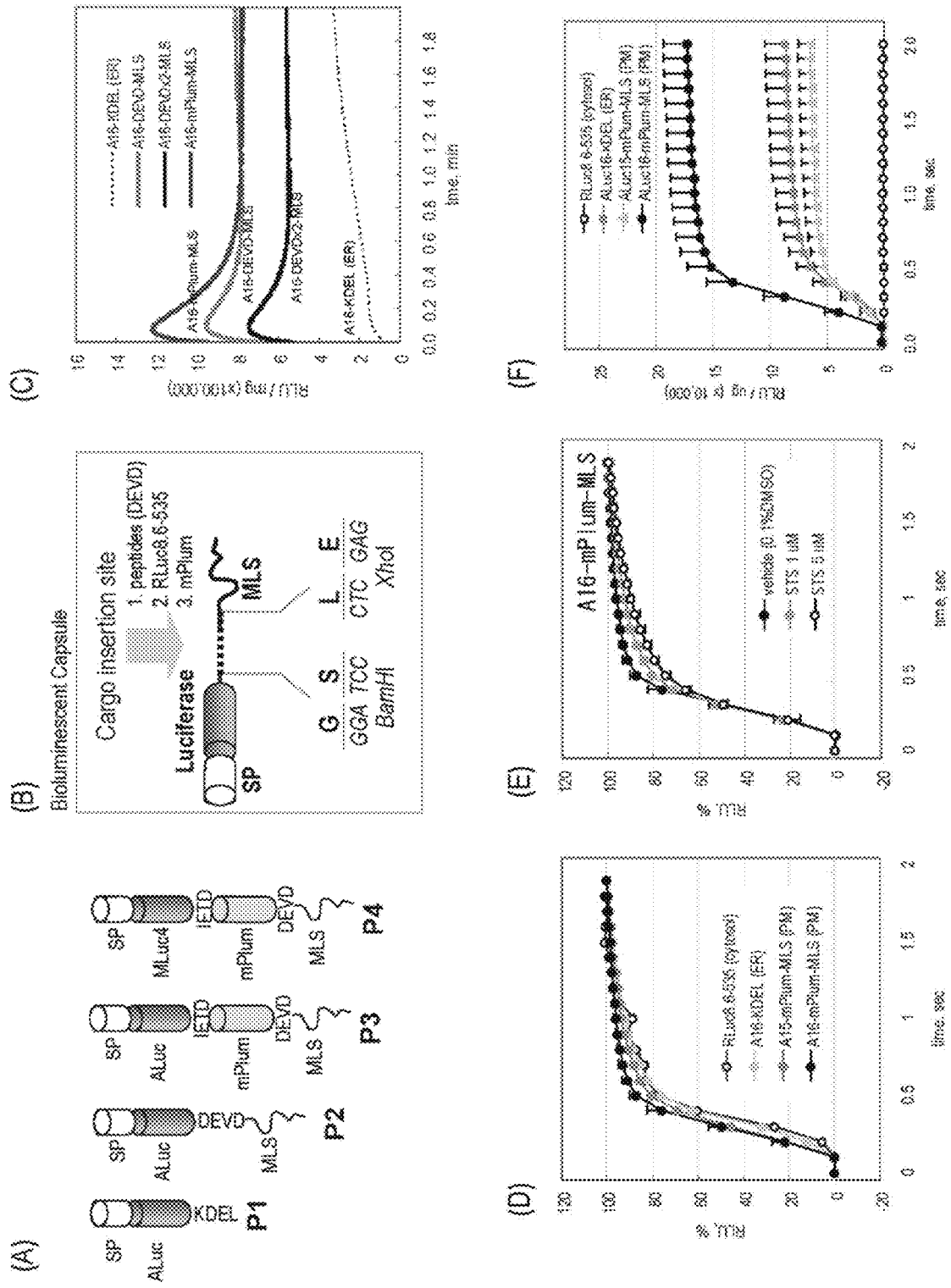
FIG. 7 Construction of a "luminescent capsule" probe having the artificial luciferase (ALuc) as its frame structure. (A) Molecular structure of the luminescent capsule. The luminescent capsule includes an extracellular secretion signal (SP), ALuc, an appropriate cargo protein (peptide), and a membrane localization signal. (B) Molecular structure of a generalized luminescent capsule. This luminescent capsule is designed to accept insertion of any kind of cargo protein. (C) Comparison of luminescence stability of the luminescent capsules. (D) Comparison of luminescence reaction rates of luminescent capsules having ALuc16. The reaction rate was increased in the case of membrane localization. (E) Luminescence reaction rates of luminescent capsules in the presence and absence of STS stimulation. (F) Comparison of luminescence stability of luminescent capsules using a microplate reader.

(Example 1-7) Construction of "Luminescent Capsule" Probe Containing Artificial Luciferase (ALuc) of the Present Invention in its Frame Structures A "luminescent capsule" probe containing the artificial luciferase (ALuc) of the present invention in its frame structure was developed (FIG. 7). The basic molecular structure of the luminescent capsule of the present invention comprises an extracellular secretion signal (SP), ALuc, a suitable cargo protein (peptide), and a membrane localization signal. Because of the SP, the probe is first transferred to the endoplasmic reticulum, and then transferred from the endoplasmic reticulum to the plasma membrane. This probe is designed to finally localize in the plasma membrane by the function of MLS (FIG. 7 AB).

The luminescent capsule has the ability to localize a fluorescence protein (mPlum), other luciferases (RLuc8.6-535), and a peptide (DEVD sequence, etc.) in the plasma membrane. The luminescence capsule containing fluorescent protein mPlum or peptide DEVD (substrate of caspase-3) was confirmed to exhibit excellent luminescence stability (FIG. 7C). In contrast, A16-KDEL (SEQ ID NO: 18), which is not a luminescent capsule structure, was localized in the endoplasmic reticulum and had poor luminescence intensity even though it carried the same ALuc16. The results indicated that the localization of the luminescent capsule in the plasma membrane allowed smooth supply of the substrate and oxygen, resulting in excellent luminescence stability and high luminescence intensity as described above. The luminescent reaction speed of the luminescent capsule after substrate injection was faster than those of other molecules (FIG. 7D). Further, the luminescent capsule containing a DEVE sequence (SEQ ID NO: 19) was confirmed to have a different luminescent reaction speed according to the presence or absence of a cell death-inducing chemical substance (STS) (FIG. 7E). The luminescence stability of the luminescent capsule was also confirmed by using a microplate reader for luminescence measurement (FIG. 7F).

(Example 1-8) Effect of Luminescent Capsule of the Present Invention

Figure 8:
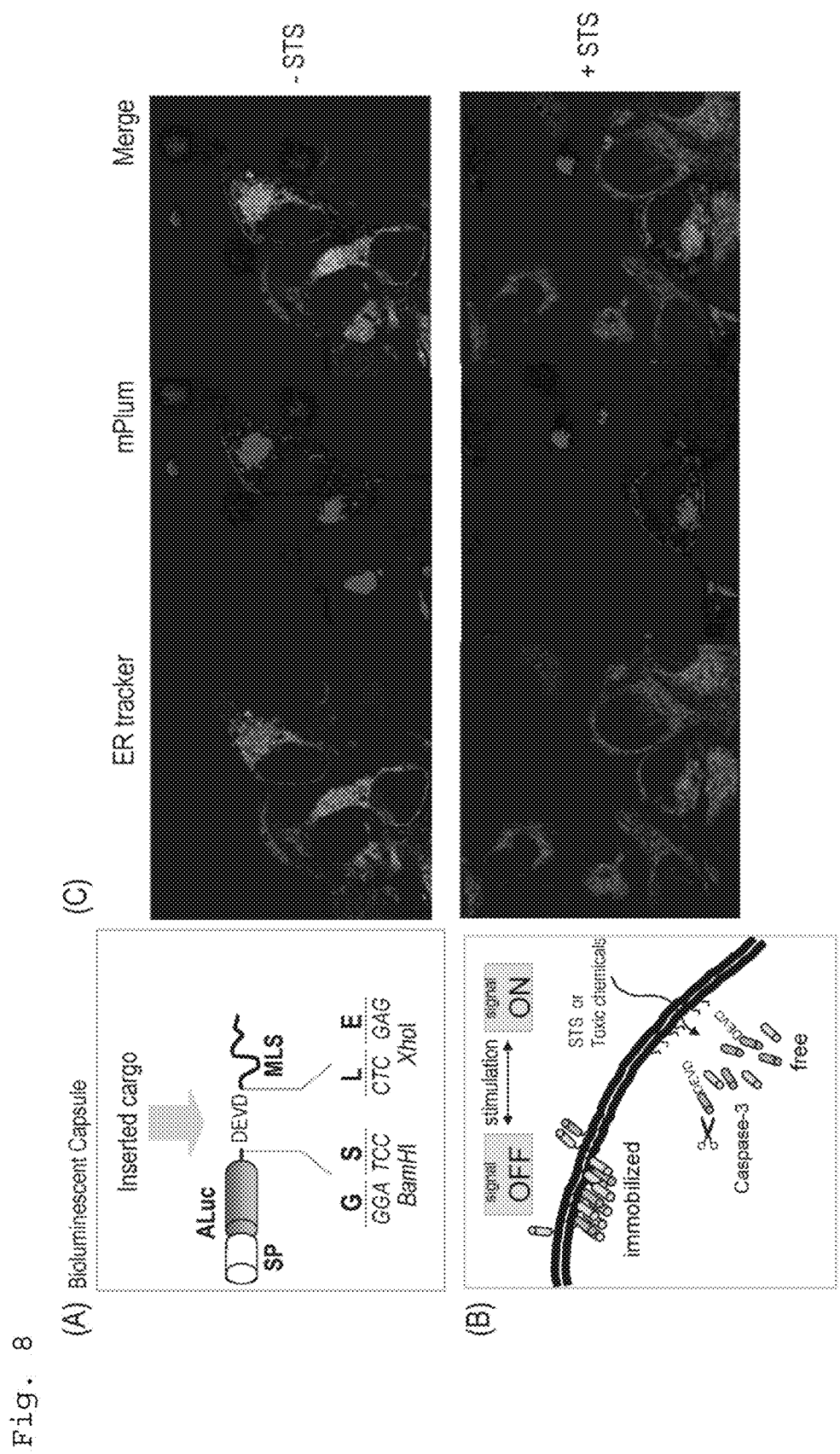
FIG. 8 Comparison of cell images before and after STS stimulation. (A) Molecular structure of a luminescent capsule. (B) Working mechanism of the luminescent capsule before and after STS stimulation. (C) Comparison of a luminescence image after STS stimulation with a luminescence image before STS stimulation. The light emission from the entire cytoplasm after the STS stimulation indicates decomposition of the luminescent capsule.

Effects of the luminescent capsule shown in Example 1-7 were evaluated by using a fluorescence microscope (Leica) (FIG. 8). First, a luminescent capsule (SEQ ID NO: 20) containing a conventional fluorescence protein, mPlum, was introduced into COS-7 cells, followed by culturing overnight. Cell images obtained after STS stimulation and without STS stimulation (control) were compared (FIG. 8C). Consequently, it was confirmed that the luminescent capsule was mainly localized in the plasma membrane before STS stimulation, and in the cytoplasm after STS stimulation. The results indicated that the luminescent capsule can measure an intracellular signal transduction process such as cell death with high sensitivity.

Figure 9:
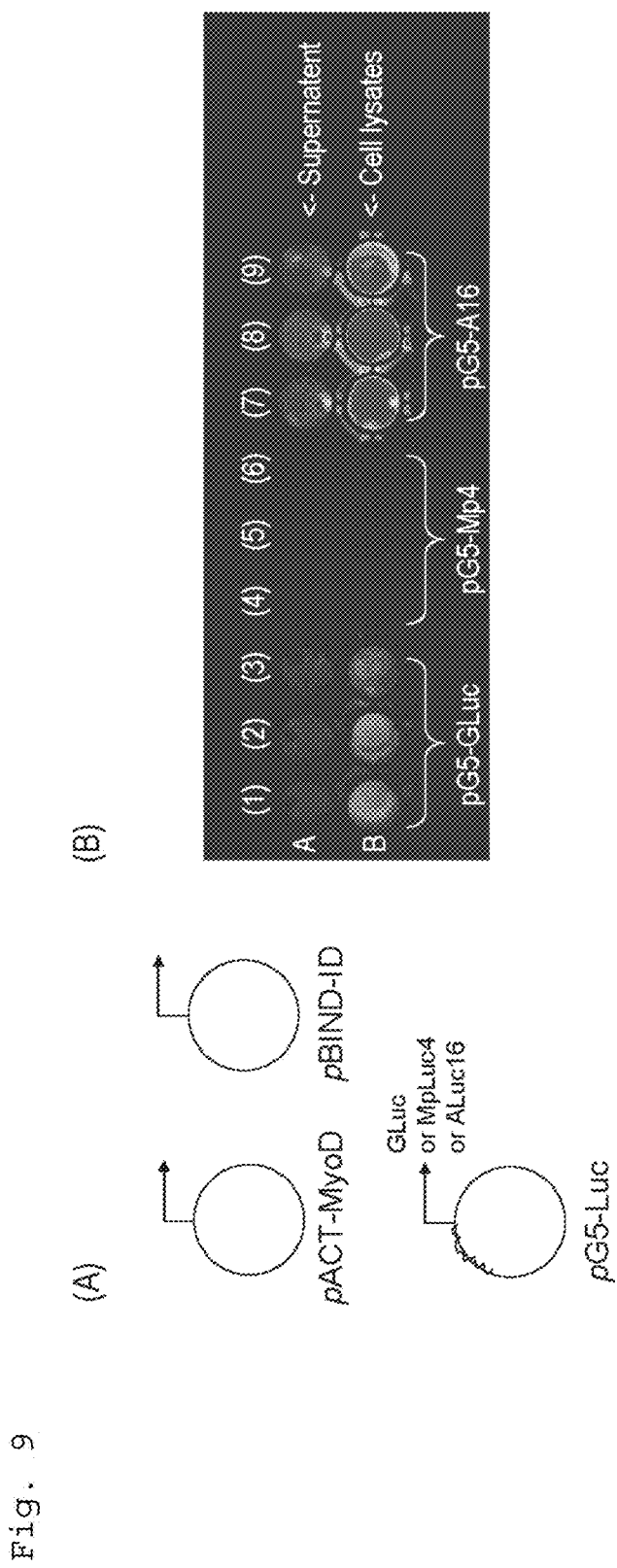
FIG. 9 Construction of a mammalian two-hybrid assay system using the artificial luciferase (ALuc) as a luminescence reporter. (A) Structure of a plasmid for constituting the two-hybrid assay system (B) Comparison of luminescence intensity of different reporters under equal conditions. The highest luminescence intensity was obtained when ALuc16 was used as a reporter.

(Example 1-9) Two-Hybrid Assay Using Artificial Luciferase (ALuc) of the Present Invention To demonstrate advantages of the artificial luciferase (ALuc) of the present invention as a luminescence reporter, ALuc was used as a reporter for a conventional mammalian two-hybrid assay system. First, using a known gene engineering technique, a novel reporter expression vector obtained by inserting a gene encoding MpLuc4 or ALuc16 into a commercially available reporter expression vector (pG5) was constructed. In addition, pG5-GLuc, which is the result of the researchers' previous study, was also prepared (FIG. 9A).

In addition to any one of the above three types of reporter expression vectors, a vector (pACT-MyoD) expressing a muscle regulatory factor (MyoD) and a vector (pBIND-ID) expressing a transcriptional regulator (ID) were cotransfected into COS-7 cells. After culturing overnight in a cell culturing device, a lysis solution and a substrate solution produced by Promega were used to cause a luminescent reaction, and difference in luminescence intensity varying according to the reporter difference was compared. The results of the comparison under the same conditions showed that the strongest bioluminescence was observed from the lysate containing the ALuc expression vector (FIG. 9B).

Along with the measurement, the luminescence value from the supernatant (medium) during cell culturing was simultaneously measured. As a result, slightly strong bioluminescence was observed when ALuc16 or GLuc was introduced. The results indicated that part of the luciferase was secreted out of the plasma membrane.

Figure 10:
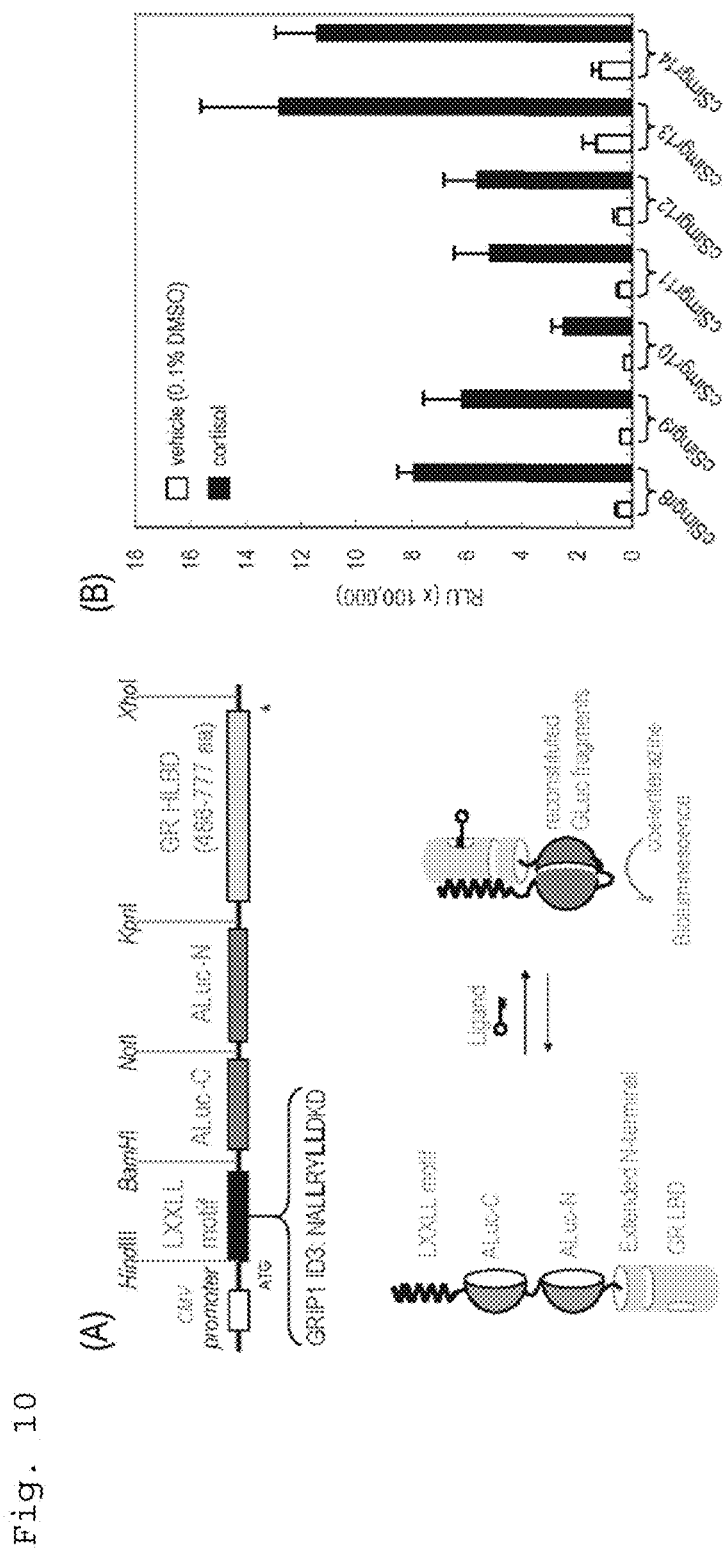
FIG. 10 A figure showing Example 1-10 in which measurement is performed using the luminescence measurement device of the present invention. Visualization of stress hormone activity using an integrated-molecule-format bioluminescent probe and the luminescence measurement device of the present invention. (A) The gene structure (upper drawing) and the working mechanism (lower drawing) of a bioluminescent probe used in the present example. In the presence of a stress hormone (cortisol), the molecular structure is folded, and luminescence is produced. (B) Comparison of S/N ratios in different bisection sites in the artificial luciferase (ALuc). cSimgr8 had a good S/N ratio, but a low absolute luminescence intensity. In contrast, cSimgr13 had a relatively low S/N ratio, but a high absolute luminescence intensity.

(Example 1-10) Development of Integrated-Molecule-Format Bioluminescent Probe Containing ALuc in its Frame Structure To demonstrate the advantages of ALuc, a series of integrated-molecule-format bioluminescent probes containing ALuc in its frame structure was developed (FIG. 10). FIG. 10A shows the gene structure. First, ALuc was bisected into two segments, and arranged right and left. A stress hormone receptor (glucocorticoid receptor ligand binding domain; GR HLBD) and its binding peptide (LXXLL motif) were respectively connected to the end of the two segments. As shown in the lower row of FIG. 10A, the working mechanism of the probe is such that a molecule is folded in the presence of a ligand, thus recovering the luminescence intensity.

In the bisection of ALuc16, the probes were named as cSimgr8 (SEQ ID NO: 21) to cSimgr14 according to its bisection point. The bisection point corresponding to each plasmid is as follows: cSimgr8 (125/126), cSimgr9 (129/130), cSimgr10 (133/134), cSimgr11 (137/138), cSimgr12 (137/138; containing a mutant at the joint portion), cSimgr13 (141/142), and cSimgr14 (146/147).

The results indicated that cSimgr13 and cSimgr14 showed good absolute luminescence intensity, and cSingr8 showed a good S/N ratio.

(Example 1-11) Measurement of Toxicity of Cytotoxic Substance (STS) Using Luminescence Measurement Device of the Present Invention A novel bioluminescence measurement device was developed for conducting a cytotoxicity detecting experiment (FIG. 11D). The structure of the device is explained below.

First, a microslide holder was treated with aluminum so that a commercially available microslide for cell culturing or for microscope observation (6-channel, produced by ibidi) fitted the holder. A platform was formed using, for example, a plastic material, so as to engage the microslide holder. Grooves were made in the sides of the slide holder or under the slide holder at certain intervals so that the microslide holder was nonslip on the platform at each interval. The platform was provided with engaging materials (e.g., spring balls) so that the platform engaged the grooves.

By covering the upper portion of the microslide for cell culturing with a honeycomb cap, optical interference between the channels of the microslide was blocked. The surface of the cap was made reflective to reflect light. The shape of the cap is not limited to a honeycomb shape as long as it can block optical interference between the channels of the microslide.

A filter holder (made of metal or the like) for including three optical filters was attached under the platform, and configured so that the slide filter holder was nonslip at the positions corresponding to each of the three optical filters.

A stand made of metal or the like was formed under the filter holder to withstand the weight in the upper portion. A hole was made in the stand, and the surface of the stand was made reflective by plating so that luminescence from the upper portion can reach the lower detection portion without optical loss. By attaching the stand of the luminescence measurement device of the present invention in place of the dish to a luminometer or a spectrophotometer, microslide measurement using a conventional luminometer or spectrophotometer can be easily performed.

Although a 6-channel microslide was used in FIG. 11D, more samples can be measured by increasing the number of channels under the same concept.

Figure 11:
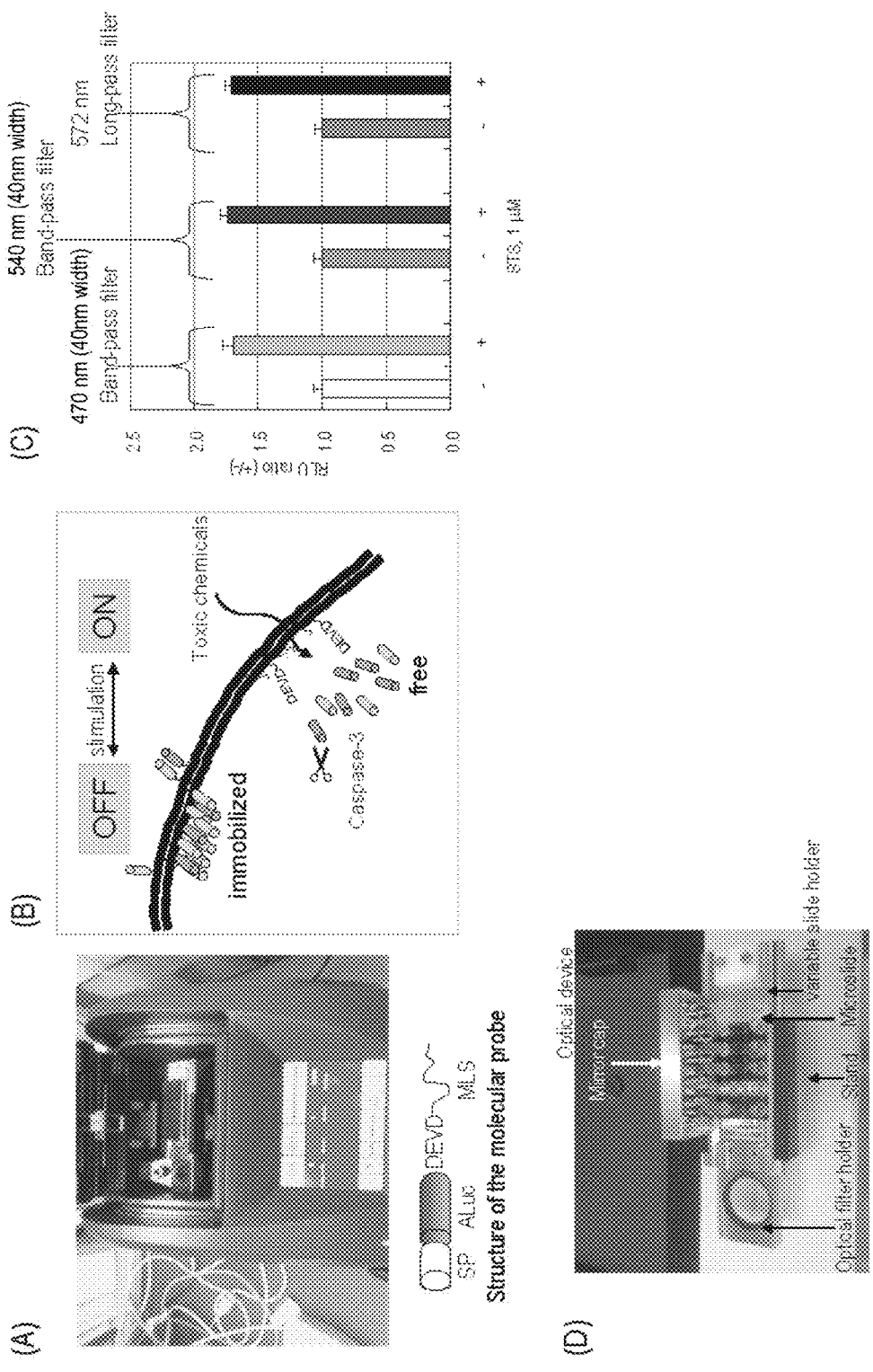
FIG. 11 A figure showing Example 1-11 in which measurement is performed using the luminescence measurement device of the present invention. (A) A photo of the luminescence device attached to a known luminometer. The drawing under the photo shows the structure of a molecular probe used in the present experiment. (B) A schematic diagram showing toxicity evaluation. The toxic substance causes decomposition of the probe, thereby temporarily increasing the luminescence value. (C) Evaluation of toxicity of chemical substance using the luminescence measurement device. An increase in luminescence value due to the "toxicity" of the chemical substance was observed. SP represents a secretion signal (secretion peptide). ALuc represents the artificial bioluminescence gene (artificial luciferase) of the present inventor. MLS represents a plasma membrane localization signal (membrane localization signal). (D) A high-accuracy bioluminescence measurement device produced for the present research. The device includes a microslide, a mirror cap, an optical filter, and a slide holder, and is designed to efficiently condense the luminescence signal.

Using the luminescence measurement device, the toxicity of a cell death-inducing chemical substance (STS) was measured (see FIG. 11). Monkey kidney-derived COS-7 cells were scattered in a commercially available microslide for cell culturing (produced by ibidi), and the cells were cultured until 90% of the microslide area was filled with the cells. The cells were transfected with a plasmid encoding a bioluminescence probe, followed by culturing for another 24 hours. The cells cultured in the microslide were stimulated with or without STS (final concentration: 1 μM) for 10 minutes (FIG. 11B).

The luminescence measurement was performed in the following manner. The microslide was washed once with an HBSS buffer, and a substrate-containing HBSS buffer (100 μL) was simultaneously introduced into each microslide channel, and the microslide was immediately fixed to the luminescent measurement device. After the device was covered with a mirror cap, the device was mounted on a conventional luminometer (GloMax 20/20n; Promega). The luminescence value was measured by changing the channels and the filters (three-second light condensation, n=3, see FIG. 11C).

The luminescence probe localized in the membrane was decomposed by Caspase-3 activated by STS to enhance luminescence intensity (FIG. 11B). Consequently, the luminescence intensity was increased by about 75%, and lights in the blue, yellow, red regions were effectively distinguished. In addition, since a very small error bar was shown, the measurement device was confirmed to be useful for quickly and accurately measuring the cytotoxicity of STS.

(Example 1-12) Measurement of Toxicity of Cell Death-Inducing Chemical Substance (STS) According to Change in Luminescence Spectrum Using Luminescence Measurement Device of the Present Invention (Measurement 1)

Figure 12:
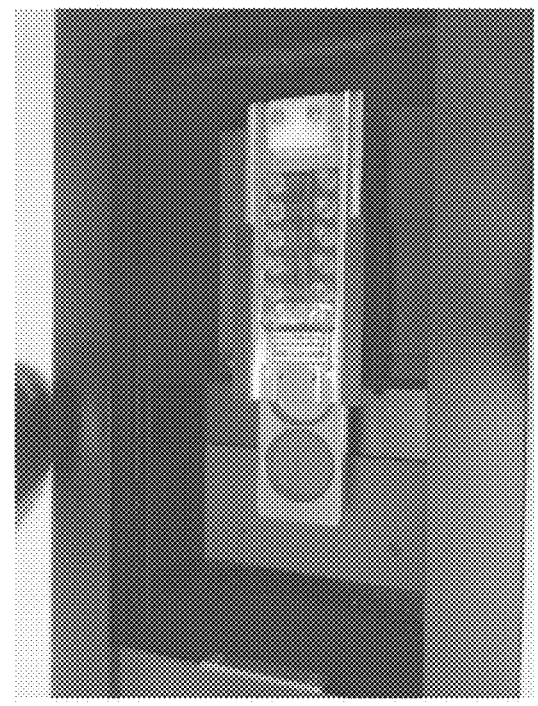
FIG. 12 A figure showing Example 1-12, which performs an evaluation of the harmful effect of a chemical substance by measuring the luminescence spectrum using the luminescence measurement device of the present invention. (A) A photo of the measurement device attached to a known spectrum meter. The lower drawing shows the structure of the molecular probe used in the present experiment. (B) The spectrum showing the actual measurement results.
Figure 12:
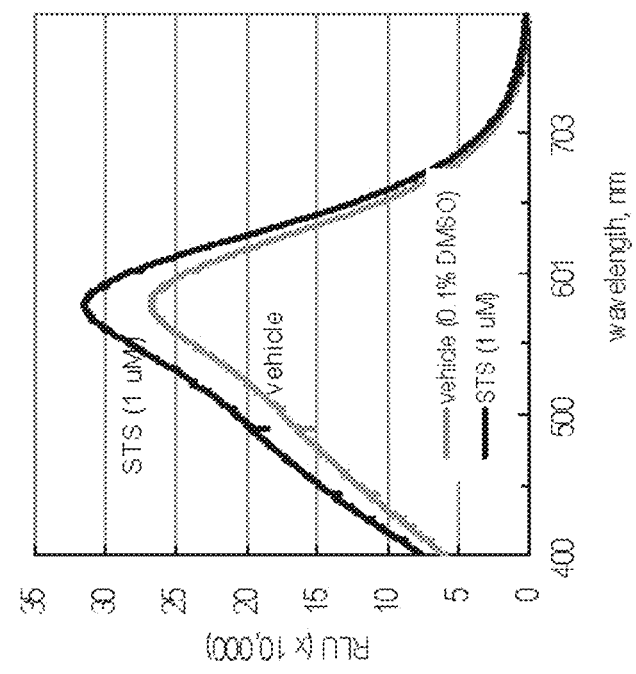

Using the luminescence measurement device of the present invention, the toxicity of a cell death-inducing chemical substance (STS) was measured based on changes in luminescence spectrum (see FIG. 12). First, monkey kidney-derived COS-7 cells were scattered in a commercially available microslide for cell culturing (produced by ibidi), and the cells were cultured until 90% of the microslide area was filled with the cells. The cells were transfected with a plasmid encoding a bioluminescence probe, followed by culturing for 24 hours. The cells cultured in the microslide were stimulated with or without STS (final concentration: 1 μm) for 10 minutes.

The luminescence measurement was performed in the following manner. The microslide was washed once with an HESS buffer, and a substrate-containing HBSS buffer (100 μL) was simultaneously introduced into each slide channel, and the microslide was mounted on the measurement device. After the device was covered with a mirror cap, the device was further mounted on a conventional spectrum meter (AB-1850; ATTO) (FIG. 12A). The luminescence spectrum from each channel was measured (two-minute light condensation, n=3, see FIG. 12B).

Consequently, an increase in the luminescence intensity in the full wavelength was observed in the case with STS (1 μM) stimulation compared to the case without STS stimulation. The maximum luminescence wavelength ($\lambda_{max}$) of the spectrum was 580 nm. About 26% of the total photons were photons greater than 600 nm, which corresponds to a so-called "optical window." The results indicated that the use of the probe or device in animal imaging can attain excellent tissue transmittance.

(Example 1-13) Cytotoxic Measurement Using Bioluminescent Capsule Containing ALuc16 in its Frame Structure (Measurement Example 2)

Figure 13:
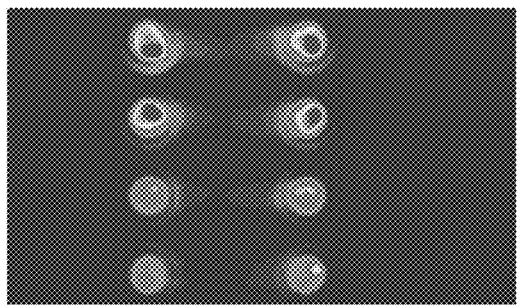
FIG. 13 A figure showing Example 1-13 in which measurement is performed using the luminescence measurement device of the present invention. (A) The light-condensing principle of the high-accuracy bioluminescence measurement device of the present invention. (B) The working mechanism of the cytotoxicity detection probe. The activity of caspase-3 in living cells increases due to a toxic substance (i.e., STS), thereby cutting the DEVD sequence. The image on the right shows an optical image of luminescence in response to STS. The bioluminescence was stronger in the presence of STS, compared with that in the absence of STS.
Figure 13:
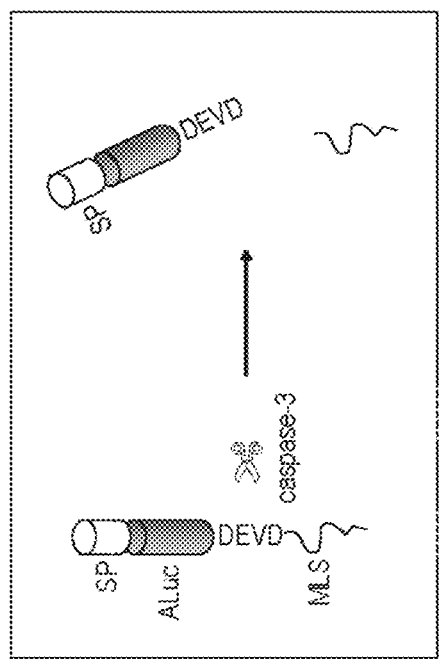
Figure 13:
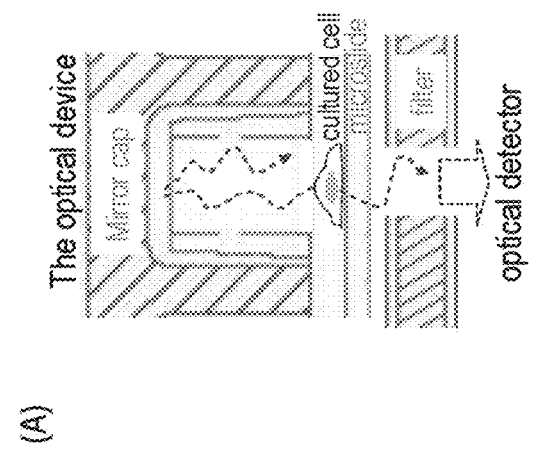

The cytotoxicity of a chemical substance was measured using the bioluminescent capsule (SEQ ID NO: 19) containing ALuc 16 in its frame structure (FIG. 13). First, COS-7 cells were cultured in a 6-channel microslide, and a gene encoding SEQ ID NO: 19 was introduced into the cells, followed by culturing for another 16 hours. Subsequently, the cells were stimulated for two minutes with or without the cytotoxic substance (STS), and the luminescence image showing a bioluminescence intensity difference in a substrate-containing solution was evaluated using an LAS-4000 (FujiFilm).

Consequently, the luminescence intensity of the right two channels was two folds higher than that of the left two channels. The results indicated that the luminescent capsule of the present invention can measure cytotoxicity with high sensitivity.

(Example 1-14) Measurement of Stress Hormone

Figure 14:
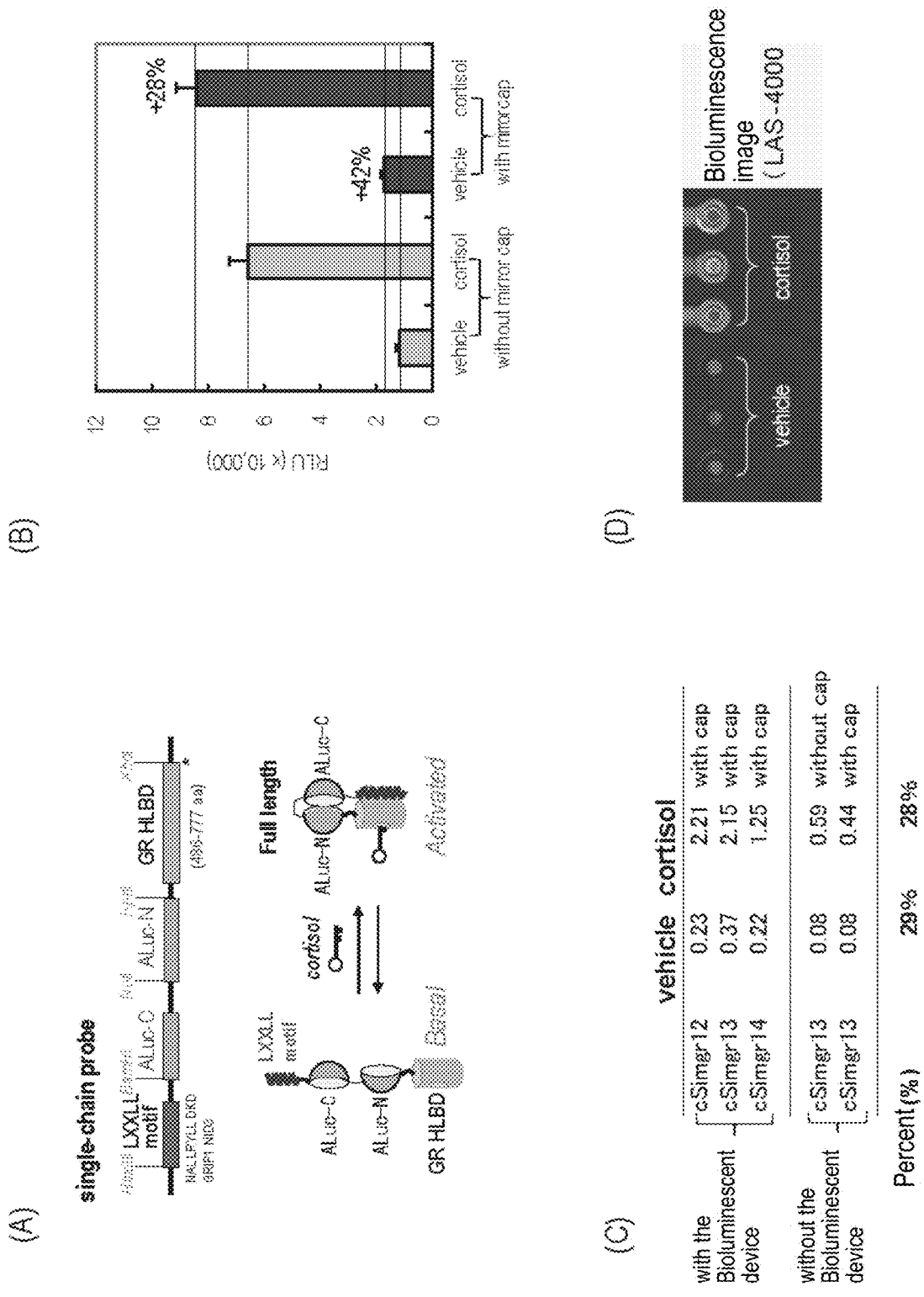
FIG. 14 Measurement of stress hormone using the luminescence measurement device. (A) The gene structure (upper drawing) and the working mechanism (lower drawing) of a bioluminescent probe used in the present example. In the presence of a stress hormone (cortisol), the molecular structure is folded, and luminescence is produced. (B) Comparison of luminescence light-condensing property in the presence and absence of a mirror cap. Since the luminescence value was higher with a mirror cap, the graph indicates the preferability of a mirror cap. (C) Comparison in standard deviation (SD) for the same sample in the presence and absence of a luminescence device. For the same sample, the standard deviation (SD) decreased to ⅓ or less when a luminescence device was used. This shows that the luminescence device increases the accuracy. (D) A luminescence image of the microslide. The luminescence was stronger in the presence of a stress hormone (the three channels on the right).

Stress hormone was measured using the luminescence measurement device of the present invention (see FIG. 14). African green monkey kidney-derived COS-7 cells were seeded in a 6-channel microslide (2.5×7.5 cm, μ-Slide VI$^{0.4}$; produced by ibidi), and cultured until 90% of the bottom volume was covered. The integrated-molecule-format bioluminescent probe (e.g., cSimgr13) as shown in FIG. 14A was introduced into the cells on the slide using a transfection lipid reagent (TransIT-LT1), followed by culturing for 16 hours. The left three channels of the microslide were stimulated in control solution-containing media. In contrast, a stress hormone standard solution ($10^{-5}$M) was introduced into the right three channels, followed by incubation for 20 minutes. Subsequently, all of the solutions in the microslide were removed, followed by washing once with a HESS buffer. Thereafter, a lysis solution produced by Promega was used to prepare a lysate, and an nCTZ-containing assay solution also produced by Promega was added thereto. The slide was mounted on the luminescence measurement device of the present invention, and the luminescence measurement device was further mounted on a luminometer (GloMax 20/20n, produced by Promega). The luminescence value in the presence or absence of a mirror cap was measured.

As a result, even when the same samples were used, an increase in luminescent value, i.e., from 28% (with stress hormone) to 42% (without stress hormone) was observed in the presence of the mirror cap, as compared with the case in the absence of the mirror cap (FIG. 14B). The results indicated that light was efficiently collected by the mirror cap.

In the stress hormone measurement using the same luminescence samples, the result analysis of FIG. 14C confirmed that the standard deviation (SD) in the presence of the luminescence device was small compared with the case in which the luminescent value was measured in the absence of the luminescence device. Specifically, even when the same samples were used, in the presence of the luminescence device, the measurement was conducted with high accuracy (from 28% (with stress hormone) to 29% (without stress hormone)), i.e., showing a standard deviation (SD) of ⅓ or less as compared to the case in the absence of the luminescence device. FIG. 14D shows the luminescence image of the microslide recorded by an LAS-4000.

(Example 1-15) Novel Single-Chain Antibody (scFv-ALuc16) Linked with Artificial Luciferase (ALuc)

Figure 15:
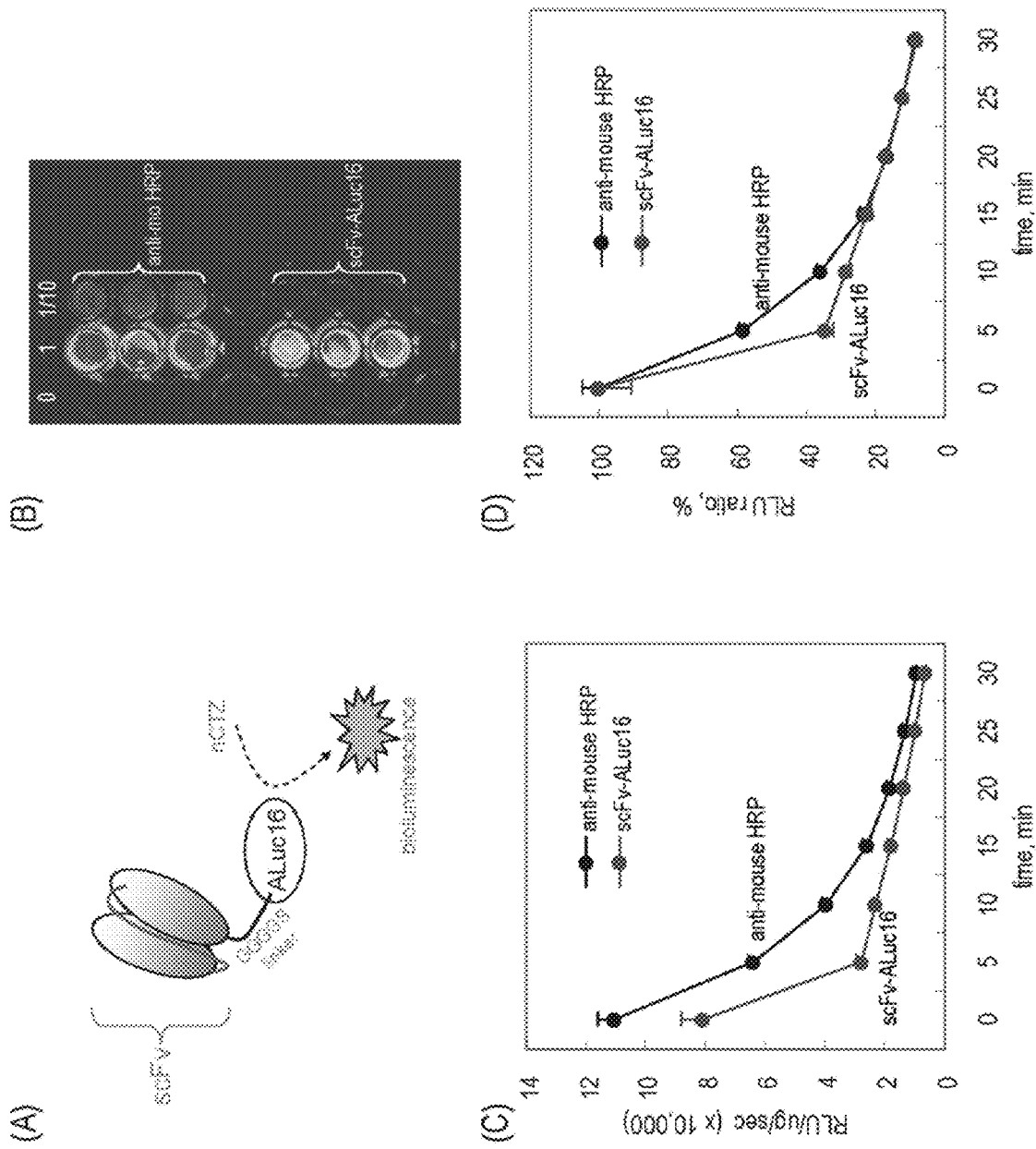
FIG. 15 Experiment for luminescence intensity comparison between an ALuc16-linked scFv antibody (scFv-ALuc16) and a horseradish-peroxidase (horseradish peroxidase; HRP)-linked anti-mouse antibody (GE Healthcare). (A) Molecular structure of scFv-ALuc16. (B) An image showing luminescence intensity measured by an LAS-4000. (C) Changes in luminescence intensity of the two antibodies over time. (D) Standardized changes in luminescence intensity of the two antibodies over time.

To demonstrate advantages of the artificial luciferase (ALuc) of the present invention as a luminescence pigment, a novel single-chain antibody (single-chain variable fragment; scFv) in which ALuc was linked with a GST tag antibody variable region fragment was experimentally produced (FIG. 15).

This trial product was obtained by linking the GST tag antibody variable region fragment with ALuc16 via a GGGGS linker using a gene engineering technique, and inserting the resultant into an *Escherichia coli* expression vector (FIG. 15A). After the expression in *Escherichia coli*, the resulting ALuc16-linked scFv antibody (scFv-ALuc16) was used to perform the luminescence intensity comparison experiment shown below.

An anti-mouse antibody (anti-mouse IgG; GE Healthcare) linked with commercially available horseradish peroxidase (HRP) was purchased, and prepared in a manner such that the concentration of HRP was 1 µg/mL. scFv-ALuc16 in the same amount as the HRP-linked anti-mouse antibody was prepared, and the solutions were individually injected, 10 µL per well, into the wells of a 96-well microplate.

Commercially available ImmunoStar LD (Wako) was prepared as the substrate solution for the HRP-linked anti-mouse antibody, while the substrate solution for scFv-ALuc16a was prepared using a *Renilla* luciferase assay kit produced by Promega. 90 µL per each of the prepared substrate solutions were simultaneously injected into a 96-well microplate using an eight-channel micropipette. The luminescence intensity and temporal change were measured using a luminescence image analyzer (LAS-4000, FujiFilm).

The results indicated that the HRP-linked anti-mouse antibody exhibited about 30% higher luminescence intensity (FIG. 15B). The scFv-ALuc16 showed a somewhat remarkable reduction in luminescence value within five minutes after substrate injection (FIG. 15CD). Regardless of this difference in luminescence intensity, the scFv-ALuc16 of the present invention was confirmed to exhibit strong bioluminescence, in conformation with the bioluminescence of conventional HRP.

Figure 16:
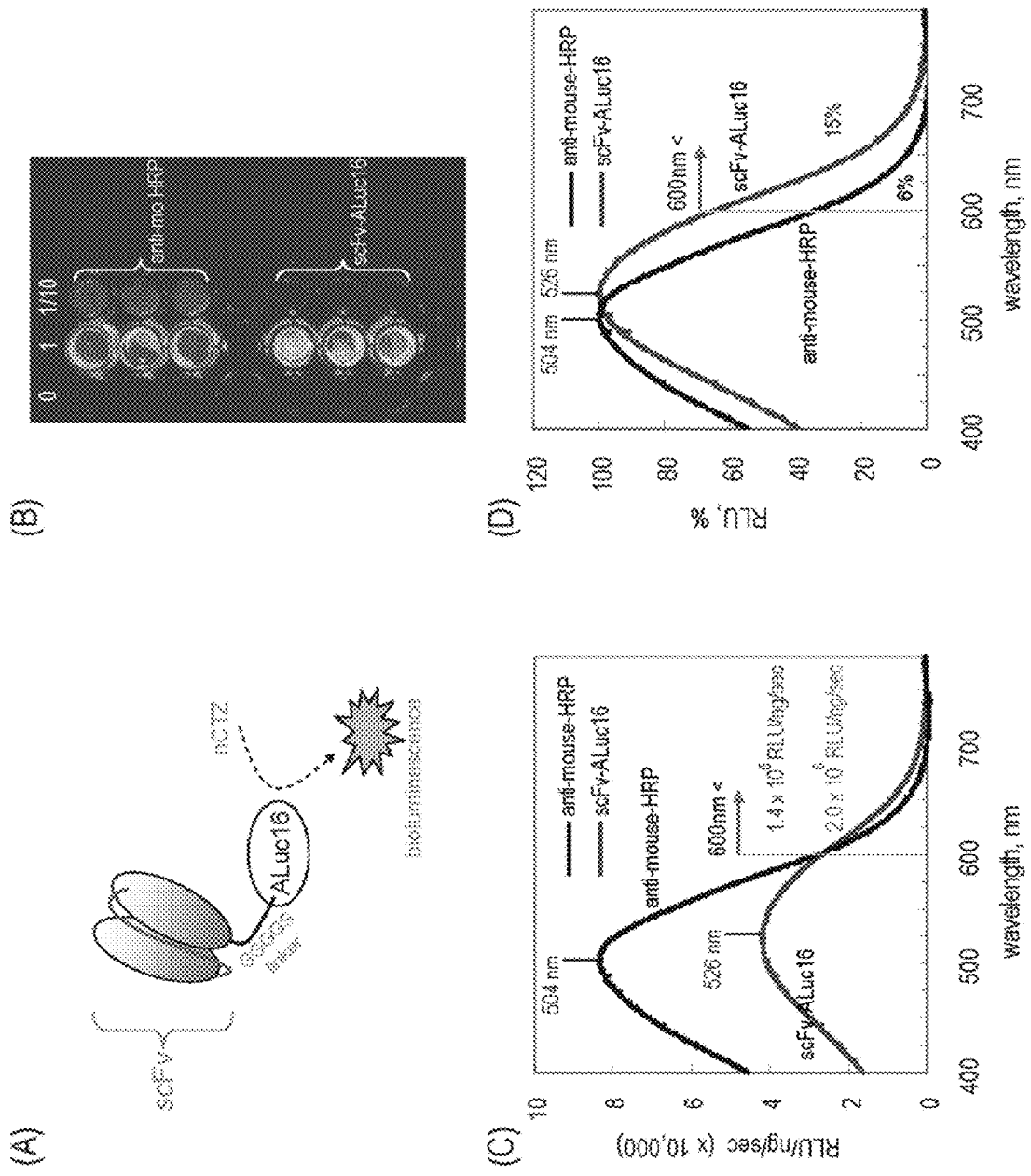
FIG. 16 Experiment for luminescence intensity comparison between an ALuc16-linked scFv antibody (scFv-ALuc16) and a horseradish peroxidase (horseradish peroxidase; HRP)-linked anti-mouse antibody (GE Healthcare). (A) Molecular structure of scFv-ALuc16. (B) An image showing luminescence intensity measured by an LAS-4000. (C) Comparison in absolute luminescence spectra between the two antibodies. (D) Standardized luminescence spectra of the two antibodies.

(Example 1-16) Luminescence Spectrum Comparison Between Novel Single-Chain Antibody (scFv-ALuc16) and Conventional HRP The following spectrum measurement was conducted to compare the luminescence spectra between scFv-ALuc16 and conventional HRP (FIG. 16). First, using the same process as in Example 1-15, scFv-ALuc16 (0.1 µg/mL) and a HRP-linked anti-mouse antibody (0.1 µg/mL) were prepared. 25 µL of each solution was individually injected into the wells of the 96 well-microplate. Further, 75 µL of each substrate solution, which was prepared in the same manner as in Example 1-15, was simultaneously injected using a 8-channel micropipette, and the luminescence spectra were measured using a highly sensitive spectrophotometer for luminescence (AB-1850, ATTO).

The results indicated that scFv-ALuc16 showed a more red-shifted luminescence spectrum than the HRP-linked anti-mouse antibody (FIG. 16CD): the values $\lambda_{max}$ of the HRP-linked anti-mouse antibody and scFv-ALuc16 were respectively 504 nm and 526 nm, and the percentages of luminescence in the wavelength region greater than 600 nm were respectively 6% and 15%. The results indicated that although scFV-ALuc16 exhibited slightly reduced luminescence intensity, it showed luminescence closer to the near-infrared region than HRP. This characteristic implies that the use of the antibody or ALuc16 in bioimaging can attain luminescence signals with high tissue transmittance.

Figure 17:
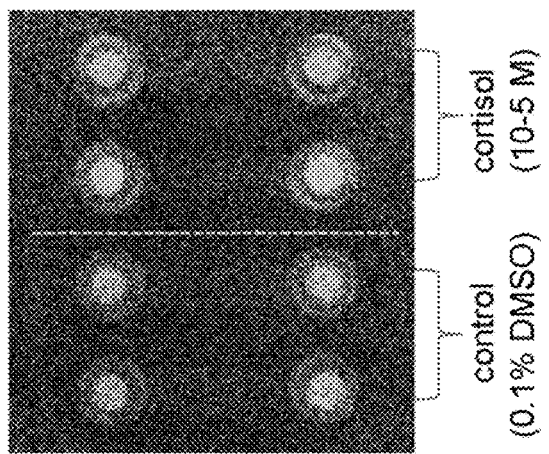
FIG. 17 Visualization of stress hormone activity using cSimgr13 (integrated-molecule-format bioluminescent probe; single-chain probe) that is stably expressed in an embryonic stem cell (ES cell). The bioluminescence intensity was higher in the two channels on the right under stress hormone stimulation, compared with the two channels on the left.

(Example 1-17) Application of Luminescence Probe Containing Luciferase (ALuc) of the Present Invention to ES Cell Novel ES cells expressing cSimgr13, which is an integrated-molecule-format bioluminescent probe containing the ALuc of Example 10 in its frame structure were established to visualize stress hormone sensitivity (FIG. 17). First, EB3 cells, which are feeder-free embryonic stem cells (ES), were cultured in a 10 cm dish, and then a pcDNA3.1 (+) vector encoding cSimgr13 was introduced into the EB3 cells. In the presence of G418, transformed cells stably expressing cSimgr13 were established.

One day after the subculturing of the transformed cells in a microslide, some of the cells in the wells were used as a control (0.1% DMSO), and the others were stimulated with $10^{-5}$ M stress hormone (cortisol) for 20 minutes. Subsequently, after lysis, the cells were illuminated using a substrate-containing assay buffer in accordance with the protocol of luminescence assay kit produced by Promega, and the luminescence intensity was measured using an LAS-4000. Consequently, the group stimulated with stress hormone showed stronger luminescence than the control. The results indicated that the luminescence probe based on the luciferase (ALuc) of the present invention is also applicable to embryonic stem cells (ES), and does not lose hormone recognition ability.

(Example 1-18) Production of Additional Artificial Luciferases ALuc25 to ALuc32

Additional functional artificial luciferases were developed based on the research and development results. Based on ALuc25, sequences having a large hydrophilic amino acid proportion and a small hydrophilic amino acid proportion were produced, and named ALuc26, ALuc27, ALuc28, and ALuc29. In addition, artificial luciferases having an antigen recognition site (epitope; examples including His tag, Myc tag, etc.) in the sequence were developed, and named ALuc30 (containing a His tag in the sequence), ALuc31 (containing an His tag in the sequence), and ALuc 32 (containing a Myc tag in the sequence) (FIG. 18).

After the insertion of a gene encoding an enzyme sequence as mentioned above into a mammalian expression vector (pcDNA3.1 (+)), each plasmid was introduced into COS-7 cells. By the transformation of these cells, each luciferase was expressed, and some of the luciferase was secreted out of the cells and some of the luciferase retained in the cells. 20 hours after the plasmid introduction, media of the cells were sampled, and the remaining cells were lysed with a lysis buffer (lysate preparation). Immediately after 50 µL of assay solution (containing a substrate) was simultaneously added to each prepared medium (5 µL) or lysate (5 µL), the luminescence value was measured using a luminescence analyzer (LAS-4000; FujiFilm) (n=3) (FIG. 18).

Consequently, the luminescence values extremely higher than those of conventional GLuc and MpLuc4 were observed from the lysates of ALuc25, ALuc30, and ALuc31. In the cell medium group, strong bioluminescence was observed from the cell medium containing ALuc30 or ALuc31. The results indicated that ALuc30 and ALuc31 were better if strong bioluminescence from both conditions, i.e., the lysate and medium, were desired. In addition, since ALuc30 and ALuc31 contain an His tag in the sequence (FIG. 18 (A)), they can be used as luminescent labels in a wide range of bioassay fields, including purification using His tag chromatography, use of an antibody containing an His tag sequence as an antigen recognition site, etc. (FIG. 18 (B))

Figure 18:
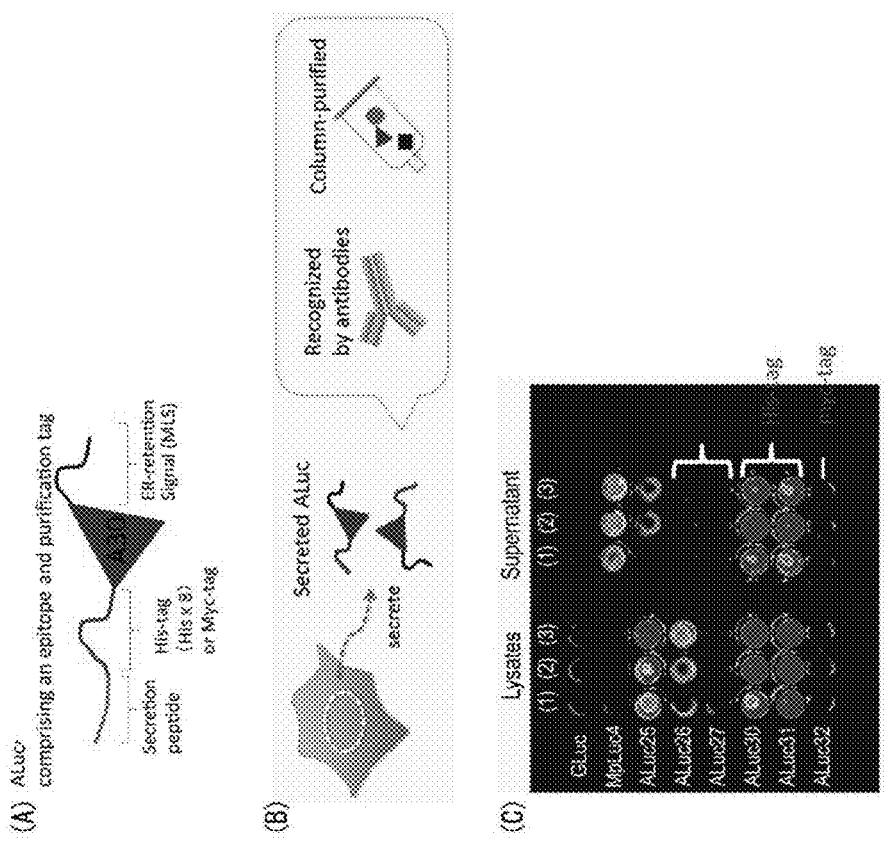
FIG. 18 Establishment of functional artificial bioluminescent enzymes Molecular structure of novel bioluminescent enzyme (ALuc30). The sequence includes an His-tag sequence (antigen recognition site) that enables visualization of the enzyme by using column purification or an antibody after its secretion in the culture medium. (B) Working mechanism of the functional bioluminescent enzyme. The mechanism shows that ALuc is secreted as it is expressed as a reporter, thereby allowing confirmation using other means. (C) Comparison of relative luminescence intensity of functional artificial bioluminescent enzymes. ALuc25, ALuc30, and ALuc31 have relatively high luminescence intensity.
Figure 18D:
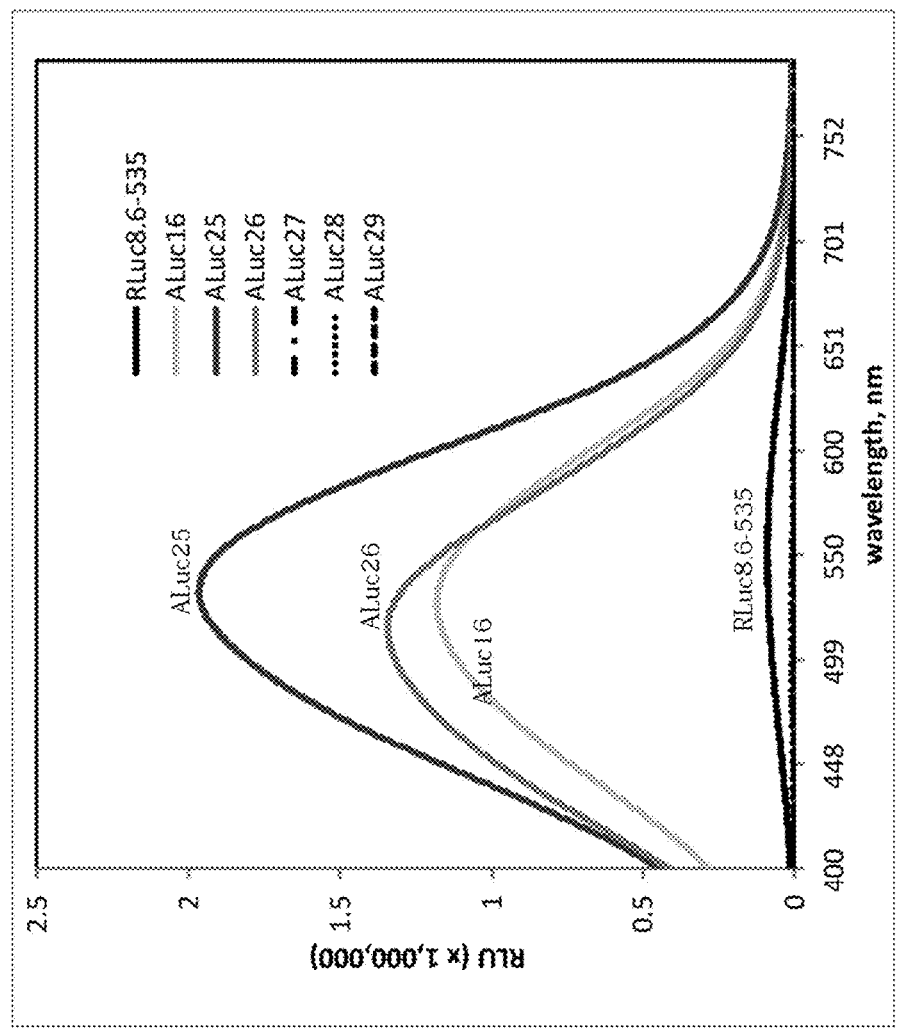
FIG. 18D A graph showing bioluminescence spectra of ALuc25 to ALuc29.
Figure 18E:
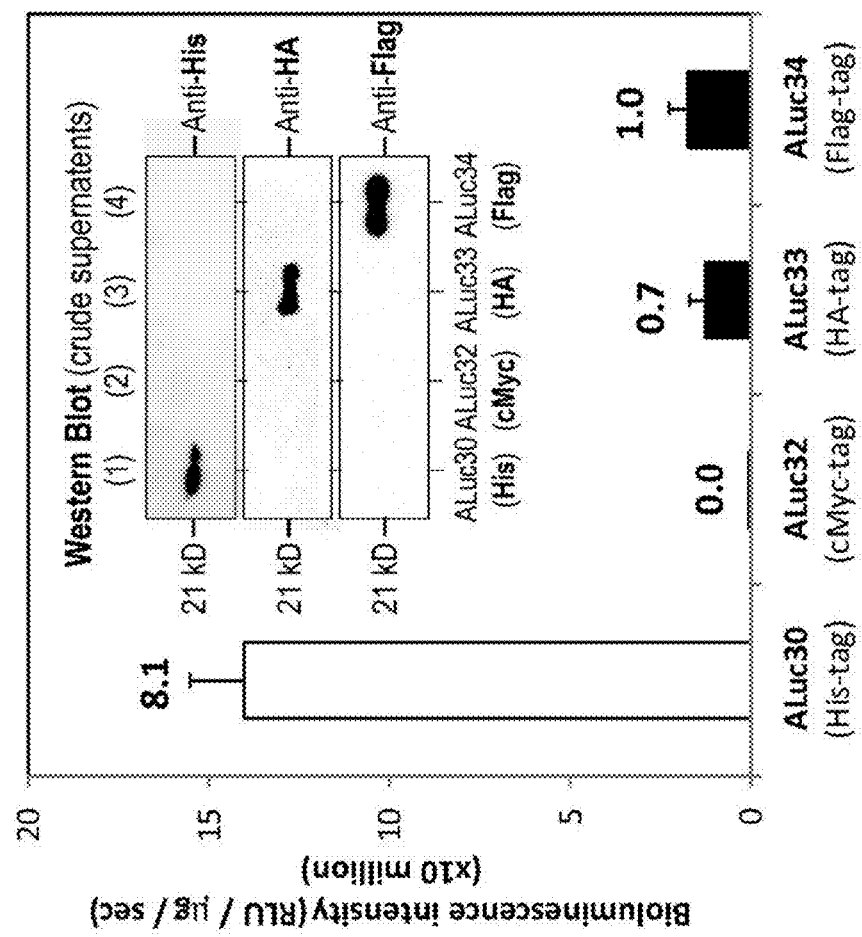
FIG. 18E Confirmation of expression of artificial bioluminescent enzymes including a tag by western blotting, and confirmation of their functions by column purification. Each artificial bioluminescent enzyme is secreted from the cells in the medium. It was confirmed that by purifying each medium using Ni-NTA affinity column chromatography, it is possible to selectively extract ALuc30 including an His-tag. The graph shows the results of western blotting using dedicated antibodies. The graph shows that each artificial bioluminescent enzyme (ALuc30, ALuc33, and ALuc34) was secreted in each culture medium, and that the functions of the tags were therefore confirmed.

FIG. 18 (D) shows the bioluminescence spectra of ALuc25 to 29.

Properties of the tag-including artificial luciferases after expression were evaluated using conventional Western blotting and affinity chromatography (FIG. 18 (E)).

First, each of the expression vectors of luciferases ALuc30 to 34 was introduced into COS-7 cells. One night after expression induction, the cell media were collected, and the presence of absence of secretion and the molecular weight of each expressed luciferase were respectively confirmed using affinity chromatography and Western blotting (FIG. 18 (E), inserted figure).

The results found that His tag-containing ALuc30 was selectively extracted when each medium was purified using Ni-NTA affinity chromatography. The results of Western blotting using special antibodies (His tag antibody, HA tag antibody, Flag tag antibody) confirmed that the artificial luciferase (ALuc30, ALuc33, or ALuc34) was secreted in each medium and each tag functioned from the location of the band (indicating molecular weight) and the concentration of the band (indicating expression amount).

(Example 1-19) Prolonged Stability of Artificial Luciferase

Figure 19:
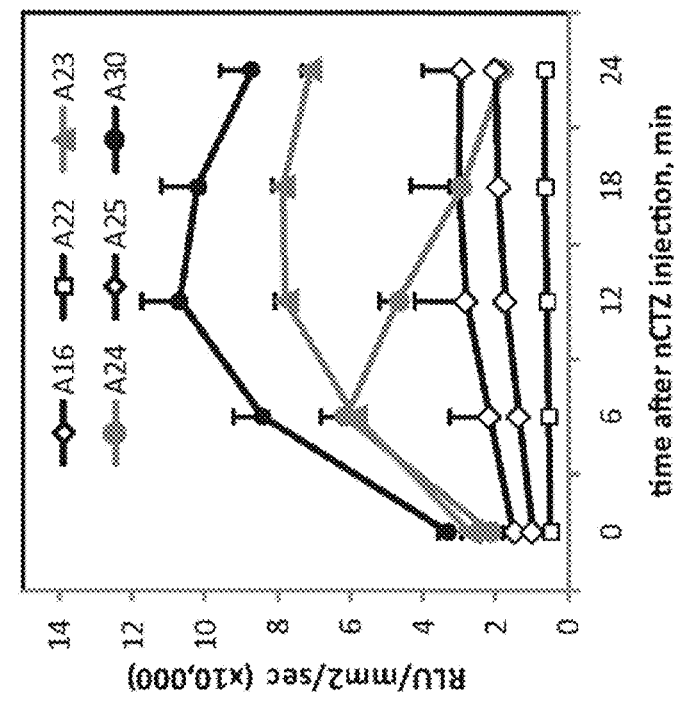
FIG. 19 Long-term stability of artificial bioluminescent enzymes (ALuc). (A) Stability of luminescence activity of ALucs secreted in cell culture media. The luminescence activity was measured after 25 days. The results revealed that ALuc16 decreased to 20% of its original activity, while ALuc30 and ALuc25 maintained 50-60% of the original activity. (B) Changes in ALuc activity over time after long-term conservation (25 days). The luminescence values of ALuc23 and ALuc30 were at maximum 12 minutes after infusion of coelenterazine. ALuc24 had an abrupt increase in luminescence value after 6 minutes.
Figure 19:
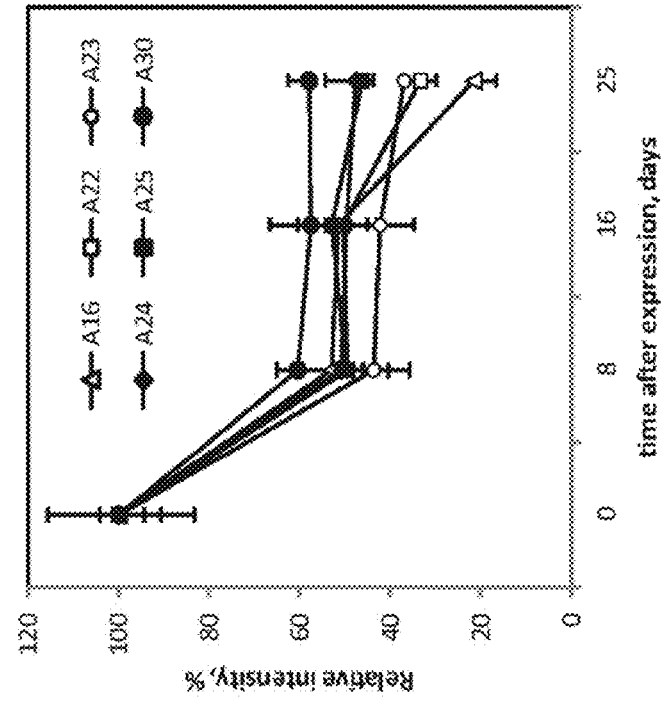

The prolonged activity stability of the artificial luciferases (ALucs) developed in the present invention was examined. First, a plasmid expressing each artificial luciferase (ALuc16, ALuc22, ALuc23, ALuc24, ALuc25, and ALuc30) (in the figure, each is referred to as A16, A22, A23, A24, A25, and A30) was introduced into COS-7 cells, and then culturing was continued for 24 hours. By the culturing, each artificial luciferase was secreted into the medium. The artificial luciferase secreted in the medium was collected, and a difference in enzymatic activity was measured under the same conditions in the following manner. On the first day (Day 0), 50 µL of assay solution (containing native coelenterazine, produced by Promega) was added to 5 µL of each medium, and the luminescence value (enzymatic activity) was measured using an LAS-4000 (produced by FujiFilm). In the same manner, the luminescence value on Day 8, Day 16, and Day 25 was compared with the luminescence value on Day 0 (FIG. 19 (A)). Consequently, ALuc16 and ALuc22 showed a significant decrease in enzymatic activity; however, ALuc24, ALuc25, ALuc30, etc., maintained stable enzymatic activity until Day 25. In particular, ALuc30 was found to maintain about 60% of the initial enzymatic activity for a long period of time.

For the medium samples 25 days after expression, temporal changes in luminescence intensity after substrate injection were observed in the following manner (FIG. 19(B)). 50 µL of an assay solution (containing native coelenterazine, produced by Promega) was added to 5 µL of each medium 25 days after the expression, and the luminescence value (enzymatic activity) was measured using an LAS-4000 (produced by FujiFilm). Consequently, a phenomenon in which the luminescence value was gradually increased was observed in all artificial luciferases. In particular, 12 minutes after the injection, ALuc23 and ALuc30 showed luminescence intensity several times higher than that obtained at the time of injection.

The results indicated that the artificial luciferases of the present invention had excellent prolonged storage stability, because a remarkable inactivation phenomenon was not observed even after refrigerated storage for 25 days.

(Example 1-20) Living Cell Imaging Using ALuc of the Present Invention

Figure 20:
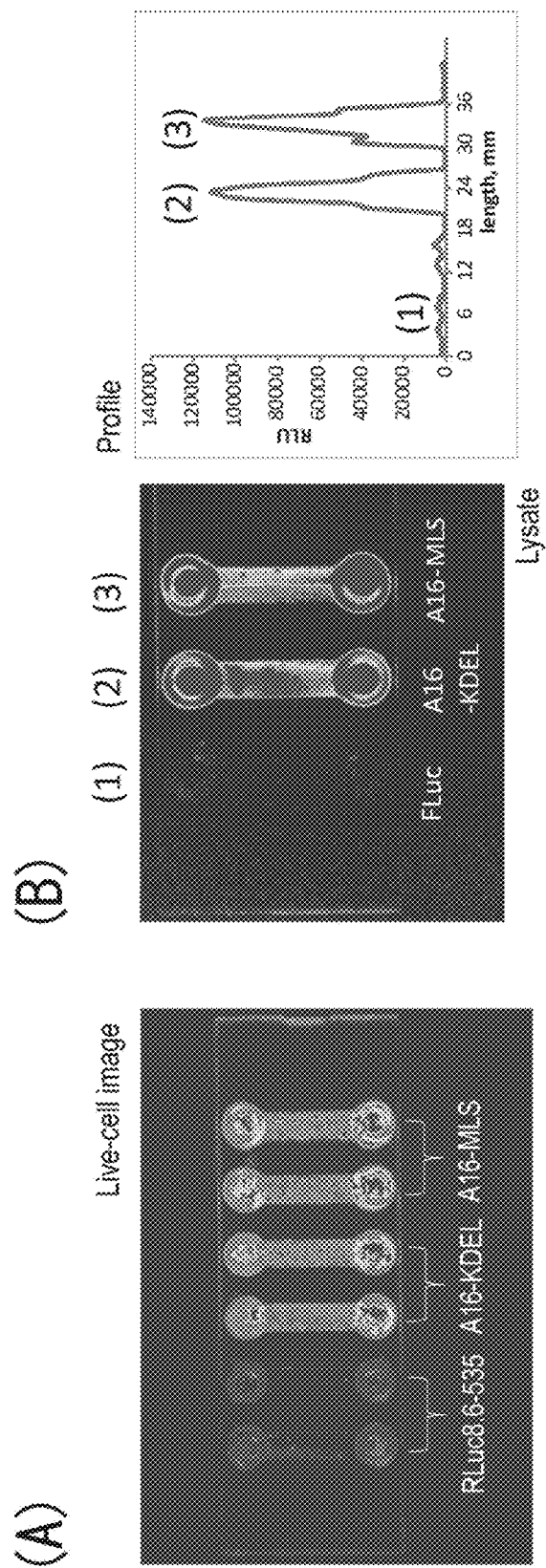
FIG. 20 A living cell image and a luminescence profile obtained by using the artificial bioluminescent enzyme.
(A) A luminescence image of COS-7 cells cultured on a microslide. A significant luminescence image was observed only in living cells expressing ALuc (A16). (B) Luminescence image (left) and a luminescence profile (right) of a COS-7 cell lysate cultured on a microslide.

The following experiment was conducted to examine the living cell imaging abilities of the artificial luciferases established in the present invention (FIG. 20).

First, COS-7 cells were cultured in a microslide produced by ibidi. After the cells were raised to a certain level, the following genes were transferred to the cells in the channels. Channel group 1: pcDNA3.1 plasmid having a gene encoding a luminescent enzyme derived from *Renilla reniformis* (RLuc8.6-535); Channel group 2: pcDNA3.1 plasmid having a gene encoding A16-KDEL; and Channel group 3: pcDNA3.1 plasmid having a gene encoding a luminescent capsule based on ALuc16 (i.e., A16-MLS).

After gene transfer, culturing was performed for another 16 hours. Immediately before imaging, the medium was substituted with an HBSS buffer containing a substrate, and the luminescence image obtained after the substitution was measured using an LAS-4000 (FujiFilm).

Consequently, almost no luminescence image was obtained from the channels expressing RLuc8.6-535; however, a strong luminescence image was observed from the channels expressing A16-KDEL or A16-MLS (FIG. 20A). The results indicated that the artificial luciferases of the present invention were excellent in living cell imaging compared to conventional luminescent labels. This is presumably because the luminescence intensity of the artificial luciferases of the present invention is strong. The artificial luciferases are therefore advantageous in cell imaging even when they are used in small amounts.

Similarly, COS-7 cells were cultured in a microslide produced by ibidi. After the cells were raised to a certain level, the following genes were transferred to the cells in the channels. Channel group 1: pcDNA3.1 plasmid having a gene encoding *Cypridina* luciferase; Channel group 2: pcDNA3.1 plasmid having a gene encoding A16-KDEL; and Channel group 3: pcDNA3.1 plasmid having a gene encoding a luminescent capsule based on A16 (i.e., A16-MLS).

After gene transfer, culturing was performed for another 16 hours. 20 minutes before imaging, 40 µL of a lysate buffer produced by Promega was added, and the resultant was allowed to stand for 20 minutes. Further, a substrate-containing assay buffer produced by Promega was added to the medium of each channel, and the luminescence image obtained after the addition was measured using an LAS-4000 (FujiFilm).

Consequently, strong luminescence was only observed in channels of A16-KDEL and A16-MLS (FIG. 20B, left). Such luminescence intensity difference was clearly confirmed by the luminescence intensity profile (FIG. 20B, right).

(Example 1-21) Establishment of Functional Artificial Luciferases (ALuc 30-34) Having Antigen Recognition Site (Epitope)

Providing the artificial luciferase (ALuc) with functionality (antigen recognition ability, affinity chromatography purification ability) is an essential feature for the versatility of luminescent enzymes. To achieve this object, a series of artificial luciferases including a tag in part of the sequence of each artificial luciferase established in the present invention were established. These luciferases have a feature in that they contain an antigen recognition site (which can be also used for affinity chromatography purification) at an appropriate position in the sequence.

Figure 21:
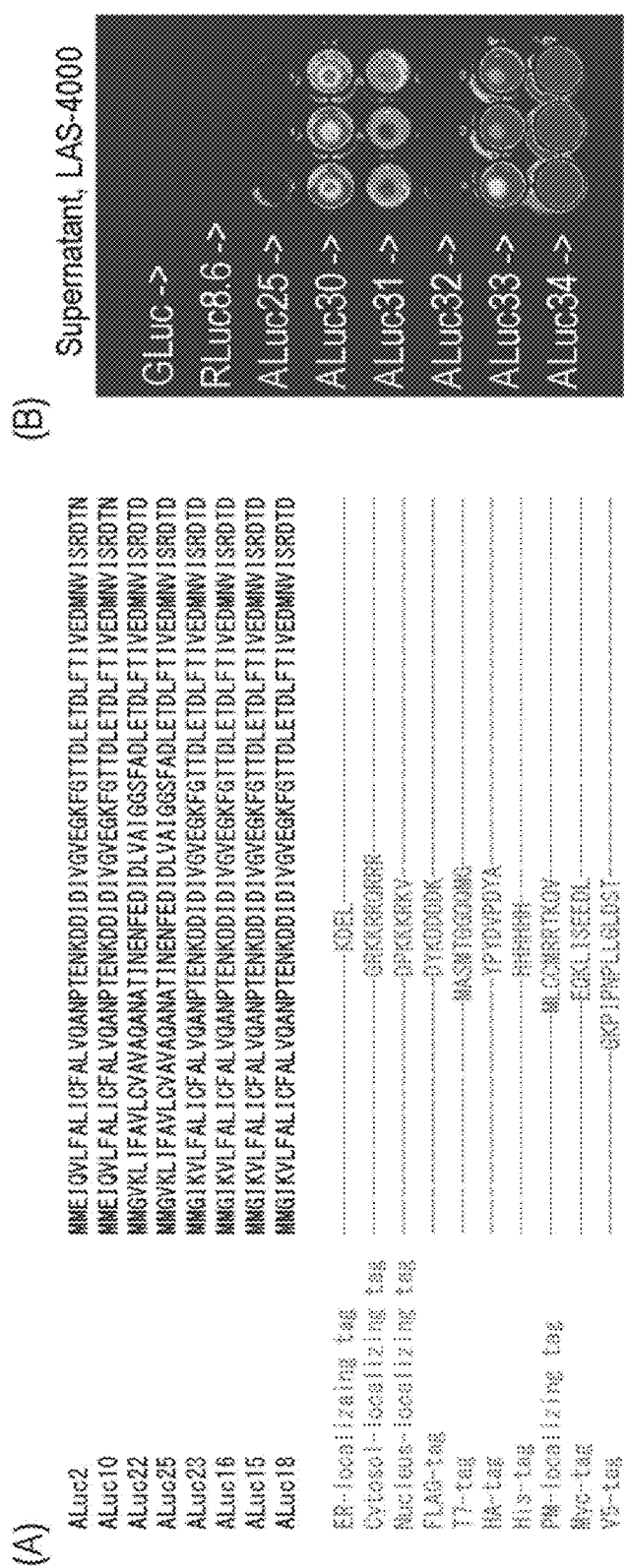
FIG. 21 Establishment of more functional artificial bioluminescent enzymes (ALuc30-34)
Establishment of a series of artificial bioluminescent enzymes containing a functional amino acid sequence (an antigen recognition site (epitope) or an affinity column recognition sequence) and comparison of relative luminescence intensity. (A) Search for an optimal site for fusing each functional amino acid sequence. (B) Relative luminescence intensity of luminescent enzymes established in this research. The luminescence intensity after the secretion was compared using a Promega assay kit.

CLUSTALW (http://www.genome.jp/tools/clustalw/), a known amino acid sequence alignment tool, was used in the example to determine the most suitable position at which to insert a "tag." Specifically, the position of the tag was examined to exhibit 100% expected tag performance without inhibiting the luminescence activity of the enzyme (FIG. 21 (A)). Consequently, it was found that the tag was suitably inserted at a position about 20 amino acids from the beginning of the artificial luciferase. Based on this result, novel artificial luciferases containing an His-tag, c-Myc-tag, HA-tag, or Flag-tag at this position were established, and respectively named ALuc30, ALuc32, ALuc33, and ALuc34. Specifically, artificial luciferases containing a His-tag were named ALuc30 and ALuc 31 (analogs thereof). An artificial luciferase containing a c-Myc-tag was named ALuc32. An artificial luciferase containing an HA-tag was named ALuc33, and an artificial luciferase containing a Flag-tag was named ALuc34.

To compare the luminescence intensity of novel luciferases, a comparison experiment was performed under the same conditions as Example 1-2 (COS-7 cells, culturing for one day, using an assay kit produced by Promega) (FIG. 21 (B)). Finally, the luminescence intensity of each luciferase secreted into the medium was compared using an assay kit (containing native coelenterazine (nCTZ)) produced by Promega. Consequently, ALuc30, ALuc33, and ALuc34 were found to be very useful artificial luciferases, and showed relatively high luminescence intensity. The results indicated that even when the functional amino acid sequence (antigen recognition site, affinity chromatography recognition site, localization signal) was inserted into the artificial luciferase of the present invention, secretion from the cells was possible without significantly inhibiting the properties of the enzyme, and excellent luminescence activity was attained.

(Example 1-22) Stability of Functional Artificial Luciferase Having Antigen Recognition Site (Epitope)

The luminescence characteristics of the novel functional artificial luciferases (containing an antibody recognition site (epitope sequence), etc.) established in Example 1-21 were examined.

To compare the relative luminescence intensity of these luciferases, the following experiment was conducted. First, a gene encoding each luciferase was subcloned into pcDNA3.1 (+), which is a eukaryotic expression vector, and each vector was introduced into COS-7 cells. Two days after gene transfer, the relative luminescence intensity of luciferase secreted into each medium was compared using a luminescence reagent produced by Promega.

Figure 22:
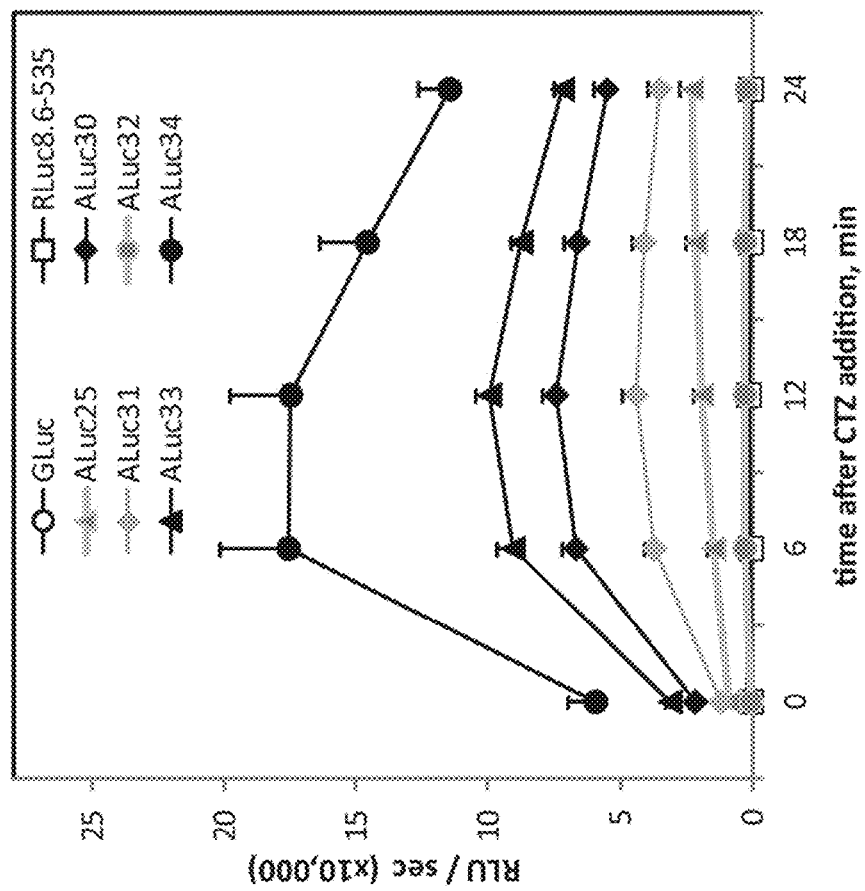
FIG. 22 Luminescence reaction characteristics of novel functional artificial bioluminescent enzymes.

The results surprisingly confirmed a phenomenon in which the luminescence intensity of some luciferases was gradually increased after the substrate injection (FIG. 22). For example, many luciferases showed the maximum luminescence intensity about 6 to 12 minutes after substrate injection. Specifically, ALuc33 and ALuc34 showed the strongest luminescence about 6 to 12 minutes after substrate injection, and then showed a tendency for the luminescence intensity to gradually decrease. In contrast, since ALuc32 (containing c-Myc) showed relatively poor luminescence intensity, it was presumed that part of the c-Myc sequence contained in ALuc32 inhibited its enzymatic activity.

The results of the experiment indicated that the luciferases containing the antibody recognition site obtained herein can, by the antibody recognition site, function as luminescent labels in a living body without losing their enzymatic activity.

(Example 2-1) to (Example 2-10)

The following shows examples of the chemical structures of the components used in (Example 2-1) to (Example 2-10) described below.

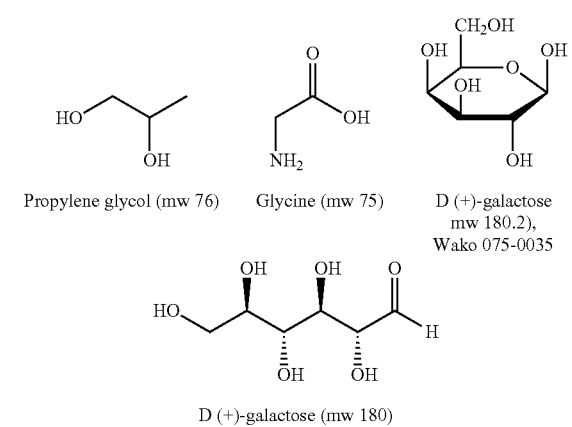

Propylene glycol (mw 76)   Glycine (mw 75)   D (+)-galactose
                                              mw 180.2),
                                              Wako 075-0035

D (+)-galactose (mw 180)

-continued

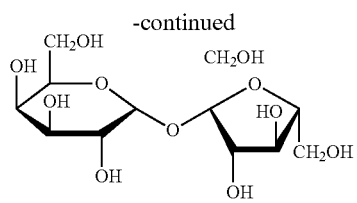

Sucrose, small granules (mw 342.3),
Wako 193.09545

(Example 2-1) Comparative Study on Combination of Lysis Buffer and Assay Buffer

In this example, a comparative study of luminescence intensity was made on different combinations of a lysis buffer and an assay buffer used in conventional bioassays (FIG. 23). COS-7 cells were cultured in a 96-well plate, and a vector for expression of an artificial luciferase (ALuc) was introduced thereto, followed by an additional 8-hour culture. Thereafter, the medium was discarded, and the cells were washed once with a PBS buffer. As shown in FIG. 23, the cells were lysed with 50 μL of each of the lysis buffers (luciferase lysis buffer, cat. E291A, Promega; lysis buffer, cat. B3321, NEB; and C1 to C4) for 20 minutes. Three different substrate-containing assay buffers (C8: an HBSS buffer; C10: a solution prepared by adding EDTA and PEG400 to a Tris buffer (i.e., TE PEG400); and C5: $H_2O$) were individually added dropwise simultaneously to wells of the plate (50 μL each), and the luminescence intensities were measured with an image analyzer (LAS-4000, Fujifilm).

The results revealed that the systems for which the luciferase lysis buffer (cat. E291A) from Promega and a C3 cell lysis solution were used showed outstandingly high luminescence intensities. The results also indicated that HESS and TE PEG buffers are useful as an assay buffer. In particular, when an HESS buffer or a TE PEG buffer was used as an assay buffer with the cell lysis solution of Promega (cat. E291A), high luminescence stability was observed (89 to 92%) (FIG. 23B). The percentage values indicate the ratio of a 5-minute-later luminescence value to the initial luminescence value at which the assay buffer was added. When an HESS buffer was used as an assay buffer in addition to a C3 lysis buffer, high luminance intensity and luminescence stability (71%) were achieved.

(Example 2-2) Search for Optimal Assay Buffer Compatible with C3

On the basis of the results of Example 2-1 indicating C3 as an effectual cell lysis buffer, a search for an optimal assay buffer compatible with C3 was further conducted (FIG. 24). COS-7 cells were cultured in a 96-well plate, and a plasmid for expression of an artificial luciferase (ALuc) was introduced thereto. After 16-hour incubation in a $CO_2$ incubator, 50 μL of a C3 solution was added to each well to allow for cell lysis for 20 minutes. Substrate-containing assay buffers shown in FIG. 24 were individually added simultaneously (50 μL each) to the lysate, and the relative luminescence intensities were immediately measured with an LAS-4000 (Fujifilm). After the substrate-containing assay buffers were further added, the luminescence at the 8- and 16-minute point was measured to examine the luminescence stability.

As seen in FIG. 24A, the results identified PBS, HESS, and Tris-PEG buffers as assay buffers compatible with C3.

As shown in FIG. 24B, the results also revealed that PBS, HESS, Tris-$MgCl_2$, and the like show relatively satisfactory luminescence stability. In contrast, when BSA was added to a PBS buffer, the luminescence intensity and luminescence stability were poor. This indicates that bovine serum albumin (BSA) should not be added to an assay buffer as an additive.

(Example 2-3) Analysis of Effects of Heavy Metal Ions as Additive for Assay Buffer The results of Examples 2-1 and 2-2 revealed that C3 is a useful cell lysis buffer, and that PBS and HBSS are useful assay buffers.

This example examined the effects of a heavy metal ion as an additive for an assay buffer (FIG. 25). First, COS-7 cells were cultured in a 96-well plate, and then a plasmid for expression of an artificial luciferase (ALuc) was introduced thereto. After 16-hour incubation in a $CO_2$ incubator, 50 μL of a C3 solution was added to each well to allow for cell lysis for 20 minutes. 1 ppm of each type of heavy metal ion shown in FIG. 25 and 50 μL of a substrate-containing HBSS buffer were added to the lysate simultaneously, and the relative luminescence intensities were immediately measured with an LAS-4000. After the substrate-containing assay buffer was further added, the luminescence at the 8- and 16-minute point was measured to examine the luminescence stability.

As seen from FIG. 25 (A), the results revealed that the heavy metal additives suitable to be added to C3 and HBSS are Al(III), Ca(II), Cu(II), Fe(III), Mg(II), and the like. The comprehensive evaluation of the luminescence intensity and stability also revealed that Al(III), Cu(II), Fe(III), Mo(VI), Zn(II), and the like are excellent additives. The evaluation further revealed that Cd(II), Co(II), Ni(II), and the like should not be added because these metals significantly decrease the luminescence intensity.

(Example 2-4) Effect of Adding Glycols to Bioassay Reaction Solution

This example examined the effects of adding a glycol to a bioassay reaction solution by actually using a luminescent probe (FIG. 26).

In accordance with a procedure for preparing an integrated-molecule-format bioluminescent probe developed by the present inventors (Non-patent Document 28), a novel integrated-molecule-format bioluminescent probe was developed. An artificial luciferase (ALuc) (for which a patent application was filed on the same date as the application date of the present invention) was newly developed by the present inventors following a technique in which many plankton-derived luciferases were bundled, and from the bundle, thermodynamically highly stable sequences were extracted. The artificial luciferase (ALuc) was bisected, and then an androgen receptor (AR LED) was inserted therebetween (FIG. 26A). The probe was designed such that its molecular structure alters in the presence of an androgen (male hormone, and the enzyme fragments thereby recombine with each other.

For this example, first, COS-7 cells were cultured in a 96-well plate, and a plasmid for encoding the integrated-molecule-format bioluminescent probe was added thereto. After 16-hour incubation in a $CO_2$ incubator, 50 μL of a C3 solution was added to each well to allow for cell lysis for 20 minutes. HESS buffers each containing a substrate and PPG or PEG in the amounts shown in FIG. 26B were prepared. 50 μL of each of the buffers was individually added to the lysate simultaneously with a multichannel pipette. The luminescence was immediately measured using a conventional luminometer (GloMax 20/20n; Promega).

The results revealed that the addition of PPG or PEG is expected to produce effective results. It was also found that the suitable amount of such additives is about 1% based on the amount of the assay buffer.

(Example 2-5) Effect of Adding Halogen Ions to Bioassay Reaction Solution

This example examined the effects of adding a halogen ion to a bioassay reaction solution (FIG. 27). Using the integrated-molecule-format bioluminescent probe prepared in Example 2-4, a study was conducted to evaluate the effects of adding a halogen ion ($Br^-$ or $I^-$) to a reaction solution used in the recognition of an androgen by the luminescent probe.

A plasmid for encoding the integrated-molecule-format bioluminescent probe was introduced into COS-7 cells cultured in a 96-well plate using TranslT-LT1. After 16-hour incubation in a $CO_2$ incubator, 50 µL of a C3 solution was added to each well to allow for cell lysis for 20 minutes. HESS buffers containing a substrate and KBr or KI in the amounts shown in FIG. 27B were prepared. 50 µL of each of the buffers was individually added to the lysate simultaneously with a multichannel pipette. The luminescence was immediately measured using a conventional luminometer (GloMax 20/20n; Promega).

The results revealed that the addition of a halogen ion is effective. Specifically, KI in any amount achieved excellent results, and the addition of KI in an amount of 50 mM achieved particularly excellent results. KBr, when added in an amount of about 100 mM, achieved excellent results.

(Example 2-6) Effect of Adding Polysaccharides to Bioassay Reaction Solution

This example examined the effects of adding a polysaccharide to a bioassay reaction solution (FIG. 28). Using the integrated-molecule-format bioluminescent probe prepared in Example 2-4, a study was conducted to evaluate the effects of adding a polysaccharide to a reaction solution used in the recognition of an androgen by the luminescent probe.

A plasmid for encoding the integrated-molecule-format bioluminescent probe was introduced into COS-7 cells cultured in a 96-well plate using TranslT-LT1. After 16-hour incubation in a $CO_2$ incubator, 50 µL of a C3 solution was added to each well to allow for cell lysis for 20 minutes. HESS buffers containing a substrate and polysaccharides in the amounts shown in the figure were prepared, and 50 µL of each of the buffers was added to the lysate simultaneously with a multichannel pipette. The luminescence was immediately measured using a conventional luminometer (GloMax 20/20n; Promega).

The results revealed that the addition of sucrose and glucose is particularly effective. The addition of not only a polysaccharide, but also glycine was found to be effective. The suitable amount was 2 mg/mL.

(Example 2-7) Stress Hormone Assay Test 1 Using Integrated-Molecule-Format Bioluminescent Probe (cSimgr8)

To demonstrate the excellent performance of the one-shot buffer according to the present invention, bioassays were conducted by using C14 to C22 reaction buffers of the present invention with an integrated-molecule-format bioluminescent probe (cSimgr8) having a stress hormone receptor (the ligand-binding domain of glucocorticoid receptor; GR LBD) as a frame structure (FIG. 29). cSimgr8 is a novel integrated-molecule-format bioluminescent probe prepared by dissecting the artificial luciferase (ALuc), which was independently developed as shown in Example 2-4, into two fragments, circularly permuting the fragments in a desired manner, and binding a stress hormone receptor (the ligand-binding domain of glucocorticoid receptor; GR LBD) and its specific binding sequence to the outer ends of the fragments.

First, COS-7 cells were cultured in a 96-well plate, and cSimgr8 was introduced thereto. After an additional 16-hour culture, the COS-7 cells in the plate were divided into two groups. One group of the cells was stimulated with $10^{-5}$ M of a stress hormone (cortisol) for 20 minutes, and the other group of the cells was simulated with a control (0.1% DMSO) for 20 minutes. Thereafter, the medium in the plate was discarded to leave only the cells in the plate. Buffers of the formulations of C14 to C22 were prepared as one-shot buffers. A high-sensitivity Promega luminometer (GloMax 20/20n; Promega) was used for luminescence measurement.

The assay was conducted as follows. C14 to C22 solutions (50 µL each) were individually added to the wells of the plate from which the medium was already removed, and the samples were pipetted a few times. Thereafter, the whole volume of the samples was individually placed into respective 1.6 mL Eppendorf tubes, and the amount of light was measured for 3 seconds with the luminometer. FIG. 29 shows the results for each buffer.

(Example 2-8) Stress Hormone Assay Test 2 Using Integrated-Molecule-Format Bioluminescent Probe (cSimgr8)

A stress hormone assay using an integrated-molecule-format bioluminescent probe (cSimgr8) was conducted in the same manner as in Example 2-7 using C23 to C26 reaction buffers of the present invention (FIG. 30).

As in Example 2-7, COS-7 cells were cultured in a 96-well plate, and cSimgr8 was introduced thereto. After an additional 16 hour-culture, the COS-7 cells in the plate were divided into two groups. One group of the cells was stimulated with $10^{-5}$ M of a stress hormone (cortisol) for 20 minutes, and the other group of the cells was simulated with a control (0.1% DMSO) for 20 minutes. Thereafter, the medium in the plate was discarded to leave only the cells in the plate. Buffers of the formulations of C14 to C22 were prepared as one-shot buffers. A high-sensitivity Promega luminometer (GloMax 20/20n; Promega) was used for luminescence measurement.

The assay was conducted as follows. C23 to C26 solutions (50 µL each) were individually added to the wells of the plate from which the medium was already removed, and the samples were pipetted a few times. Thereafter, the whole volume of the samples was individually placed into respective 1.6 mL Eppendorf tubes, and the amount of light was measured for 3 seconds with the luminometer. FIG. 30 shows the results for each buffer.

(Example 2-9) Androgen Assay Test Using Integrated-Molecule-Format Bioluminescent Probe (pLeu-rich)

To demonstrate the excellent performance of the one-shot buffer according to the present invention, the buffer was used for an integrated-molecule-format bioluminescent probe (pLeu-rich) having an androgen (male hormone) receptor (the ligand-binding domain of androgen receptor; AR LBD) as a frame structure. pLeu-rich is an integrated-molecule-format bioluminescent probe that was previously developed by the present inventors using a firefly-derived luciferase (Non-patent Document 29).

COS-7 cells were cultured in a 96-well plate, and pLeu-rich was introduced thereto. After an additional 16-hour culture, the COS-7 cells in the plate were divided into two groups. Some portions of the cells were individually stimulated with $10^{-5}$ M of 5α-dihydrotestosterone (DHT), 4-hydroxytamoxifen (OHT), 17β-estradiol ($E_2$), dichlorodiphenyltrichloroethane (DDT), or polychlorinated biphenyls (PCB) for 20 minutes. Thereafter, the medium was discarded, and the assay preparation for the cells was completed. A reaction buffer prepared by mixing a C29 solution with D-luciferin was used. A high-sensitivity Promega luminometer (GloMax 20/20n; Promega) was used for luminescence measurement.

The assay was conducted as follows. 50 μL of a C16 solution was added to the plate from which the medium was already removed, and the samples were pipetted a few times. Thereafter, the whole volume of the samples were individually placed into respective 1.6 mL Eppendorf tubes, and the amount of light was measured for 3 seconds with the luminometer.

FIG. 31 shows the results. The results indicate a certain level of detection capability for DHT and $E_2$ (about 3 to 5 folds higher than the background). The results also reveled that the procedure from cell lysis to measurement can be conducted instantly (within a few seconds). This indicates that the conventional, complicated procedure that typically takes 30 minutes or more has been significantly simplified, showing the superiority of the reaction buffer in these respects.

(Example 2-10) Estrogen Assay Test Using Integrated-Molecule-Format Bioluminescent Probe (pSimer-r2)

To demonstrate the excellent performance of the reaction buffer (one-shot buffer), the buffer was used for an integrated-molecule-format bioluminescent probe (pSimer-r2) having an estrogen (female hormone) receptor (the ligand-binding domain of estrogen receptor; ER LBD) as a frame structure. pSimer-r2 is an integrated-molecule-format bioluminescent probe that was previously developed by the present inventors using a luciferase originating from click beetle (click beetle luciferase; CBLuc) (Non-patent Document 12).

COS-7 cells were cultured in a 96-well plate, and pSimer-r2 was introduced thereto. After an additional 16-hour culture, the COS-7 cells in the plate were divided into two groups. Some portions of the cells were individually stimulated with $10^{-5}$ M of 5α-dihydrotestosterone (DHT), 4-hydroxytamoxifen (OHT), 17β-estradiol ($E_2$), dichlorodiphenyltrichloroethane (DDT), or polychlorinated biphenyls (PCB) for 20 minutes. The remaining cells were used as a control group (control). Thereafter, the medium was discarded, and the assay preparation for the cells was completed. C16 was used as a one-shot reaction buffer. A high-sensitivity Promega luminometer (GloMax 20/20n; Promega) was used for luminescence measurement.

The assay was conducted as follows. 50 μL of a C16 solution was added to the plate from which the medium was already removed, and the samples were pipetted a few times. Thereafter, the whole volume of the samples were individually placed into respective 1.6 mL Eppendorf tubes, and the amount of light was measured with the luminometer.

FIG. 32 shows the results. The results indicate a certain level of detection capability for 4-hydroxytamoxifen (OHT) (about 5 folds higher than the background). The results also revealed that the procedure from cell lysis to measurement can be conducted instantly (within a few seconds). This indicates that the conventional, complicated procedure that typically takes 30 minutes or more has been significantly simplified, showing the superiority of the reaction buffer in these respects.

INDUSTRIAL APPLICABILITY

By using the present invention for ligand measurement based on a reporter-gene assay method, which has hitherto been widely used, or as a replacement for a luciferase used in a known bioluminescent probe, it becomes possible to exponentially improve measurement performance during assay. Therefore, the present invention can be used for various applications, including the development of a diagnosis reagent for basic biology research, medical and pharmaceutical purposes, or analytical chemistry.

Sequence Listing

The invention claimed is:

1. A nucleic acid encoding a polypeptide having:
   (a) the amino acid sequence represented by SEQ ID NO: 38,
   wherein the polypeptide has copepod luciferase activity, and
   wherein the polypeptide has
   (i) the amino acid sequence represented by any of SEQ ID NOs: 11 to 17 and 24 to 36,
   (ii) the amino acid sequence represented by any of SEQ ID NOs: 11 to 17 and 24 to 36, wherein 1-20 amino acids are deleted, substituted, inserted, or added, or
   (iii) the amino acid sequence having an identity of not less than 90/o with any of amino acid sequences represented by SEQ ID NOs: 11 to 17 and 24 to 36.

2. An expression vector in which the nucleic acid according to claim 1 is inserted in a manner such that the nucleic acid can be expressed.

3. A transformed cell in which the nucleic acid according to claim 1 is introduced in a manner such that the nucleic acid can be expressed.

4. The nucleic acid according to claim 1, wherein the region corresponding to positions 1-71 in the amino acid sequence represented by SEQ ID NO: 38 is represented by SEQ ID NO: 39.

5. The nucleic acid according to claim 1, wherein the region corresponding to positions 1-157 in the amino acid sequence represented by SEQ ID NO: 38 is represented by SEQ ID NO: 40.

6. The nucleic acid according to claim 1, wherein the region corresponding to positions 20-31 in the amino acid sequence represented by SEQ ID NO: 38 includes an antibody recognition site selected from the group consisting of His-tag (HHHHHH) (SEQ ID NO: 5), FLAG-tag (DYKDDDDK) (SEQ ID NO: 6), Myc-tag (EQKLISEEDL) (SEQ ID NO: 7), and HA-tag (YPYDVPDYA) (SEQ ID NO: 8).

* * * * *

```
SEQUENCE LISTING

<160> NUMBER OF SEQ ID NOS: 62

<210> SEQ ID NO 1
<211> LENGTH: 11
<212> TYPE: PRT
<213> ORGANISM: Artificial Sequence
<220> FEATURE:
<223> OTHER INFORMATION: Synthetic Membrane localization signal

<400> SEQUENCE: 1

Met Leu Cys Cys Met Arg Arg Thr Lys Gln Val
1               5                   10

<210> SEQ ID NO 2
<211> LENGTH: 10
<212> TYPE: PRT
<213> ORGANISM: Artificial Sequence
<220> FEATURE:
```

```
<223> OTHER INFORMATION: Synthetic Cytoplasmic localization signal

<400> SEQUENCE: 2

Gly Arg Lys Lys Arg Arg Gln Arg Arg Arg
1               5                   10

<210> SEQ ID NO 3
<211> LENGTH: 4
<212> TYPE: PRT
<213> ORGANISM: Artificial Sequence
<220> FEATURE:
<223> OTHER INFORMATION: Synthetic Endoplasmic reticulum (ER)
      localization signal

<400> SEQUENCE: 3

Lys Asp Glu Leu
1

<210> SEQ ID NO 4
<211> LENGTH: 8
<212> TYPE: PRT
<213> ORGANISM: Artificial Sequence
<220> FEATURE:
<223> OTHER INFORMATION: Synthetic Nuclear localization signal (NLS)

<400> SEQUENCE: 4

Asp Pro Lys Lys Lys Arg Lys Val
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic His-Tag

<400> SEQUENCE: 5

His His His His His His
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic FLAG-tag

<400> SEQUENCE: 6

Asp Tyr Lys Asp Asp Asp Asp Lys
1               5

<210> SEQ ID NO 7
<211> LENGTH: 10
<212> TYPE: PRT
<213> ORGANISM: Artificial Sequence
<220> FEATURE:
<223> OTHER INFORMATION: Synthetic Myc-tag

<400> SEQUENCE: 7

Glu Gln Lys Leu Ile Ser Glu Glu Asp Leu
1               5                   10

<210> SEQ ID NO 8
<211> LENGTH: 9
<212> TYPE: PRT
<213> ORGANISM: Artificial Sequence
<220> FEATURE:
```

<223> OTHER INFORMATION: Synthetic HA-tag

<400> SEQUENCE: 8

Tyr Pro Tyr Asp Val Pro Asp Tyr Ala
1               5

<210> SEQ ID NO 9
<211> LENGTH: 14
<212> TYPE: PRT
<213> ORGANISM: Artificial Sequence
<220> FEATURE:
<223> OTHER INFORMATION: Synthetic V5-tag

<400> SEQUENCE: 9

Gly Lys Pro Ile Pro Asn Pro Leu Leu Gly Leu Asp Ser Thr
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic T7-tag

<400> SEQUENCE: 10

Met Ala Ser Met Thr Gly Gly Gln Gln Met Gly
1               5                   10

<210> SEQ ID NO 11
<211> LENGTH: 209
<212> TYPE: PRT
<213> ORGANISM: Artificial Sequence
<220> FEATURE:
<223> OTHER INFORMATION: Synthetic ALuc10

<400> SEQUENCE: 11

Met Met Glu Ile Gln Val Leu Phe Ala Leu Ile Cys Phe Ala Leu Val
1               5                   10                  15

Gln Ala Asn Pro Thr Glu Asn Lys Asp Asp Ile Asp Ile Val Gly Val
                20                  25                  30

Glu Gly Lys Phe Gly Thr Thr Asp Leu Glu Thr Asp Leu Phe Thr Ile
            35                  40                  45

Val Glu Asp Met Asn Val Ile Ser Arg Asp Thr Asn Leu Ala Asn Ser
    50                  55                  60

Asp Ala Asp Arg Gly Lys Leu Pro Gly Lys Lys Leu Pro Leu Glu Val
65                  70                  75                  80

Leu Lys Glu Leu Glu Ala Asn Ala Gln Lys Ala Gly Cys Thr Arg Gly
                85                  90                  95

Cys Leu Ile Cys Leu Ser His Ile Lys Cys Thr Ala Lys Met Lys Lys
            100                 105                 110

Trp Leu Pro Gly Arg Cys Glu Ser Trp Glu Gly Asp Lys Glu Thr Gly
        115                 120                 125

Gln Gly Gly Ile Gly Glu Ala Ile Val Asp Ile Pro Glu Ile Pro Gly
    130                 135                 140

Phe Lys Asp Leu Glu Pro Met Glu Gln Phe Ile Ala Gln Val Asp Leu
145                 150                 155                 160

Cys Val Asp Cys Thr Thr Gly Cys Leu Lys Gly Leu Ala Asn Val Lys
                165                 170                 175

Cys Ser Asp Leu Leu Lys Lys Trp Leu Pro Ser Arg Cys Ala Thr Phe
            180                 185                 190

Ala Ser Lys Ile Gln Ala Gln Val Asp Lys Ile Lys Gly Ala Gly Gly
            195                 200                 205
Ser

<210> SEQ ID NO 12
<211> LENGTH: 209
<212> TYPE: PRT
<213> ORGANISM: Artificial Sequence
<220> FEATURE:
<223> OTHER INFORMATION: Synthetic ALuc15

<400> SEQUENCE: 12

Met Met Gly Ile Lys Val Leu Phe Ala Leu Ile Cys Phe Ala Leu Val
1               5                   10                  15

Gln Ala Asn Pro Thr Glu Asn Lys Asp Asp Ile Asp Ile Val Gly Val
            20                  25                  30

Glu Gly Lys Phe Gly Thr Thr Asp Leu Glu Thr Asp Leu Phe Thr Ile
        35                  40                  45

Val Glu Asp Met Asn Val Ile Ser Arg Asp Thr Asp Val Asp Ala Asn
    50                  55                  60

Arg Ala Asp Arg Gly Lys Leu Pro Gly Lys Lys Leu Pro Leu Glu Val
65                  70                  75                  80

Leu Lys Glu Leu Glu Ala Asn Ala Gln Lys Ala Gly Cys Thr Arg Gly
                85                  90                  95

Cys Leu Ile Cys Leu Ser His Ile Lys Cys Thr Ala Lys Met Lys Lys
            100                 105                 110

Trp Leu Pro Gly Arg Cys Glu Ser Trp Glu Gly Asp Lys Glu Thr Gly
        115                 120                 125

Gln Gly Gly Ile Gly Glu Ala Ile Val Asp Ile Pro Glu Ile Pro Gly
    130                 135                 140

Phe Lys Asp Leu Glu Pro Met Glu Gln Phe Ile Ala Gln Val Asp Leu
145                 150                 155                 160

Cys Val Asp Cys Thr Thr Gly Cys Leu Lys Gly Leu Ala Asn Val Lys
                165                 170                 175

Cys Ser Asp Leu Leu Lys Lys Trp Leu Pro Ser Arg Cys Ala Thr Phe
            180                 185                 190

Ala Ser Lys Ile Gln Ala Gln Val Asp Lys Ile Lys Gly Ala Gly Gly
        195                 200                 205
Ser

<210> SEQ ID NO 13
<211> LENGTH: 212
<212> TYPE: PRT
<213> ORGANISM: Artificial Sequence
<220> FEATURE:
<223> OTHER INFORMATION: Synthetic ALuc16

<400> SEQUENCE: 13

Met Met Gly Ile Lys Val Leu Phe Ala Leu Ile Cys Phe Ala Leu Val
1               5                   10                  15

Gln Ala Asn Pro Thr Glu Asn Lys Asp Asp Ile Asp Ile Val Gly Val
            20                  25                  30

Glu Gly Lys Phe Gly Thr Thr Asp Leu Glu Thr Asp Leu Phe Thr Ile
        35                  40                  45

Val Glu Asp Met Asn Val Ile Ser Arg Asp Thr Asp Val Asp Ala Asn
    50                  55                  60

Arg Ala Asp Arg Gly Arg Arg Gly Lys Leu Pro Gly Lys Lys Leu Pro

```
            65                  70                  75                  80
Leu Glu Val Leu Lys Glu Leu Ala Asn Ala Gln Lys Ala Gly Cys
                85                  90                  95

Thr Arg Gly Cys Leu Ile Cys Leu Ser His Ile Lys Cys Thr Ala Lys
                100                 105                 110

Met Lys Lys Trp Leu Pro Gly Arg Cys Glu Ser Trp Glu Gly Asp Lys
                115                 120                 125

Glu Thr Gly Gln Gly Gly Ile Gly Glu Ala Ile Val Asp Ile Pro Glu
            130                 135                 140

Ile Pro Gly Phe Lys Asp Leu Glu Pro Met Glu Gln Phe Ile Ala Gln
145                 150                 155                 160

Val Asp Leu Cys Val Asp Cys Thr Thr Gly Cys Leu Lys Gly Leu Ala
                165                 170                 175

Asn Val Lys Cys Ser Asp Leu Leu Lys Lys Trp Leu Pro Ser Arg Cys
                180                 185                 190

Ala Thr Phe Ala Ser Lys Ile Gln Ala Gln Val Asp Lys Ile Lys Gly
                195                 200                 205

Ala Gly Gly Ser
210

<210> SEQ ID NO 14
<211> LENGTH: 215
<212> TYPE: PRT
<213> ORGANISM: Artificial Sequence
<220> FEATURE:
<223> OTHER INFORMATION: Synthetic ALuc18

<400> SEQUENCE: 14

Met Met Gly Ile Lys Val Leu Phe Ala Leu Ile Cys Phe Ala Leu Val
1               5                   10                  15

Gln Ala Asn Pro Thr Glu Asn Lys Asp Asp Ile Asp Ile Val Gly Val
                20                  25                  30

Glu Gly Lys Phe Gly Thr Thr Asp Leu Glu Thr Asp Leu Phe Thr Ile
                35                  40                  45

Val Glu Asp Met Asn Val Ile Ser Arg Asp Thr Asp Val Asp Ala Asn
50                  55                  60

Arg Ala Asp Arg Gly Arg Gly His Gly Gly Leu Pro Gly Lys Lys
65                  70                  75                  80

Met Pro Leu Glu Val Leu Leu Glu Leu Glu Ala Asn Ala Gln Arg Ala
                85                  90                  95

Gly Cys Thr Arg Gly Cys Leu Ile Cys Leu Ser Lys Ile Lys Cys Thr
                100                 105                 110

Ala Lys Met Lys Lys Trp Leu Pro Gly Arg Cys Glu Ser Trp Ala Gly
                115                 120                 125

Asp Lys Glu Thr Gly Gln Gly Gly Ile Thr Glu Glu Thr Val Asp
            130                 135                 140

Ile Pro Glu Ile Pro Gly Phe Lys Asp Leu Glu Pro Met Glu Gln Phe
145                 150                 155                 160

Ile Ala Gln Val Asp Leu Cys Val Asp Cys Thr Thr Gly Cys Leu Lys
                165                 170                 175

Gly Leu Ala Asn Val Lys Cys Ser Asp Leu Leu Lys Lys Trp Leu Pro
                180                 185                 190

Ser Arg Cys Ala Thr Phe Ala Ser Lys Ile Gln Ala Gln Val Asp Lys
                195                 200                 205

Ile Lys Gly Ala Gly Gly Ser
```

<210> SEQ ID NO 15
<211> LENGTH: 212
<212> TYPE: PRT
<213> ORGANISM: Artificial Sequence
<220> FEATURE:
<223> OTHER INFORMATION: Synthetic ALuc22

<400> SEQUENCE: 15

```
Met Met Gly Val Lys Leu Ile Phe Ala Val Leu Cys Val Ala Val Ala
1               5                   10                  15

Gln Ala Asn Ala Thr Ile Asn Glu Asn Phe Glu Asp Ile Asp Leu Val
            20                  25                  30

Ala Ile Gly Gly Ser Phe Ala Asp Leu Glu Thr Asp Leu Phe Thr Ile
        35                  40                  45

Val Glu Asp Met Asn Val Ile Ser Arg Asp Thr Val Asp Ala Asn
    50                  55                  60

Arg Gly Gly Arg Gly Arg Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
        115                 120                 125

Glu Thr Gly Gln Gly Gly Ile Gly Glu Ala Ile Val Asp Ile Pro Glu
    130                 135                 140

Ile Pro Gly Phe Lys Asp Leu Glu Pro Met Glu Gln Phe Ile Ala Gln
145                 150                 155                 160

Val Asp Leu Cys Val Asp Cys Thr Thr Gly Cys Leu Lys Gly Leu Ala
                165                 170                 175

Asn Val Lys Cys Ser Asp Leu Leu Lys Lys Trp Leu Pro Ser Arg Cys
            180                 185                 190

Ala Thr Phe Ala Ser Lys Ile Gln Ala Gln Val Asp Lys Ile Lys Gly
        195                 200                 205

Ala Gly Gly Ser
    210
```

<210> SEQ ID NO 16
<211> LENGTH: 212
<212> TYPE: PRT
<213> ORGANISM: Artificial Sequence
<220> FEATURE:
<223> OTHER INFORMATION: Synthetic ALuc23

<400> SEQUENCE: 16

```
Met Met Gly Ile Lys Val Leu Phe Ala Leu Ile Cys Phe Ala Leu Val
1               5                   10                  15

Gln Ala Asn Pro Thr Glu Asn Lys Asp Asp Ile Asp Ile Val Gly Val
            20                  25                  30

Glu Gly Lys Phe Gly Thr Thr Asp Leu Glu Thr Asp Leu Phe Thr Ile
        35                  40                  45

Val Glu Asp Met Asn Val Ile Ser Arg Asp Thr Val Asp Ala Asn
    50                  55                  60

Arg Ala Asp Arg Gly Arg Arg Gly Lys Leu Pro Gly Lys Lys Leu Pro
65                  70                  75                  80
```

```
Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
            115                 120                 125

Glu Thr Gly Gln Gly Gly Ile Gly Glu Ala Ile Val Asp Ile Pro Glu
            130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Lys Cys Ser Ala Leu Leu Lys Lys Trp Leu Pro Ser Arg Cys
                180                 185                 190

Ala Gly Phe Ala Asp Lys Ile Gln Ala Gln Val Asp Thr Ile Lys Gly
            195                 200                 205

Ala Gly Gly Ser
            210

<210> SEQ ID NO 17
<211> LENGTH: 212
<212> TYPE: PRT
<213> ORGANISM: Artificial Sequence
<220> FEATURE:
<223> OTHER INFORMATION: Synthetic ALuc25

<400> SEQUENCE: 17

Met Met Gly Val Lys Leu Ile Phe Ala Val Leu Cys Val Ala Val Ala
1               5                   10                  15

Gln Ala Asn Ala Thr Ile Asn Glu Asn Phe Glu Asp Ile Asp Leu Val
            20                  25                  30

Ala Ile Gly Gly Ser Phe Ala Asp Leu Glu Thr Asp Leu Phe Thr Ile
            35                  40                  45

Val Glu Asp Met Asn Val Ile Ser Arg Asp Thr Val Asp Ala Asn
50                  55                  60

Arg Gly Gly Arg Gly Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
            115                 120                 125

Glu Thr Gly Gln Gly Gly Ile Gly Glu Ala Ile Val Asp Ile Pro Glu
            130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Lys Cys Ser Ala Leu Leu Lys Lys Trp Leu Pro Ser Arg Cys
                180                 185                 190

Ala Gly Phe Ala Asp Lys Ile Gln Ala Gln Val Asp Thr Ile Lys Gly
            195                 200                 205

Ala Gly Gly Ser
            210
```

<210> SEQ ID NO 18
<211> LENGTH: 216
<212> TYPE: PRT
<213> ORGANISM: Artificial Sequence
<220> FEATURE:
<223> OTHER INFORMATION: Synthetic KDEL-linked ALuc16

<400> SEQUENCE: 18

```
Met Met Gly Ile Lys Val Leu Phe Ala Leu Ile Cys Phe Ala Leu Val
1               5                   10                  15

Gln Ala Asn Pro Thr Glu Asn Lys Asp Asp Ile Asp Ile Val Gly Val
            20                  25                  30

Glu Gly Lys Phe Gly Thr Thr Asp Leu Glu Thr Asp Leu Phe Thr Ile
        35                  40                  45

Val Glu Asp Met Asn Val Ile Ser Arg Asp Thr Asp Val Asp Ala Asn
    50                  55                  60

Arg Ala Asp Arg Gly Arg Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
        115                 120                 125

Glu Thr Gly Gln Gly Gly Ile Gly Glu Ala Ile Val Asp Ile Pro Glu
130                 135                 140

Ile Pro Gly Phe Lys Asp Leu Glu Pro Met Glu Gln Phe Ile Ala Gln
145                 150                 155                 160

Val Asp Leu Cys Val Asp Cys Thr Thr Gly Cys Leu Lys Gly Leu Ala
                165                 170                 175

Asn Val Lys Cys Ser Asp Leu Leu Lys Lys Trp Leu Pro Ser Arg Cys
            180                 185                 190

Ala Thr Phe Ala Ser Lys Ile Gln Ala Gln Val Asp Lys Ile Lys Gly
        195                 200                 205

Ala Gly Gly Ser Lys Asp Glu Leu
    210                 215
```

<210> SEQ ID NO 19
<211> LENGTH: 229
<212> TYPE: PRT
<213> ORGANISM: Artificial Sequence
<220> FEATURE:
<223> OTHER INFORMATION: Synthetic MLS&DEVD-linked ALuc16 (a
      bioluminescent capsule)

<400> SEQUENCE: 19

```
Met Met Gly Ile Lys Val Leu Phe Ala Leu Ile Cys Phe Ala Leu Val
1               5                   10                  15

Gln Ala Asn Pro Thr Glu Asn Lys Asp Asp Ile Asp Ile Val Gly Val
            20                  25                  30

Glu Gly Lys Phe Gly Thr Thr Asp Leu Glu Thr Asp Leu Phe Thr Ile
        35                  40                  45

Val Glu Asp Met Asn Val Ile Ser Arg Asp Thr Asp Val Asp Ala Asn
    50                  55                  60

Arg Ala Asp Arg Gly Arg Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
```

```
            85                  90                  95
Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
            115                 120                 125

Glu Thr Gly Gln Gly Gly Ile Gly Glu Ala Ile Val Asp Ile Pro Glu
            130                 135                 140

Ile Pro Gly Phe Lys Asp Leu Glu Pro Met Glu Gln Phe Ile Ala Gln
145                 150                 155                 160

Val Asp Leu Cys Val Asp Cys Thr Thr Gly Cys Leu Lys Gly Leu Ala
                165                 170                 175

Asn Val Lys Cys Ser Asp Leu Leu Lys Lys Trp Leu Pro Ser Arg Cys
                180                 185                 190

Ala Thr Phe Ala Ser Lys Ile Gln Ala Gln Val Asp Lys Ile Lys Gly
                195                 200                 205

Ala Gly Gly Ser Asp Glu Val Asp Leu Glu Gln Gly Cys Met Gly Leu
                210                 215                 220

Pro Cys Val Val Met
225

<210> SEQ ID NO 20
<211> LENGTH: 459
<212> TYPE: PRT
<213> ORGANISM: Artificial Sequence
<220> FEATURE:
<223> OTHER INFORMATION: Synthetic ALuc16-mPlum-MLS (a bioluminescent
      capsule)

<400> SEQUENCE: 20

Met Met Gly Ile Lys Val Leu Phe Ala Leu Ile Cys Phe Ala Leu Val
1               5                   10                  15

Gln Ala Asn Pro Thr Glu Asn Lys Asp Asp Ile Asp Ile Val Gly Val
                20                  25                  30

Glu Gly Lys Phe Gly Thr Thr Asp Leu Glu Thr Asp Leu Phe Thr Ile
            35                  40                  45

Val Glu Asp Met Asn Val Ile Ser Arg Asp Thr Asp Val Asp Ala Asn
    50                  55                  60

Arg Ala Asp Arg Gly Arg Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
            115                 120                 125

Glu Thr Gly Gln Gly Gly Ile Gly Glu Ala Ile Val Asp Ile Pro Glu
            130                 135                 140

Ile Pro Gly Phe Lys Asp Leu Glu Pro Met Glu Gln Phe Ile Ala Gln
145                 150                 155                 160

Val Asp Leu Cys Val Asp Cys Thr Thr Gly Cys Leu Lys Gly Leu Ala
                165                 170                 175

Asn Val Lys Cys Ser Asp Leu Leu Lys Lys Trp Leu Pro Ser Arg Cys
                180                 185                 190

Ala Thr Phe Ala Ser Lys Ile Gln Ala Gln Val Asp Lys Ile Lys Gly
                195                 200                 205
```

Ala Gly Gly Ser Ile Glu Thr Asp Met Val Ser Lys Gly Glu Val
    210             215                 220

Ile Lys Glu Phe Met Arg Phe Lys Glu His Met Glu Gly Ser Val Asn
225             230                 235                 240

Gly His Glu Phe Glu Ile Glu Gly Gly Glu Gly Arg Pro Tyr Glu
                245                 250                 255

Gly Thr Gln Thr Ala Arg Leu Lys Val Thr Lys Gly Gly Pro Leu Pro
                260                 265                 270

Phe Ala Trp Asp Ile Leu Ser Pro Gln Ile Met Tyr Gly Ser Lys Ala
                275                 280                 285

Tyr Val Lys His Pro Ala Asp Ile Pro Asp Tyr Leu Lys Leu Ser Phe
    290                 295                 300

Pro Glu Gly Phe Lys Trp Glu Arg Val Met Asn Phe Glu Asp Gly Gly
305             310                 315                 320

Val Val Thr Val Thr Gln Asp Ser Ser Leu Gln Asp Gly Glu Phe Ile
                325                 330                 335

Tyr Lys Val Lys Val Arg Gly Thr Asn Phe Pro Ser Asp Gly Pro Val
                340                 345                 350

Met Gln Lys Lys Thr Met Gly Trp Glu Ala Ser Ser Glu Arg Met Tyr
                355                 360                 365

Pro Glu Asp Gly Ala Leu Lys Gly Glu Met Lys Met Arg Leu Arg Leu
370                 375                 380

Lys Asp Gly Gly His Tyr Asp Ala Glu Val Lys Thr Thr Tyr Met Ala
385                 390                 395                 400

Lys Lys Pro Val Gln Leu Pro Gly Ala Tyr Lys Thr Asp Ile Lys Leu
                405                 410                 415

Asp Ile Thr Ser His Asn Glu Asp Tyr Thr Ile Val Glu Gln Tyr Glu
                420                 425                 430

Arg Ala Glu Gly Arg His Ser Thr Gly Ala Asp Glu Val Asp Leu Glu
                435                 440                 445

Gln Gly Cys Met Gly Leu Pro Cys Val Val Met
    450                 455

<210> SEQ ID NO 21
<211> LENGTH: 510
<212> TYPE: PRT
<213> ORGANISM: Artificial Sequence
<220> FEATURE:
<223> OTHER INFORMATION: Synthetic cSimgr8 (single-chain probe)

<400> SEQUENCE: 21

Met Asn Ala Leu Leu Arg Tyr Leu Leu Asp Lys Asp Gly Ser Gly Ile
1               5                   10                  15

Gly Glu Ala Ile Val Asp Ile Pro Glu Ile Pro Gly Phe Lys Asp Leu
                20                  25                  30

Glu Pro Met Glu Gln Phe Ile Ala Gln Val Asp Leu Cys Val Asp Cys
                35                  40                  45

Thr Thr Gly Cys Leu Lys Gly Leu Ala Asn Val Lys Cys Ser Asp Leu
                50                  55                  60

Leu Lys Lys Trp Leu Pro Ser Arg Cys Ala Thr Phe Ala Ser Lys Ile
65              70                  75                  80

Gln Ala Gln Val Asp Lys Ile Lys Gly Ala Gly Leu Ser Gly Ser
                85                  90                  95

Gly Gly Asn Pro Thr Glu Asn Lys Asp Asp Ile Asp Ile Val Gly Val
                100                 105                 110

```
Glu Gly Lys Phe Gly Thr Thr Asp Leu Glu Thr Asp Leu Phe Thr Ile
            115                 120                 125
Val Glu Asp Met Asn Val Ile Ser Arg Asp Thr Asp Val Asp Ala Asn
130                 135                 140
Arg Ala Asp Arg Gly Arg Arg Gly Lys Leu Pro Gly Lys Lys Leu Pro
145                 150                 155                 160
Leu Glu Val Leu Lys Glu Leu Glu Ala Asn Ala Gln Lys Ala Gly Cys
                165                 170                 175
Thr Arg Gly Cys Leu Ile Cys Leu Ser His Ile Lys Cys Thr Ala Lys
            180                 185                 190
Met Lys Lys Trp Leu Pro Gly Arg Cys Glu Ser Trp Glu Gly Asp Lys
            195                 200                 205
Glu Thr Gly Gln Gly Gly Gly Gly Thr Met Asn Leu Glu Ala Arg
    210                 215                 220
Lys Thr Lys Lys Ile Lys Gly Ile Gln Gln Ala Thr Thr Gly Val
225                 230                 235                 240
Ser Gln Glu Thr Ser Glu Asn Pro Gly Asn Lys Thr Ile Val Pro Ala
                245                 250                 255
Thr Leu Pro Gln Leu Thr Pro Thr Leu Val Ser Leu Leu Glu Val Ile
            260                 265                 270
Glu Pro Glu Val Leu Tyr Ala Gly Tyr Asp Ser Ser Val Pro Asp Ser
            275                 280                 285
Thr Trp Arg Ile Met Thr Thr Leu Asn Met Leu Gly Gly Arg Gln Val
            290                 295                 300
Ile Ala Ala Val Lys Trp Ala Lys Ala Ile Pro Gly Phe Arg Asn Leu
305                 310                 315                 320
His Leu Asp Asp Gln Met Thr Leu Leu Gln Tyr Ser Trp Met Phe Leu
                325                 330                 335
Met Ala Phe Ala Leu Gly Trp Arg Ser Tyr Arg Gln Ser Ser Ala Asn
            340                 345                 350
Leu Leu Cys Phe Ala Pro Asp Leu Ile Ile Asn Glu Gln Arg Met Thr
            355                 360                 365
Leu Pro Cys Met Tyr Asp Gln Cys Lys His Met Leu Tyr Val Ser Ser
370                 375                 380
Glu Leu His Arg Leu Gln Val Ser Tyr Glu Glu Tyr Leu Cys Met Lys
385                 390                 395                 400
Thr Leu Leu Leu Leu Ser Ser Val Pro Lys Asp Gly Leu Lys Ser Gln
                405                 410                 415
Glu Leu Phe Asp Glu Ile Arg Met Thr Tyr Ile Lys Glu Leu Gly Lys
            420                 425                 430
Ala Ile Val Lys Arg Glu Gly Asn Ser Ser Gln Asn Trp Gln Arg Phe
            435                 440                 445
Tyr Gln Leu Thr Lys Leu Leu Asp Ser Met His Glu Val Val Glu Asn
    450                 455                 460
Leu Leu Asn Tyr Cys Phe Gln Thr Phe Leu Asp Lys Thr Met Ser Ile
465                 470                 475                 480
Glu Phe Pro Glu Met Leu Ala Glu Ile Ile Thr Asn Gln Ile Pro Lys
                485                 490                 495
Tyr Ser Asn Gly Asn Ile Lys Lys Leu Leu Phe His Gln Lys
            500                 505                 510

<210> SEQ ID NO 22
<211> LENGTH: 215
<212> TYPE: PRT
```

-continued

```
<213> ORGANISM: Artificial Sequence
<220> FEATURE:
<223> OTHER INFORMATION: Synthetic Common amino acid sequence of ALuc
<220> FEATURE:
<221> NAME/KEY: MISC_FEATURE
<222> LOCATION: (3)..(7)
<223> OTHER INFORMATION: Xaa(3)=any a.a.. Xaa(4,6,7)=hydrophobic a.a.
      Xaa(5)=hydrophilic a.a.
<220> FEATURE:
<221> NAME/KEY: MISC_FEATURE
<222> LOCATION: (10)..(11)
<223> OTHER INFORMATION: Xaa=hydrophobic a.a.
<220> FEATURE:
<221> NAME/KEY: MISC_FEATURE
<222> LOCATION: (13)..(13)
<223> OTHER INFORMATION: Xaa=hydrophobic a.a.
<220> FEATURE:
<221> NAME/KEY: MISC_FEATURE
<222> LOCATION: (15)..(16)
<223> OTHER INFORMATION: Xaa=hydrophobic a.a.
<220> FEATURE:
<221> NAME/KEY: MISC_FEATURE
<222> LOCATION: (20)..(20)
<223> OTHER INFORMATION: Xaa=hydrophobic a.a.
<220> FEATURE:
<221> NAME/KEY: MISC_FEATURE
<222> LOCATION: (22)..(22)
<223> OTHER INFORMATION: Xaa=any a.a.
<220> FEATURE:
<221> NAME/KEY: MISC_FEATURE
<222> LOCATION: (24)..(27)
<223> OTHER INFORMATION: Xaa(24,25)=hydophilic a.a. Xaa(26,27)=any a.a.
<220> FEATURE:
<221> NAME/KEY: MISC_FEATURE
<222> LOCATION: (30)..(31)
<223> OTHER INFORMATION: Xaa(30)=any a.a. Xaa(31)=hydrophobic a.a.
<220> FEATURE:
<221> NAME/KEY: MISC_FEATURE
<222> LOCATION: (33)..(39)
<223> OTHER INFORMATION: Xaa(33,35,37-39)=any a.a.
      Xaa(34,36)=hydrophobic a.a.
<220> FEATURE:
<221> NAME/KEY: MISC_FEATURE
<222> LOCATION: (60)..(67)
<223> OTHER INFORMATION: Xaa(60,64-65)=hydrophilic a.a.
      Xaa(61,66)=hydrophobic a.a. Xaa(62-63,67)=any a.a.
<220> FEATURE:
<221> NAME/KEY: MISC_FEATURE
<222> LOCATION: (70)..(75)
<223> OTHER INFORMATION: Xaa(70)=hydrophilic a.a.  Xaa(71-75)=any or no
      a.a.
<220> FEATURE:
<221> NAME/KEY: MISC_FEATURE
<222> LOCATION: (81)..(81)
<223> OTHER INFORMATION: Xaa=hydrophobic a.a.
<220> FEATURE:
<221> NAME/KEY: MISC_FEATURE
<222> LOCATION: (87)..(87)
<223> OTHER INFORMATION: Xaa=any a.a.
<220> FEATURE:
<221> NAME/KEY: MISC_FEATURE
<222> LOCATION: (95)..(95)
<223> OTHER INFORMATION: Xaa=hydrophilic a.a.
<220> FEATURE:
<221> NAME/KEY: MISC_FEATURE
<222> LOCATION: (108)..(108)
<223> OTHER INFORMATION: Xaa=hydrophilic a.a.
<220> FEATURE:
<221> NAME/KEY: MISC_FEATURE
<222> LOCATION: (127)..(127)
<223> OTHER INFORMATION: Xaa=any a.a.
<220> FEATURE:
<221> NAME/KEY: MISC_FEATURE
<222> LOCATION: (131)..(132)
<223> OTHER INFORMATION: Xaa=hydrophilic a.a.
<220> FEATURE:
<221> NAME/KEY: MISC_FEATURE
<222> LOCATION: (138)..(138)
<223> OTHER INFORMATION: Xaa=any a.a.
```

```
<220> FEATURE:
<221> NAME/KEY: MISC_FEATURE
<222> LOCATION: (140)..(142)
<223> OTHER INFORMATION: Xaa=any or no a.a.
<220> FEATURE:
<221> NAME/KEY: MISC_FEATURE
<222> LOCATION: (153)..(153)
<223> OTHER INFORMATION: Xaa=hydrophilic a.a.
<220> FEATURE:
<221> NAME/KEY: MISC_FEATURE
<222> LOCATION: (155)..(155)
<223> OTHER INFORMATION: Xaa=any a.a.
<220> FEATURE:
<221> NAME/KEY: MISC_FEATURE
<222> LOCATION: (168)..(168)
<223> OTHER INFORMATION: Xaa=hydrophobic a.a.
<220> FEATURE:
<221> NAME/KEY: MISC_FEATURE
<222> LOCATION: (185)..(185)
<223> OTHER INFORMATION: Xaa=any a.a.
<220> FEATURE:
<221> NAME/KEY: MISC_FEATURE
<222> LOCATION: (197)..(197)
<223> OTHER INFORMATION: Xaa=any a.a.
<220> FEATURE:
<221> NAME/KEY: MISC_FEATURE
<222> LOCATION: (200)..(200)
<223> OTHER INFORMATION: Xaa=hydrophilic a.a.
<220> FEATURE:
<221> NAME/KEY: MISC_FEATURE
<222> LOCATION: (208)..(208)
<223> OTHER INFORMATION: Xaa=hydrophilic a.a.

<400> SEQUENCE: 22

Met Met Xaa Xaa Xaa Xaa Xaa Phe Ala Xaa Xaa Cys Xaa Ala Xaa Xaa
1               5                   10                  15

Gln Ala Asn Xaa Thr Xaa Asn Xaa Xaa Xaa Asp Ile Xaa Xaa Val
            20                  25                  30

Xaa Xaa Xaa Xaa Xaa Xaa Xaa Asp Leu Glu Thr Asp Leu Phe Thr Ile
        35                  40                  45

Val Glu Asp Met Asn Val Ile Ser Arg Asp Thr Xaa Xaa Xaa Xaa Xaa
50                  55                  60

Xaa Xaa Xaa Arg Gly Xaa Xaa Xaa Xaa Xaa Xaa Leu Pro Gly Lys Lys
65                  70                  75                  80

Xaa Pro Leu Glu Val Leu Xaa Glu Leu Glu Ala Asn Ala Gln Xaa Ala
                85                  90                  95

Gly Cys Thr Arg Gly Cys Leu Ile Cys Leu Ser Xaa Ile Lys Cys Thr
            100                 105                 110

Ala Lys Met Lys Lys Trp Leu Pro Gly Arg Cys Glu Ser Trp Xaa Gly
        115                 120                 125

Asp Lys Xaa Xaa Gly Gln Gly Gly Ile Xaa Glu Xaa Xaa Xaa Val Asp
    130                 135                 140

Ile Pro Glu Ile Pro Gly Phe Lys Xaa Leu Xaa Pro Met Glu Gln Phe
145                 150                 155                 160

Ile Ala Gln Val Asp Leu Cys Xaa Asp Cys Thr Thr Gly Cys Leu Lys
                165                 170                 175

Gly Leu Ala Asn Val Lys Cys Ser Xaa Leu Leu Lys Lys Trp Leu Pro
            180                 185                 190

Ser Arg Cys Ala Xaa Phe Ala Xaa Lys Ile Gln Ala Gln Val Asp Xaa
        195                 200                 205

Ile Lys Gly Ala Gly Gly Ser
    210                 215

<210> SEQ ID NO 23
```

<211> LENGTH: 648
<212> TYPE: DNA
<213> ORGANISM: Artificial Sequence
<220> FEATURE:
<223> OTHER INFORMATION: Synthetic Example of DNA sequence of ALuc

<400> SEQUENCE: 23

```
atgatgggta taaaggttct ttttgctctc atttgctttg cattggtgca ggccaatccc      60
actgagaata aggacgacat cgacatcgtt ggagtcgaag caagtttgg gaccactgat     120
ctggaaacag acctgttcac catcgttgag gatatgaacg tgatttcccg agacacggac     180
gtcgatgcca acagagcaga tcggggacga cgaggtcatg gtgggcttcc agggaagaag     240
atgcccttgg aagtgctgct ggaactggag gcaaacgctc agagggctgg atgcactcgc     300
ggatgcctga tctgcttgtc caagatcaaa tgcacggcga aaatgaagaa gtggcttcct     360
ggccgctgtg agagttgggc tggagataag gagacagggc aaggcggcat aaccgaggaa     420
gagactgtcg acatacccga gatacccggc ttcaaggatc tggaaccgat ggagcagttc     480
attgcccagg ttgacctttg cgttgactgt accacaggtt gcctgaaagg ccttgctaac     540
gtcaagtgca gtgatctcct gaagaagtgg cttccaagta ggtgtgctac gtttgccagc     600
aagatccagg cccaggtcga acaagatcaag ggagctggcg ggtcgtga                 648
```

<210> SEQ ID NO 24
<211> LENGTH: 212
<212> TYPE: PRT
<213> ORGANISM: Artificial Sequence
<220> FEATURE:
<223> OTHER INFORMATION: Synthetic ALuc17

<400> SEQUENCE: 24

```
Met Met Gly Ile Lys Val Leu Phe Ala Leu Ile Cys Phe Ala Leu Val
1               5                   10                  15
Gln Ala Asn Pro Thr Glu Asn Lys Asp Asp Ile Asp Ile Val Gly Val
            20                  25                  30
Glu Gly Lys Phe Gly Thr Thr Asp Leu Glu Thr Asp Leu Phe Thr Ile
        35                  40                  45
Val Glu Asp Met Asn Val Ile Ser Arg Asp Thr Asp Val Asp Ala Asn
    50                  55                  60
Arg Ala Asp Arg Gly Arg Arg Gly Lys Met Pro Gly Lys Lys Leu Pro
65                  70                  75                  80
Lys Ala Val Leu Ile Glu Leu Glu Ala Asn Ala Gln Lys Ala Gly Cys
                85                  90                  95
His Arg Gly Cys Leu Ile Cys Leu Ser His Ile Lys Cys Thr Ala Lys
            100                 105                 110
Met Lys Glu Trp Leu Pro Gly Arg Cys Glu Ser Trp Gly Gly Asp Lys
        115                 120                 125
Glu Thr Gly Gln Ala Gly Ile Val Gly Ala Ile Val Asp Ile Pro Glu
    130                 135                 140
Ile Pro Gly Phe Lys Asp Leu Glu Pro Met Glu Gln Phe Ile Ala Gln
145                 150                 155                 160
Val Asp Leu Cys Val Asp Cys Thr Thr Gly Cys Leu Lys Gly Leu Ala
                165                 170                 175
Asn Val Lys Cys Ser Asp Leu Leu Lys Lys Trp Leu Pro Ser Arg Cys
            180                 185                 190
Ala Thr Phe Ala Ser Lys Ile Gln Ala Gln Val Asp Lys Ile Lys Gly
        195                 200                 205
```

```
Ala Gly Gly Ser
    210

<210> SEQ ID NO 25
<211> LENGTH: 217
<212> TYPE: PRT
<213> ORGANISM: Artificial Sequence
<220> FEATURE:
<223> OTHER INFORMATION: Synthetic ALuc19

<400> SEQUENCE: 25

Met Met Gly Ile Lys Val Leu Phe Ala Leu Ile Cys Phe Ala Leu Val
1               5                   10                  15

Gln Ala Asn Pro Thr Glu Asn Lys Asp Asp Ile Asp Ile Val Gly Val
            20                  25                  30

Glu Gly Lys Phe Gly Thr Thr Asp Leu Glu Thr Asp Leu Phe Thr Ile
        35                  40                  45

Val Glu Asp Met Asn Val Ile Ser Arg Asp Thr Asp Val Asp Ala Asn
    50                  55                  60

Arg Ala Asp Arg Gly Arg Arg Gly Arg Lys Leu Pro Gly Lys Lys Leu
65                  70                  75                  80

Pro Lys Glu Val Leu Lys Ile Leu Glu Ala Asn Ala Gln Arg Ala Gly
                85                  90                  95

Cys His Arg Gly Cys Leu Ile Cys Leu Ser His Ile Lys Cys Thr Ala
            100                 105                 110

Lys Met Lys Gln Trp Leu Pro Gly Arg Cys Glu Ser Trp Glu Gly Asp
        115                 120                 125

Lys Glu Thr Gly Gln Gly Ile Gly Gly Pro Ile Val Asp Ile Gly
    130                 135                 140

Val Leu Gly Pro Glu Ile Pro Gly Phe Lys Asp Leu Glu Pro Met Glu
145                 150                 155                 160

Gln Phe Ile Ala Gln Val Asp Leu Cys Val Asp Cys Thr Thr Gly Cys
                165                 170                 175

Leu Lys Gly Leu Ala Asn Val Lys Cys Ser Asp Leu Leu Lys Lys Trp
            180                 185                 190

Leu Pro Ser Arg Cys Ala Thr Phe Ala Ser Lys Ile Gln Ala Gln Val
        195                 200                 205

Asp Lys Ile Lys Gly Ala Gly Gly Ser
    210                 215

<210> SEQ ID NO 26
<211> LENGTH: 212
<212> TYPE: PRT
<213> ORGANISM: Artificial Sequence
<220> FEATURE:
<223> OTHER INFORMATION: Synthetic ALuc21

<400> SEQUENCE: 26

Met Met Gly Ile Lys Val Leu Phe Ala Leu Ile Cys Phe Ala Leu Val
1               5                   10                  15

Gln Ala Asn Ala Thr Ile Asn Glu Glu Asp Ile Asp Leu Val Ala Ile
            20                  25                  30

Gly Gly Ser Phe Ala Thr Thr Asp Leu Glu Thr Asp Leu Phe Thr Ile
        35                  40                  45

Val Glu Asp Met Asn Val Ile Ser Arg Asp Thr Asp Val Asp Ala Asn
    50                  55                  60

Arg Ala Asp Arg Gly Arg Arg Gly Lys Leu Pro Gly Lys Lys Leu Pro
65                  70                  75                  80
```

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
        115                 120                 125

Glu Thr Gly Gln Gly Gly Ile Gly Glu Ala Ile Val Asp Ile Pro Glu
    130                 135                 140

Ile Pro Gly Phe Lys Asp Leu Glu Pro Met Glu Gln Phe Ile Ala Gln
145                 150                 155                 160

Val Asp Leu Cys Val Asp Cys Thr Thr Gly Cys Leu Lys Gly Leu Ala
                165                 170                 175

Asn Val Lys Cys Ser Asp Leu Leu Lys Lys Trp Leu Pro Ser Arg Cys
            180                 185                 190

Ala Thr Phe Ala Ser Lys Ile Gln Ala Gln Val Asp Lys Ile Lys Gly
        195                 200                 205

Ala Gly Gly Ser
    210

<210> SEQ ID NO 27
<211> LENGTH: 212
<212> TYPE: PRT
<213> ORGANISM: Artificial Sequence
<220> FEATURE:
<223> OTHER INFORMATION: Synthetic ALuc24

<400> SEQUENCE: 27

Met Met Gly Ile Lys Val Leu Phe Ala Leu Ile Cys Phe Ala Leu Val
1               5                   10                  15

Gln Ala Asn Pro Thr Glu Asn Lys Asp Asp Ile Asp Ile Val Gly Val
            20                  25                  30

Glu Gly Lys Phe Gly Thr Thr Asp Leu Glu Thr Asp Leu Phe Thr Ile
        35                  40                  45

Val Glu Asp Met Asn Val Ile Ser Arg Asp Thr Asp Val Asp Ala Asn
    50                  55                  60

Arg Ala Asp Arg Gly Arg Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
        115                 120                 125

Glu Thr Gly Gln Gly Gly Ile Gly Glu Ala Ile Val Asp Ile Pro Glu
    130                 135                 140

Ile Pro Gly Phe Lys Asn Met Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Lys Cys Ser Asn Leu Leu Lys Lys Trp Leu Pro Ser Arg Cys
            180                 185                 190

Lys Gly Phe Ala Asn Lys Ile Gln Ala Glu Val Asp Thr Ile Lys Gly
        195                 200                 205

Leu Gly Gly Ser
    210

<210> SEQ ID NO 28
<211> LENGTH: 212
<212> TYPE: PRT
<213> ORGANISM: Artificial Sequence
<220> FEATURE:
<223> OTHER INFORMATION: Synthetic ALuc26

<400> SEQUENCE: 28

```
Met Met Gly Val Lys Leu Ile Phe Ala Val Leu Cys Val Ala Val Ala
1               5                   10                  15

Gln Ala Asn Ala Thr Ile Asn Glu Asn Phe Glu Asp Ile Asp Leu Val
            20                  25                  30

Ala Ile Gly Gly Ser Phe Ala Asp Leu Glu Thr Asp Leu Phe Thr Ile
        35                  40                  45

Val Glu Asp Met Asn Val Ile Ser Arg Asp Thr Asp Val Asp Ala Asn
    50                  55                  60

Arg Gly Gly Arg Gly Arg Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
        115                 120                 125

Glu Thr Gly Gln Gly Gly Ile Gly Glu Ala Ile Val Asp Ile Pro Glu
    130                 135                 140

Ile Pro Gly Phe Lys Asn Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Lys Cys Ser Asn Leu Leu Lys Lys Trp Leu Pro Ser Arg Cys
            180                 185                 190

Ala Gly Phe Ala Asn Lys Ile Gln Ala Gln Val Asp Thr Ile Lys Gly
        195                 200                 205

Leu Gly Gly Ser
    210
```

<210> SEQ ID NO 29
<211> LENGTH: 212
<212> TYPE: PRT
<213> ORGANISM: Artificial Sequence
<220> FEATURE:
<223> OTHER INFORMATION: Synthetic ALuc27

<400> SEQUENCE: 29

```
Met Met Gly Val Lys Leu Ile Phe Ala Val Leu Cys Val Ala Val Ala
1               5                   10                  15

Gln Ala Asn Ala Thr Ile Asn Glu Asn Phe Glu Asp Ile Asp Leu Val
            20                  25                  30

Ala Ile Gly Gly Ser Phe Ala Asp Leu Glu Thr Asp Leu Phe Thr Ile
        35                  40                  45

Val Glu Asp Met Asn Val Ile Ser Arg Asp Thr Asp Val Asp Ala Asn
    50                  55                  60

Arg Gly Gly Arg Gly Arg Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
```

```
            85                  90                  95
Thr Arg Gly Cys Leu Ile Cys Leu Ser His Ile Lys Cys Thr Ala Lys
            100                 105                 110
Met Lys Lys Trp Leu Pro Gly Arg Cys Glu Ser Trp Glu Gly Asp Lys
            115                 120                 125
Glu Thr Gly Gln Gly Gly Ile Gly Glu Ala Ile Val Asp Ile Pro Glu
            130                 135                 140
Ile Pro Gly Phe Lys Phe Leu Ala Pro Met Glu Gln Phe Ile Ala Gln
145                 150                 155                 160
Val Asp Leu Cys Ala Asp Cys Thr Thr Gly Cys Leu Lys Gly Leu Ala
                165                 170                 175
Asn Val Phe Cys Ser Phe Leu Leu Lys Lys Trp Leu Pro Ser Arg Cys
                180                 185                 190
Ala Gly Phe Ala Phe Lys Ile Gln Ala Gln Val Asp Thr Ile Lys Gly
                195                 200                 205
Leu Gly Gly Ser
    210

<210> SEQ ID NO 30
<211> LENGTH: 212
<212> TYPE: PRT
<213> ORGANISM: Artificial Sequence
<220> FEATURE:
<223> OTHER INFORMATION: Synthetic ALuc28

<400> SEQUENCE: 30

Met Met Gly Val Lys Leu Ile Phe Ala Val Leu Cys Val Ala Val Ala
1               5                   10                  15
Gln Ala Asn Ala Thr Ile Asn Glu Asn Phe Glu Asp Ile Asp Leu Val
            20                  25                  30
Ala Ile Gly Gly Ser Phe Ala Asp Leu Glu Thr Asp Leu Phe Thr Ile
            35                  40                  45
Val Glu Asp Met Asn Val Ile Ser Arg Asp Thr Asp Val Asp Ala Asn
        50                  55                  60
Arg Gly Gly Arg Gly Arg Arg Gly Lys Leu Pro Gly Lys Lys Leu Pro
65                  70                  75                  80
Leu Glu Val Leu Lys Glu Leu Glu Ala Asn Ala Gln Lys Ala Gly Cys
                85                  90                  95
Thr Arg Gly Cys Leu Ile Cys Leu Ser His Ile Lys Cys Thr Ala Lys
            100                 105                 110
Met Lys Lys Trp Leu Pro Gly Arg Cys Glu Ser Trp Glu Gly Asp Lys
            115                 120                 125
Glu Thr Gly Gln Gly Gly Ile Gly Glu Ala Ile Val Asp Ile Pro Glu
            130                 135                 140
Ile Pro Gly Phe Lys Tyr Leu Ala Pro Met Glu Gln Phe Ile Ala Gln
145                 150                 155                 160
Val Asp Leu Cys Ala Asp Cys Thr Thr Gly Cys Leu Lys Gly Leu Ala
                165                 170                 175
Asn Val Tyr Cys Ser Tyr Leu Leu Lys Lys Trp Leu Pro Ser Arg Cys
                180                 185                 190
Ala Gly Phe Ala Tyr Lys Ile Gln Ala Gln Val Asp Thr Ile Lys Gly
                195                 200                 205
Leu Gly Gly Ser
    210
```

-continued

<210> SEQ ID NO 31
<211> LENGTH: 212
<212> TYPE: PRT
<213> ORGANISM: Artificial Sequence
<220> FEATURE:
<223> OTHER INFORMATION: Synthetic ALuc29

<400> SEQUENCE: 31

Met Met Gly Val Lys Leu Ile Phe Ala Val Leu Cys Val Ala Val Ala
1               5                   10                  15

Gln Ala Asn Ala Thr Ile Asn Glu Asn Phe Glu Asp Ile Asp Leu Val
            20                  25                  30

Ala Ile Gly Gly Ser Phe Ala Asp Leu Glu Thr Asp Leu Phe Thr Ile
        35                  40                  45

Val Glu Asp Met Asn Val Ile Ser Arg Asp Thr Asp Val Asp Ala Asn
    50                  55                  60

Arg Gly Gly Arg Gly Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
        115                 120                 125

Glu Thr Gly Gln Gly Gly Ile Gly Glu Ala Ile Val Asp Ile Pro Glu
    130                 135                 140

Ile Pro Gly Phe Lys Trp Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Trp Cys Ser Trp Leu Leu Lys Lys Trp Leu Pro Ser Arg Cys
            180                 185                 190

Ala Gly Phe Ala Trp Lys Ile Gln Ala Gln Val Asp Thr Ile Lys Gly
        195                 200                 205

Leu Gly Gly Ser
    210

<210> SEQ ID NO 32
<211> LENGTH: 212
<212> TYPE: PRT
<213> ORGANISM: Artificial Sequence
<220> FEATURE:
<223> OTHER INFORMATION: Synthetic Aluc30

<400> SEQUENCE: 32

Met Met Gly Ile Lys Val Leu Phe Ala Leu Ile Cys Phe Ala Leu Val
1               5                   10                  15

Gln Ala Asn His His His His His His His Asp Ile Val Gly Val
            20                  25                  30

Glu Gly Lys Phe Gly Thr Thr Asp Leu Glu Thr Asp Leu Phe Thr Ile
        35                  40                  45

Val Glu Asp Met Asn Val Ile Ser Arg Asp Thr Asp Val Asp Ala Asn
    50                  55                  60

Arg Ala Asp Arg Gly Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
            115                 120                 125

Glu Thr Gly Gln Gly Gly Ile Gly Glu Ala Ile Val Asp Ile Pro Glu
            130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                    165                 170                 175

Asn Val Lys Cys Ser Ala Leu Leu Lys Lys Trp Leu Pro Ser Arg Cys
                    180                 185                 190

Ala Gly Phe Ala Asp Lys Ile Gln Ala Gln Val Asp Thr Ile Lys Gly
            195                 200                 205

Ala Gly Gly Ser
    210

<210> SEQ ID NO 33
<211> LENGTH: 212
<212> TYPE: PRT
<213> ORGANISM: Artificial Sequence
<220> FEATURE:
<223> OTHER INFORMATION: Synthetic ALuc31

<400> SEQUENCE: 33

Met Met Gly Ile Lys Val Leu Phe Ala Leu Ile Cys Phe Ala Leu Val
1               5                   10                  15

Gln Ala Asn His His His His His His Asp Ile Val Gly Val
            20                  25                  30

Glu Gly Lys Phe Gly Thr Thr Asp Leu Glu Thr Asp Leu Phe Thr Ile
            35                  40                  45

Val Glu Asp Met Asn Val Ile Ser Arg Asp Thr Asp Val Asp Ala Asn
50                  55                  60

Arg Ala Asp Arg Gly Arg Gly Glu Leu Pro Gly Lys Lys Leu Pro
65                  70                  75                  80

Leu Glu Val Leu Lys Glu Leu Glu Ala Asn Ala Gln Lys Ala Gly Cys
            85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
            115                 120                 125

Glu Thr Gly Gln Gly Gly Ile Gly Glu Ala Ile Val Asp Ile Pro Glu
            130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                    165                 170                 175

Asn Val Lys Cys Ser Ala Leu Leu Lys Lys Trp Leu Pro Ser Arg Cys
                    180                 185                 190

Ala Gly Phe Ala Asp Lys Ile Gln Ala Gln Val Asp Thr Ile Lys Gly
            195                 200                 205

Ala Gly Gly Ser
    210

<210> SEQ ID NO 34
<211> LENGTH: 212

```
<212> TYPE: PRT
<213> ORGANISM: Artificial Sequence
<220> FEATURE:
<223> OTHER INFORMATION: Synthetic ALuc32

<400> SEQUENCE: 34

Met Met Gly Ile Lys Val Leu Phe Ala Leu Ile Cys Phe Ala Leu Val
1               5                   10                  15

Gln Ala Asn Glu Gln Lys Leu Ile Ser Glu Glu Asp Leu Val Gly Val
                20                  25                  30

Glu Gly Lys Phe Gly Thr Thr Asp Leu Glu Thr Asp Leu Phe Thr Ile
            35                  40                  45

Val Glu Asp Met Asn Val Ile Ser Arg Asp Thr Asp Val Asp Ala Asn
    50                  55                  60

Arg Ala Asp Arg Gly Arg Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110

Met Lys Lys Trp Leu Pro Gly Arg Cys Glu Ser Trp Glu Gly Asp Lys
        115                 120                 125

Glu Thr Gly Gln Gly Gly Ile Gly Glu Ala Ile Val Asp Ile Pro Glu
    130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Lys Cys Ser Ala Leu Leu Lys Lys Trp Leu Pro Ser Arg Cys
            180                 185                 190

Ala Gly Phe Ala Asp Lys Ile Gln Ala Gln Val Asp Thr Ile Lys Gly
        195                 200                 205

Ala Gly Gly Ser
    210

<210> SEQ ID NO 35
<211> LENGTH: 212
<212> TYPE: PRT
<213> ORGANISM: Artificial Sequence
<220> FEATURE:
<223> OTHER INFORMATION: Synthetic ALuc33

<400> SEQUENCE: 35

Met Met Gly Ile Lys Val Leu Phe Ala Leu Ile Cys Phe Ala Leu Val
1               5                   10                  15

Gln Ala Asn Met Met Tyr Pro Tyr Asp Val Pro Asp Tyr Ala Gly Val
                20                  25                  30

Glu Gly Lys Phe Gly Thr Thr Asp Leu Glu Thr Asp Leu Phe Thr Ile
            35                  40                  45

Val Glu Asp Met Asn Val Ile Ser Arg Asp Thr Asp Val Asp Ala Asn
    50                  55                  60

Arg Ala Asp Arg Gly Arg Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
            100                 105                 110
```

```
Met Lys Lys Trp Leu Pro Gly Arg Cys Glu Ser Trp Glu Gly Asp Lys
            115                 120                 125

Glu Thr Gly Gln Gly Gly Ile Gly Glu Ala Ile Val Asp Ile Pro Glu
        130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Lys Cys Ser Ala Leu Leu Lys Lys Trp Leu Pro Ser Arg Cys
                180                 185                 190

Ala Gly Phe Ala Asp Lys Ile Gln Ala Gln Val Asp Thr Ile Lys Gly
                195                 200                 205

Ala Gly Gly Ser
        210

<210> SEQ ID NO 36
<211> LENGTH: 212
<212> TYPE: PRT
<213> ORGANISM: Artificial Sequence
<220> FEATURE:
<223> OTHER INFORMATION: Synthetic Aluc34

<400> SEQUENCE: 36

Met Met Gly Ile Lys Val Leu Phe Ala Leu Ile Cys Phe Ala Leu Val
1               5                   10                  15

Gln Ala Asn Met Met Asp Tyr Lys Asp Asp Asp Lys Val Gly Val
            20                  25                  30

Glu Gly Lys Phe Gly Thr Thr Asp Leu Glu Thr Asp Leu Phe Thr Ile
        35                  40                  45

Val Glu Asp Met Asn Val Ile Ser Arg Asp Thr Asp Val Asp Ala Asn
    50                  55                  60

Arg Ala Asp Arg Gly Arg Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95

Thr Arg Gly Cys Leu Ile Cys Leu Ser His Ile Lys Cys Thr Ala Lys
                100                 105                 110

Met Lys Lys Trp Leu Pro Gly Arg Cys Glu Ser Trp Glu Gly Asp Lys
            115                 120                 125

Glu Thr Gly Gln Gly Gly Ile Gly Glu Ala Ile Val Asp Ile Pro Glu
        130                 135                 140

Ile Pro Gly Phe Lys Glu Leu Ala Pro Met Glu Gln Phe Ile Ala Gln
145                 150                 155                 160

Val Asp Leu Cys Ala Asp Cys Thr Thr Gly Cys Leu Lys Gly Leu Ala
                165                 170                 175

Asn Val Lys Cys Ser Ala Leu Leu Lys Lys Trp Leu Pro Ser Arg Cys
                180                 185                 190

Ala Gly Phe Ala Asp Lys Ile Gln Ala Gln Val Asp Thr Ile Lys Gly
                195                 200                 205

Ala Gly Gly Ser
        210

<210> SEQ ID NO 37
<211> LENGTH: 218
<212> TYPE: PRT
<213> ORGANISM: Artificial Sequence
```

```
<220> FEATURE:
<223> OTHER INFORMATION: Synthetic ALucCM (common artificial luciferase)
<220> FEATURE:
<221> NAME/KEY: MISC_FEATURE
<222> LOCATION: (3)..(7)
<223> OTHER INFORMATION: Xaa(3)=any a.a.. Xaa(4,6,7)=aliphatic a.a.
      Xaa(5)=hydrophilic a.a.
<220> FEATURE:
<221> NAME/KEY: MISC_FEATURE
<222> LOCATION: (10)..(11)
<223> OTHER INFORMATION: Xaa(10,11)=aliphatic a.a.
<220> FEATURE:
<221> NAME/KEY: MISC_FEATURE
<222> LOCATION: (13)..(13)
<223> OTHER INFORMATION: Xaa=hydrophobic a.a.
<220> FEATURE:
<221> NAME/KEY: MISC_FEATURE
<222> LOCATION: (15)..(16)
<223> OTHER INFORMATION: Xaa(15)=aliphatic a.a. Xaa(16)=hydrophobic a.a.
<220> FEATURE:
<221> NAME/KEY: MISC_FEATURE
<222> LOCATION: (20)..(27)
<223> OTHER INFORMATION: Xaa(20-27)=any a.a.
<220> FEATURE:
<221> NAME/KEY: MISC_FEATURE
<222> LOCATION: (29)..(39)
<223> OTHER INFORMATION: Xaa(29,30,33)=any a.a.
      Xaa(31,32,37-39)=hydrophilic a.a.
<220> FEATURE:
<221> NAME/KEY: MISC_FEATURE
<222> LOCATION: (60)..(67)
<223> OTHER INFORMATION: Xaa(62-64,67)=any a.a. Xaa(65)=hydrophilic a.a.
      Xaa(61,66)=aliphatic a.a. Xaa(60)=negative a.a.
<220> FEATURE:
<221> NAME/KEY: MISC_FEATURE
<222> LOCATION: (70)..(76)
<223> OTHER INFORMATION: Xaa(74,75)=any or no a.a. Xaa(73)=hydrophilic
      a.a. Xaa(72,76)=aliphatic a.a. Xaa(70,71)=positive a.a.
<220> FEATURE:
<221> NAME/KEY: MISC_FEATURE
<222> LOCATION: (81)..(81)
<223> OTHER INFORMATION: Xaa=aliphatic a.a.
<220> FEATURE:
<221> NAME/KEY: MISC_FEATURE
<222> LOCATION: (83)..(84)
<223> OTHER INFORMATION: Xaa(83,84)=any a.a.
<220> FEATURE:
<221> NAME/KEY: MISC_FEATURE
<222> LOCATION: (87)..(88)
<223> OTHER INFORMATION: Xaa(87,88))=any a.a.
<220> FEATURE:
<221> NAME/KEY: MISC_FEATURE
<222> LOCATION: (95)..(95)
<223> OTHER INFORMATION: Xaa=positive a.a.
<220> FEATURE:
<221> NAME/KEY: MISC_FEATURE
<222> LOCATION: (99)..(99)
<223> OTHER INFORMATION: Xaa=hydrophilic a.a.
<220> FEATURE:
<221> NAME/KEY: MISC_FEATURE
<222> LOCATION: (108)..(108)
<223> OTHER INFORMATION: Xaa=any a.a.
<220> FEATURE:
<221> NAME/KEY: MISC_FEATURE
<222> LOCATION: (117)..(117)
<223> OTHER INFORMATION: Xaa=hydrophilic a.a.
<220> FEATURE:
<221> NAME/KEY: MISC_FEATURE
<222> LOCATION: (127)..(127)
<223> OTHER INFORMATION: Xaa=any a.a.
<220> FEATURE:
<221> NAME/KEY: MISC_FEATURE
<222> LOCATION: (135)..(135)
<223> OTHER INFORMATION: Xaa=aliphatic a.a.
<220> FEATURE:
<221> NAME/KEY: MISC_FEATURE
<222> LOCATION: (137)..(145)
<223> OTHER INFORMATION: Xaa(137-140)=any or no a.a. Xaa(140-145)=any
      a.a.
```

-continued

```
<220> FEATURE:
<221> NAME/KEY: MISC_FEATURE
<222> LOCATION: (147)..(148)
<223> OTHER INFORMATION: Xaa(147)=any a.a. Xaa(148)=hydrophobic a.a.
<220> FEATURE:
<221> NAME/KEY: MISC_FEATURE
<222> LOCATION: (156)..(158)
<223> OTHER INFORMATION: Xaa(1596,158)=any a.a. Xaa(157)=aliphatic a.a.
<220> FEATURE:
<221> NAME/KEY: MISC_FEATURE
<222> LOCATION: (171)..(171)
<223> OTHER INFORMATION: Xaa=hydrophobic a.a.
<220> FEATURE:
<221> NAME/KEY: MISC_FEATURE
<222> LOCATION: (185)..(185)
<223> OTHER INFORMATION: Xaa=any a.a.
<220> FEATURE:
<221> NAME/KEY: MISC_FEATURE
<222> LOCATION: (188)..(188)
<223> OTHER INFORMATION: Xaa=any a.a.
<220> FEATURE:
<221> NAME/KEY: MISC_FEATURE
<222> LOCATION: (199)..(200)
<223> OTHER INFORMATION: Xaa(199)=any a.a. Xaa(200)=aliphatic a.a.
<220> FEATURE:
<221> NAME/KEY: MISC_FEATURE
<222> LOCATION: (203)..(203)
<223> OTHER INFORMATION: Xaa=any a.a.
<220> FEATURE:
<221> NAME/KEY: MISC_FEATURE
<222> LOCATION: (208)..(208)
<223> OTHER INFORMATION: Xaa=negative a.a.
<220> FEATURE:
<221> NAME/KEY: MISC_FEATURE
<222> LOCATION: (211)..(211)
<223> OTHER INFORMATION: Xaa=hydrophilic a.a.
<220> FEATURE:
<221> NAME/KEY: MISC_FEATURE
<222> LOCATION: (215)..(215)
<223> OTHER INFORMATION: Xaa=hydrophobic a.a

<400> SEQUENCE: 37

Met Met Xaa Xaa Xaa Xaa Xaa Phe Ala Xaa Xaa Cys Xaa Ala Xaa Xaa
1               5                   10                  15

Gln Ala Asn Xaa Xaa Xaa Xaa Xaa Xaa Asp Xaa Xaa Xaa Xaa
            20                  25                  30

Xaa Xaa Xaa Xaa Xaa Xaa Xaa Asp Leu Glu Thr Asp Leu Phe Thr Ile
        35                  40                  45

Val Glu Asp Met Asn Val Ile Ser Arg Asp Thr Xaa Xaa Xaa Xaa Xaa
50                  55                  60

Xaa Xaa Xaa Arg Gly Xaa Xaa Xaa Xaa Xaa Xaa Xaa Pro Gly Lys Lys
65                  70                  75                  80

Xaa Pro Xaa Xaa Val Leu Xaa Xaa Leu Glu Ala Asn Ala Gln Xaa Ala
                85                  90                  95

Gly Cys Xaa Arg Gly Cys Leu Ile Cys Leu Ser Xaa Ile Lys Cys Thr
            100                 105                 110

Ala Lys Met Lys Xaa Trp Leu Pro Gly Arg Cys Glu Ser Trp Xaa Gly
        115                 120                 125

Asp Lys Glu Thr Gly Gln Xaa Gly Xaa Xaa Xaa Xaa Xaa Xaa Xaa
    130                 135                 140

Xaa Val Xaa Xaa Pro Glu Ile Pro Gly Phe Lys Xaa Xaa Xaa Pro Met
145                 150                 155                 160

Glu Gln Phe Ile Ala Gln Val Asp Leu Cys Xaa Asp Cys Thr Thr Gly
                165                 170                 175

Cys Leu Lys Gly Leu Ala Asn Val Xaa Cys Ser Xaa Leu Leu Lys Lys
            180                 185                 190
```

```
Trp Leu Pro Ser Arg Cys Xaa Xaa Phe Ala Xaa Lys Ile Gln Ala Xaa
            195                 200                 205

Val Asp Xaa Ile Lys Gly Xaa Gly Gly Ser
    210                 215

<210> SEQ ID NO 38
<211> LENGTH: 221
<212> TYPE: PRT
<213> ORGANISM: Artificial Sequence
<220> FEATURE:
<223> OTHER INFORMATION: Synthetic ALucCM (common artificial luciferase)
<220> FEATURE:
<221> NAME/KEY: MISC_FEATURE
<222> LOCATION: (3)..(7)
<223> OTHER INFORMATION: Xaa(3)=any a.a. Xaa(5)=hydrophobic a.a.
      Xaa(4,6,7)=aliphatic a.a.
<220> FEATURE:
<221> NAME/KEY: MISC_FEATURE
<222> LOCATION: (10)..(11)
<223> OTHER INFORMATION: Xaa(10,11)=aliphatic a.a.
<220> FEATURE:
<221> NAME/KEY: MISC_FEATURE
<222> LOCATION: (13)..(13)
<223> OTHER INFORMATION: Xaa=hydrophobic a.a.
<220> FEATURE:
<221> NAME/KEY: MISC_FEATURE
<222> LOCATION: (15)..(16)
<223> OTHER INFORMATION: Xaa(16)=hydrophobic a.a. Xaa(15)=aliphatic a.a.
<220> FEATURE:
<221> NAME/KEY: MISC_FEATURE
<222> LOCATION: (20)..(29)
<223> OTHER INFORMATION: Xaa(20,21,24-29-29)=any a.a. Xaa(22,23)=any or
      no a.a.
<220> FEATURE:
<221> NAME/KEY: MISC_FEATURE
<222> LOCATION: (31)..(35)
<223> OTHER INFORMATION: Xaa(31,32,35)=any a.a. Xaa(33,34)=aliphatic
      a.a.
<220> FEATURE:
<221> NAME/KEY: MISC_FEATURE
<222> LOCATION: (37)..(37)
<223> OTHER INFORMATION: Xaa(37)=any a.a.
<220> FEATURE:
<221> NAME/KEY: MISC_FEATURE
<222> LOCATION: (39)..(41)
<223> OTHER INFORMATION: Xaa(39,40)=aliphatic or no a.a.
      Xaa(41)=aliphatic a.a.
<220> FEATURE:
<221> NAME/KEY: MISC_FEATURE
<222> LOCATION: (62)..(69)
<223> OTHER INFORMATION: Xaa(64-66,69)=any a.a. Xaa(67)=hydrophobic a.a.
      Xaa(63,68)=aliphatic a.a. Xaa(62)=negative a.a.
<220> FEATURE:
<221> NAME/KEY: MISC_FEATURE
<222> LOCATION: (72)..(78)
<223> OTHER INFORMATION: Xaa(76,77)=any or no a.a. Xaa(75)=hydrophilic
      a.a. Xaa(74)=aliphatic or no a.a. Xaa(78)=aliphatic a.a.
      Xaa(72,73)=positive or no a.a.
<220> FEATURE:
<221> NAME/KEY: MISC_FEATURE
<222> LOCATION: (83)..(83)
<223> OTHER INFORMATION: Xaa=aliphatic a.a.
<220> FEATURE:
<221> NAME/KEY: MISC_FEATURE
<222> LOCATION: (85)..(86)
<223> OTHER INFORMATION: Xaa(85,86)=any a.a.
<220> FEATURE:
<221> NAME/KEY: MISC_FEATURE
<222> LOCATION: (89)..(90)
<223> OTHER INFORMATION: Xaa(89,90)=any a.a.
<220> FEATURE:
<221> NAME/KEY: MISC_FEATURE
<222> LOCATION: (97)..(97)
<223> OTHER INFORMATION: Xaa=positive a.a.
<220> FEATURE:
<221> NAME/KEY: MISC_FEATURE
<222> LOCATION: (101)..(101)
```

```
<223> OTHER INFORMATION: Xaa=hydrophilic a.a.
<220> FEATURE:
<221> NAME/KEY: MISC_FEATURE
<222> LOCATION: (110)..(110)
<223> OTHER INFORMATION: Xaa=positive a.a.
<220> FEATURE:
<221> NAME/KEY: MISC_FEATURE
<222> LOCATION: (119)..(119)
<223> OTHER INFORMATION: Xaa=hydrophilic a.a.
<220> FEATURE:
<221> NAME/KEY: MISC_FEATURE
<222> LOCATION: (129)..(129)
<223> OTHER INFORMATION: Xaa=any a.a.
<220> FEATURE:
<221> NAME/KEY: MISC_FEATURE
<222> LOCATION: (137)..(137)
<223> OTHER INFORMATION: Xaa=aliphatic a.a.
<220> FEATURE:
<221> NAME/KEY: MISC_FEATURE
<222> LOCATION: (140)..(144)
<223> OTHER INFORMATION: Xaa(140)=any or no a.a. Xaa(141-144)=any a.a.
<220> FEATURE:
<221> NAME/KEY: MISC_FEATURE
<222> LOCATION: (148)..(151)
<223> OTHER INFORMATION: Xaa(148-151)=any or no a.a.
<220> FEATURE:
<221> NAME/KEY: MISC_FEATURE
<222> LOCATION: (159)..(161)
<223> OTHER INFORMATION: Xaa(159,161)=any a.a. Xaa(160)=aliphatic a.a.
<220> FEATURE:
<221> NAME/KEY: misc_feature
<222> LOCATION: (174)..(174)
<223> OTHER INFORMATION: Xaa can be any naturally occurring amino acid
<220> FEATURE:
<221> NAME/KEY: MISC_FEATURE
<222> LOCATION: (188)..(188)
<223> OTHER INFORMATION: Xaa=any a.a.
<220> FEATURE:
<221> NAME/KEY: MISC_FEATURE
<222> LOCATION: (191)..(191)
<223> OTHER INFORMATION: Xaa=any a.a.
<220> FEATURE:
<221> NAME/KEY: MISC_FEATURE
<222> LOCATION: (202)..(203)
<223> OTHER INFORMATION: Xaa(202)=any a.a. Xaa(203)=aliphatic a.a.
<220> FEATURE:
<221> NAME/KEY: MISC_FEATURE
<222> LOCATION: (206)..(206)
<223> OTHER INFORMATION: Xaa(206)=any a.a.
<220> FEATURE:
<221> NAME/KEY: MISC_FEATURE
<222> LOCATION: (211)..(211)
<223> OTHER INFORMATION: Xaa=negative a.a.
<220> FEATURE:
<221> NAME/KEY: MISC_FEATURE
<222> LOCATION: (214)..(214)
<223> OTHER INFORMATION: Xaa(214)=hydrophilic a.a.
<220> FEATURE:
<221> NAME/KEY: MISC_FEATURE
<222> LOCATION: (218)..(218)
<223> OTHER INFORMATION: Xaa=hydrophobic a.a.

<400> SEQUENCE: 38

Met Met Xaa Xaa Xaa Xaa Xaa Phe Ala Xaa Xaa Cys Xaa Ala Xaa Xaa
1               5                   10                  15

Gln Ala Asn Xaa Xaa Xaa Xaa Xaa Xaa Xaa Xaa Asp Xaa Xaa
            20                  25                  30

Xaa Xaa Xaa Gly Xaa Phe Xaa Xaa Xaa Asp Leu Glu Thr Asp Leu Phe
        35                  40                  45

Thr Ile Val Glu Asp Met Asn Val Ile Ser Arg Asp Thr Xaa Xaa Xaa
    50                  55                  60

Xaa Xaa Xaa Xaa Xaa Arg Gly Xaa Xaa Xaa Xaa Xaa Xaa Pro Gly
65                  70                  75                  80
```

```
Lys Lys Xaa Pro Xaa Xaa Val Leu Xaa Xaa Leu Glu Ala Asn Ala Gln
             85                  90                  95

Xaa Ala Gly Cys Xaa Arg Gly Cys Leu Ile Cys Leu Ser Xaa Ile Lys
            100                 105                 110

Cys Thr Ala Lys Met Lys Xaa Trp Leu Pro Gly Arg Cys Glu Ser Trp
            115                 120                 125

Xaa Gly Asp Lys Glu Thr Gly Gln Xaa Gly Ile Xaa Xaa Xaa Xaa Xaa
            130                 135                 140

Val Asp Ile Xaa Xaa Xaa Pro Glu Ile Pro Gly Phe Lys Xaa Xaa
145                 150                 155                 160

Xaa Pro Met Glu Gln Phe Ile Ala Gln Val Asp Leu Cys Xaa Asp Cys
                165                 170                 175

Thr Thr Gly Cys Leu Lys Gly Leu Ala Asn Val Xaa Cys Ser Xaa Leu
            180                 185                 190

Leu Lys Lys Trp Leu Pro Ser Arg Cys Xaa Xaa Phe Ala Xaa Lys Ile
            195                 200                 205

Gln Ala Xaa Val Asp Xaa Ile Lys Gly Xaa Gly Gly Ser
    210                 215                 220

<210> SEQ ID NO 39
<211> LENGTH: 69
<212> TYPE: PRT
<213> ORGANISM: Artificial Sequence
<220> FEATURE:
<223> OTHER INFORMATION: Synthetic ALuc common partial sequence

<400> SEQUENCE: 39

Met Met Gly Ile Lys Val Leu Phe Ala Leu Ile Cys Phe Ala Leu Val
1               5                   10                  15

Gln Ala Asn Pro Thr Glu Asn Lys Asp Asp Ile Asp Ile Val Gly Val
                20                  25                  30

Glu Gly Lys Phe Gly Thr Thr Asp Leu Glu Thr Asp Leu Phe Thr Ile
            35                  40                  45

Val Glu Asp Met Asn Val Ile Ser Arg Asp Thr Asp Val Asp Ala Asn
    50                  55                  60

Arg Ala Asp Arg Gly
65

<210> SEQ ID NO 40
<211> LENGTH: 149
<212> TYPE: PRT
<213> ORGANISM: Artificial Sequence
<220> FEATURE:
<223> OTHER INFORMATION: Synthetic ALuc common partial sequence

<400> SEQUENCE: 40

Met Met Gly Val Lys Leu Ile Phe Ala Val Leu Cys Val Ala Val Ala
1               5                   10                  15

Gln Ala Asn Ala Thr Ile Asn Glu Asn Phe Glu Asp Ile Asp Leu Val
                20                  25                  30

Ala Ile Gly Gly Ser Phe Ala Asp Leu Glu Thr Asp Leu Phe Thr Ile
            35                  40                  45

Val Glu Asp Met Asn Val Ile Ser Arg Asp Thr Asp Val Asp Ala Asn
    50                  55                  60

Arg Gly Gly Arg Gly Arg Gly Lys Leu Pro Gly Lys Lys Leu Pro
65                  70                  75                  80

Leu Glu Val Leu Lys Glu Leu Glu Ala Asn Ala Gln Lys Ala Gly Cys
                85                  90                  95
```

```
Thr Arg Gly Cys Leu Ile Cys Leu Ser His Ile Lys Cys Thr Ala Lys
            100                 105                 110
Met Lys Lys Trp Leu Pro Gly Arg Cys Glu Ser Trp Glu Gly Asp Lys
        115                 120                 125
Glu Thr Gly Gln Gly Ile Gly Glu Ala Ile Val Asp Ile Pro Glu
    130                 135                 140
Ile Pro Gly Phe Lys
145

<210> SEQ ID NO 41
<211> LENGTH: 8
<212> TYPE: PRT
<213> ORGANISM: Artificial Sequence
<220> FEATURE:
<223> OTHER INFORMATION: Synthetic ALuc partial sequence

<400> SEQUENCE: 41

Pro Thr Glu Asn Lys Asp Asp Ile
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic ALuc partial sequence

<400> SEQUENCE: 42

Ala Thr Ile Asn Glu Glu Asp Ile
1               5

<210> SEQ ID NO 43
<211> LENGTH: 8
<212> TYPE: PRT
<213> ORGANISM: Artificial Sequence
<220> FEATURE:
<223> OTHER INFORMATION: Synthetic ALuc partial sequence

<400> SEQUENCE: 43

Ala Thr Ile Asn Glu Asn Phe Glu
1               5

<210> SEQ ID NO 44
<211> LENGTH: 8
<212> TYPE: PRT
<213> ORGANISM: Artificial Sequence
<220> FEATURE:
<223> OTHER INFORMATION: Synthetic ALuc partial sequence

<400> SEQUENCE: 44

His His His His His His His His
1               5

<210> SEQ ID NO 45
<211> LENGTH: 7
<212> TYPE: PRT
<213> ORGANISM: Artificial Sequence
<220> FEATURE:
<223> OTHER INFORMATION: Synthetic ALuc partial sequence

<400> SEQUENCE: 45

Glu Lys Leu Ile Ser Glu Glu
1               5
```

```
<210> SEQ ID NO 46
<211> LENGTH: 8
<212> TYPE: PRT
<213> ORGANISM: Artificial Sequence
<220> FEATURE:
<223> OTHER INFORMATION: Synthetic ALuc partial sequence

<400> SEQUENCE: 46

Met Met Tyr Pro Tyr Asp Val Pro
1               5

<210> SEQ ID NO 47
<211> LENGTH: 8
<212> TYPE: PRT
<213> ORGANISM: Artificial Sequence
<220> FEATURE:
<223> OTHER INFORMATION: Synthetic ALuc partial sequence

<400> SEQUENCE: 47

Met Met Asp Tyr Lys Asp Asp Asp
1               5

<210> SEQ ID NO 48
<211> LENGTH: 4
<212> TYPE: PRT
<213> ORGANISM: Artificial Sequence
<220> FEATURE:
<223> OTHER INFORMATION: Synthetic ALuc partial sequence

<400> SEQUENCE: 48

Ile Gly Glu Ala
1

<210> SEQ ID NO 49
<211> LENGTH: 4
<212> TYPE: PRT
<213> ORGANISM: Artificial Sequence
<220> FEATURE:
<223> OTHER INFORMATION: Synthetic ALuc partial sequence

<400> SEQUENCE: 49

Ile Val Gly Ala
1

<210> SEQ ID NO 50
<211> LENGTH: 5
<212> TYPE: PRT
<213> ORGANISM: Artificial Sequence
<220> FEATURE:
<223> OTHER INFORMATION: Synthetic ALuc partial sequence

<400> SEQUENCE: 50

Ile Thr Glu Glu Glu
1               5

<210> SEQ ID NO 51
<211> LENGTH: 7
<212> TYPE: PRT
<213> ORGANISM: Artificial Sequence
<220> FEATURE:
<223> OTHER INFORMATION: Synthetic ALuc partial sequence

<400> SEQUENCE: 51

Ile Gly Gly Pro Ile Val Asp
1               5

<210> SEQ ID NO 52
```

```
<211> LENGTH: 8
<212> TYPE: PRT
<213> ORGANISM: Artificial Sequence
<220> FEATURE:
<223> OTHER INFORMATION: Synthetic ALuc partial sequence

<400> SEQUENCE: 52

Pro Thr Glu Asn Lys Asp Asp Ile
1               5

<210> SEQ ID NO 53
<211> LENGTH: 8
<212> TYPE: PRT
<213> ORGANISM: Artificial Sequence
<220> FEATURE:
<223> OTHER INFORMATION: Synthetic ALuc partial sequence

<400> SEQUENCE: 53

Ala Thr Ile Asn Glu Glu Asp Ile
1               5

<210> SEQ ID NO 54
<211> LENGTH: 10
<212> TYPE: PRT
<213> ORGANISM: Artificial Sequence
<220> FEATURE:
<223> OTHER INFORMATION: Synthetic ALuc partial sequence

<400> SEQUENCE: 54

Ala Thr Ile Asn Glu Asn Phe Glu Asp Ile
1               5                   10

<210> SEQ ID NO 55
<211> LENGTH: 8
<212> TYPE: PRT
<213> ORGANISM: Artificial Sequence
<220> FEATURE:
<223> OTHER INFORMATION: Synthetic ALuc partial sequence

<400> SEQUENCE: 55

His His His His His His His His
1               5

<210> SEQ ID NO 56
<211> LENGTH: 7
<212> TYPE: PRT
<213> ORGANISM: Artificial Sequence
<220> FEATURE:
<223> OTHER INFORMATION: Synthetic ALuc partial sequence

<400> SEQUENCE: 56

Glu Lys Leu Ile Ser Glu Glu
1               5

<210> SEQ ID NO 57
<211> LENGTH: 8
<212> TYPE: PRT
<213> ORGANISM: Artificial Sequence
<220> FEATURE:
<223> OTHER INFORMATION: Synthetic ALuc partial sequence

<400> SEQUENCE: 57

Met Met Tyr Pro Tyr Asp Val Pro
1               5

<210> SEQ ID NO 58
<211> LENGTH: 8
```

```
<212> TYPE: PRT
<213> ORGANISM: Artificial Sequence
<220> FEATURE:
<223> OTHER INFORMATION: Synthetic ALuc partial sequence

<400> SEQUENCE: 58

Met Met Asp Tyr Lys Asp Asp Asp
1               5

<210> SEQ ID NO 59
<211> LENGTH: 5
<212> TYPE: PRT
<213> ORGANISM: Artificial Sequence
<220> FEATURE:
<223> OTHER INFORMATION: Synthetic ALuc partial sequence

<400> SEQUENCE: 59

Thr Glu Glu Glu Thr
1               5

<210> SEQ ID NO 60
<211> LENGTH: 4
<212> TYPE: PRT
<213> ORGANISM: Artificial Sequence
<220> FEATURE:
<223> OTHER INFORMATION: Synthetic ALuc partial sequence

<400> SEQUENCE: 60

Gly Glu Ala Ile
1

<210> SEQ ID NO 61
<211> LENGTH: 4
<212> TYPE: PRT
<213> ORGANISM: Artificial Sequence
<220> FEATURE:
<223> OTHER INFORMATION: Synthetic ALuc partial sequence

<400> SEQUENCE: 61

Val Gly Ala Ile
1

<210> SEQ ID NO 62
<211> LENGTH: 4
<212> TYPE: PRT
<213> ORGANISM: Artificial Sequence
<220> FEATURE:
<223> OTHER INFORMATION: Synthetic ALuc partial sequence

<400> SEQUENCE: 62

Gly Val Leu Gly
1
```